US008962633B2

(12) United States Patent
Shi et al.

(10) Patent No.: US 8,962,633 B2
(45) Date of Patent: Feb. 24, 2015

(54) METHODS OF TREATMENT AND PREVENTION OF METABOLIC BONE DISEASES AND DISORDERS

(75) Inventors: Yi Shi, Boothwyn, PA (US); Theresa Freeman, Haddon Township, NJ (US)

(73) Assignee: Thomas Jefferson University, Philadelphia, PA (US)

( * ) Notice: Subject to any disclaimer, the term of this patent is extended or adjusted under 35 U.S.C. 154(b) by 1440 days.

(21) Appl. No.: 12/118,985

(22) Filed: May 12, 2008

(65) Prior Publication Data
US 2008/0280829 A1 Nov. 13, 2008

Related U.S. Application Data

(60) Provisional application No. 60/928,921, filed on May 11, 2007.

(51) Int. Cl.
C07D 239/70 (2006.01)
A61K 31/517 (2006.01)
A61K 31/4709 (2006.01)
A61K 38/02 (2006.01)
A61K 31/4985 (2006.01)
A61K 31/505 (2006.01)
A61K 31/7088 (2006.01)
A61K 31/56 (2006.01)
A61K 38/17 (2006.01)

(52) U.S. Cl.
CPC ............. *A61K 38/17* (2013.01); *A61K 31/4709* (2013.01); *A61K 38/02* (2013.01); *A61K 31/4985* (2013.01); *A61K 31/505* (2013.01); *A61K 31/7088* (2013.01); *A61K 31/56* (2013.01)
USPC ....................................... 514/258.1; 544/253

(58) Field of Classification Search
None
See application file for complete search history.

(56) References Cited

U.S. PATENT DOCUMENTS

| 6,649,619 | B1 | 11/2003 | Hickey et al. |
| 7,153,861 | B2 | 12/2006 | Leach et al. |
| 7,169,924 | B2 | 1/2007 | Elliott et al. |
| 7,829,535 | B2 * | 11/2010 | O'Connor .................. 514/16.7 |
| 2005/0033052 | A1 | 2/2005 | Leach et al. |
| 2007/0032430 | A1 | 2/2007 | Fogelman et al. |
| 2008/0090851 | A1 | 4/2008 | Leach |
| 2008/0090852 | A1 | 4/2008 | Leach |
| 2008/0103156 | A1 | 5/2008 | Leach |

FOREIGN PATENT DOCUMENTS

| WO | 96/13484 A1 | 5/1996 |
| WO | 96/19451 A1 | 6/1996 |
| WO | 97/02242 A1 | 1/1997 |
| WO | 97/21676 A1 | 6/1997 |
| WO | 97/41098 A1 | 11/1997 |
| WO | 97/41099 A1 | 11/1997 |
| WO | 01/60805 A1 | 8/2001 |
| WO | 02/30904 A1 | 4/2002 |
| WO | 02/30911 A1 | 4/2002 |
| WO | 03/016287 A2 | 2/2003 |
| WO | 03/041712 A1 | 5/2003 |
| WO | 03/042179 A1 | 5/2003 |
| WO | 03/042206 A1 | 5/2003 |
| WO | 03/042218 A1 | 5/2003 |
| WO | 03/086400 A1 | 10/2003 |
| WO | 03/087088 A2 | 10/2003 |
| WO | 2008140450 A1 | 11/2008 |

OTHER PUBLICATIONS

Blackie et al. (Bioorganic & Medicinal Chemistry Letters, vol. 13, pp. 1067-1070; 2003).*
Raisz (N Engl J Med, vol. 353, pp. 164-171; 2005).*
Hörig et al., J. Translational Med. 2:44 (2004).*
Baron, R. et al., "Cell-mediated Extracellular Acidification and Bone Resorption: Evidence for a Low pH in Resorbing Lacunae and Localization of a 100-kD Lysosomal Membrane Protein at the Osteoclast Ruffled Border." The Journal of Cell Biology 101:2210-2222, 1985.
Connolly, C. J. C. et al., "Discovery and Structure-Activity Studies of a Novel Series of Pyrido[2,3-d]Pyrimidine Tyrosine Kinase Inhibitors." Bioorganic & Medicinal Chemistry Letters 7(18):2415-2420, 1997.
Chang, Y. et al "Synthesis and application of functionally diverse 2,6,9-trisubstituted purine libraries as CDK inhibitors." Chemistry & Biology 6(6):361-375, 1999.
Blair, H. C. et al., "Osteoclastic Bone Resorption by a Polarized Vacuolar Proton Pump." Science 245:855-857, 1989.
David, P. and Baron, R., "The vacuolar H+-ATPase: A potential target for drug development in bone diseases." Exp Opin Invest Drugs 4(8):725-740, 1995.
Legraverend, M. et al., "Synthesis and In Vitro Evaluation of Novel 2,6,9-Trisubstituted Purines Acting as Cyclin-dependent Kinase Inhibitors." Bioorganic & Medicinal Chemistry 7:1281-1293, 1999.
Forgac, M., "Regulation of Vacuolar Acidification." Organellar Ion Channels and Transporters, Rockefeller U P 121-132, 1996.
Klutchko, S. R. et al., "2-Substituted Aminopyrido[2,3-d]pyrimidin-7(8H)-ones. Structure-Activity Relationships Against Selected Tyrosine Kinases and in Vivo and in Vivo Anticancer Activity." J Med Chem 41:3276-3292, 1998.
Finbow, M. E. and Harrison, M. A., "The vacuolar H+-ATPase: a universal proton pump of eukaryotes." Biochem J. 324:697-712, 1997.
Farina, C. and Gagliardi, S., "Selective inhibitors of vacuolar H+-ATPase of osteoclasts with bone antiresorptive activity." Exp Opin Ther Patents 9(2):157-168, 1999.

(Continued)

*Primary Examiner* — Michael Barker
(74) *Attorney, Agent, or Firm* — Nixon Peabody LLP.

(57) ABSTRACT

The present invention provides compostions and methods useful for treating and preventing metabolic bone diseases and disorders by inhibition of Lp-PLA$_2$. The compositions and methods are useful for treating and preventing metabolic bone diseases and disorders such as, for example osteoporosis, osteopenia and osteopenia related diseases and abnormal bone marrow.

11 Claims, 12 Drawing Sheets

(56) References Cited

OTHER PUBLICATIONS

Lev, S. et al., "Protein tyrosine kinase PYK2 involved with Ca2+-induced regulation of ion channel and MAP kinase functions." Nature 376:737-745, 1995.

Trumpp-Kallmeyer, S. et al., "Development of a Binding Model to Protein Tyrosine Kinases for Substituted Pyrido[2,3-d]pyrimidine Inhibitors." J Med Chem 41:1752-1763, 1998.

Palmer, B. D. et al., "Tyrosine Kinase Inhibitors. 11. Soluble Analogues of Pyrrolo- and Pyrazoloquinazolies as Epidermal Growth Factor Receptor Inhibitors: Synthesis, Biological Evaluation, and Modeling of the Mode of Binding." J Med Chem 40:1519-1529, 1997.

Missbach, M. et al., "A Novel Inhibitor of the Tyrosine Kinase Src Suppresses Phosphorylation of Its Major Cellular Substrates and Reduces Bone Resorption In Vitro and in Rodent Models In Vivo." Bone 24(5):437-449, 1999.

Reginster, J. Y. et al., "Promising new agents in osteoporosis." (Abstract) Drugs R D 1(3):195-201, 1999.

Chestnut, C. H., III, et al., "Effects of Oral Ibandronate Administered Daily or Intermittently on Fracture Risk in Postmenopausal Osteoporosis." Journal of Bone and Mineral Research 19(8):1241-1249, 2004.

Boekholdt, S. M. et al., "Serum Levels of Type II Secretory Phospholipase A2 and the Risk of Future Coronary Artery Disease in Apparently Healthy Men and Women: the EPIC-Norfolk Prospective Population Study." Arterioscler Thromb Vasc Biol 25:839-846, 2005.

Mehta, K. et al., "The gelatinous bone marrow (serous atrophy) in patients with acquired immunodeficiency syndrome. Evidence of excess sulfated glycosaminoglycan." Arch Pathol Lab Med 116(5):504-508, 1992 (Abstract only).

Shi et al., Atherosclerosis, 191:54-62 (2007). "Role of lipoprotein-associated phospholipase A2 in leukocyte activation and inflammatory responses."

Tew et al., Biochemistry, 37:10087-10093 (1998). "Mechanism of inhibition of LDL Phospholipase A2 by Monocyclic-β-lactams. Burst Kinetics and the Effect of Stereochemistry".

* cited by examiner

DM/HC + Lp-PLA2 INHIBITOR

DM/HC + Lp-PLA2 INHIBITOR

DM/HC + Lp-PLA2 INHIBITOR

DM/HC + Lp-PLA2 INHIBITOR

DM/HC

DM/HC + Lp-PLA2 INHIBITOR

DM/HC

DM/HC + Lp-PLA2 INHIBITOR

SEQUENCE LISTING

<160> NUMBER OF SEQ ID NOS: 5

<210> SEQ ID NO 1
<211> LENGTH: 1505
<212> TYPE: DNA
<213> ORGANISM: Homo sapiens

<400> SEQUENCE: 1

| | | | | | |
|---|---|---|---|---|---|
| gctggtcgga | ggctcgcagt | gctgtcggcg | agaagcagtc | gggtttggag | cgcttgggtc | 60 |
| gcgttggtgc | gcggtggaac | gcgcccaggg | accccagttc | ccgcgagcag | ctccgcgccg | 120 |
| cgcctgagag | actaagctga | aactgctgct | cagctcccaa | gatggtgcca | cccaaattgc | 180 |
| atgtgctttt | ctgcctctgc | ggctgcctgg | ctgtggttta | tccttttgac | tggcaataca | 240 |
| taaatcctgt | tgcccatatg | aaatcatcag | catgggtcaa | caaaatacaa | gtactgatgg | 300 |
| ctgctgcaag | cttttggcca | actaaaatcc | ccgggggaaa | tgggccttat | tccgttggtt | 360 |
| gtacagactt | aatgtttgat | cacactaata | agggcacctt | cttgcgttta | tattatccat | 420 |
| cccaagataa | tgatcgcctt | gacaccctt | ggatcccaaa | taagaatat | ttttggggtc | 480 |
| ttagcaaatt | tcttggaaca | cactggctta | tgggcaacat | tttgaggtta | ctctttggtt | 540 |
| caatgacaac | tcctgcaaac | tggaattccc | ctctgaggcc | tggtgaaaaa | tatccacttg | 600 |
| ttgtttttc | tcatggtctt | ggggcattca | ggacacttta | ttctgctatt | ggcattgacc | 660 |
| tggcatctca | tgggtttata | gttgctgctg | tagaacacag | agatagatct | gcatctgcaa | 720 |
| cttactattt | caaggaccaa | tctgctgcag | aaatagggga | caagtcttgg | ctctacctta | 780 |
| gaaccctgaa | acaagaggag | gagacacata | tacgaaatga | gcaggtacgg | caaagagcaa | 840 |
| aagaatgttc | ccaagctctc | agtctgattc | ttgacattga | tcatgaaag | ccagtgaaga | 900 |
| atgcattaga | tttaaagttt | gatatggaac | aactgaagga | ctctattgat | agggaaaaaa | 960 |
| tagcagtaat | tggacattct | tttggtggag | caacggttat | tcagactctt | agtgaagatc | 1020 |
| agagattcag | atgtggtatt | gccctggatg | catggatgtt | tccactgggt | gatgaagtat | 1080 |
| attccagaat | tcctcagccc | ctcttttta | tcaactctga | atatttccaa | tatcctgcta | 1140 |
| atatcataaa | aatgaaaaaa | tgctactcac | ctgataaaga | aagaaagatg | attacaatca | 1200 |
| ggggttcagt | ccaccagaat | tttgctgact | tcacttttgc | aactggcaaa | ataattggac | 1260 |
| acatgctcaa | attaaaggga | gacatagatt | caaatgtagc | tattgatctt | agcaacaaag | 1320 |
| cttcattagc | attcttacaa | aagcatttag | gacttcataa | agattttgat | cagtgggact | 1380 |
| gcttgattga | aggagatgat | gagaatctta | ttccagggac | caacattaac | acaaccaatc | 1440 |
| aacacatcat | gttacagaac | tcttcaggaa | tagagaaata | caattaggat | taaaataggt | 1500 |
| ttttt | | | | | | 1505 |

<210> SEQ ID NO 2
<211> LENGTH: 1561
<212> TYPE: DNA
<213> ORGANISM: Homo sapiens

<400> SEQUENCE: 2

| | | | | | |
|---|---|---|---|---|---|
| cgcacgccac | ccgcccgccg | cctgccagag | ctgctcggcc | cgcagccagg | gggacagcgg | 60 |
| ctggtcggag | gctcgcagtg | ctgtcggcga | gaagcagtcg | ggtttggagc | gcttgggtcg | 120 |
| cgttggtgcg | cggtggacac | gagggacccc | agttcccgcg | agcagctccg | cgccggccct | 180 |
| gagagactaa | gctgaaactg | ctgctcagct | cccaagatgg | tgccacccaa | attgcatgtg | 240 |
| cttttctgcc | tctgcggctg | cctggctgtg | gtttatcctt | ttgactggca | atacataaat | 300 |

-continued

```
cctgttgccc atatgaaatc atcagcatgg gtcaacaaaa tacaagtact gatggctgct    360
gcaagctttg gccaaactaa atccccccgg ggaaatgggc cttattccgt tggttgtaca    420
gacttaatgt ttgatcacac taataagggc accttcttgc gtttatatta tccatcccaa    480
gataatgatc gccttgacac cctttggatc ccaaataaag aatattttg gggtcttagc     540 aaatttcttg gaacacactg gcttatgggc aacattttga ggttactctt tggttcaatg    600
acaactcctg caaactggaa ttcccctctg aggcctggtg aaaaatatcc acttgttgtt    660
ttttctcatg gtcttggggc attcaggaca ctttattctg ctattggcat tgacctggca    720
tctcatgggt ttatagttgc tgctgtagaa cacagagata gatctgcatc tgcaacttac    780
tatttcaagg accaatctgc tgcagaaata ggggacaagt cttggctcta ccttagaacc    840
ctgaaacaag aggaggagac acatatacga aatgagcagg tacggcaaag agcaaaagaa    900
tgttcccaag ctctcagtct gattcttgac attgatcatg gaaagccagt gaagaatgca    960
ttagatttaa agtttgatat ggaacaactg aaggactcta ttgataggga aaaaatagca    1020
gtaattggac attcttttgg tggagcaacg gttattcaga ctcttagtga agatcagaga    1080
ttcagatgtg gtattgccct ggatgcatgg atgtttccac tgggtgatga agtatattcc    1140
agaattcctc agcccctctt ttttatcaac tctgaatatt tccaatatcc tgctaatatc    1200
ataaaaatga aaaatgcta ctcacctgat aaagaaagaa agatgattac aatcaggggt     1260
tcagtccacc agaattttgc tgacttcact tttgcaactg gcaaataat tggacacatg     1320 ctcaaattaa agggagacat agattcaaat gcagctattg atcttagcaa caaagcttca    1380
ttagcattct tacaaaagca tttaggactt cataaagatt ttgatcagtg ggactgcttg    1440
attgaaggag atgatgagaa tcttattcca gggaccaaca ttaacacaac caatcaacac    1500
atcatgttac agaactcttc aggaatagag aaatacaatt aggattaaaa taggtttttt    1560
a                                                                   1561
```

<210> SEQ ID NO 3
<211> LENGTH: 441
<212> TYPE: PRT
<213> ORGANISM: Homo sapiens

<400> SEQUENCE: 3

```
Met Val Pro Pro Lys Leu His Val Leu Phe Cys Leu Cys Gly Cys Leu
  1               5                  10                  15

Ala Val Val Tyr Pro Phe Asp Trp Gln Tyr Ile Asn Pro Val Ala His
             20                  25                  30

Met Lys Ser Ser Ala Trp Val Asn Lys Ile Gln Val Leu Met Ala Ala
         35                  40                  45

Ala Ser Phe Gly Gln Thr Lys Ile Pro Arg Gly Asn Gly Pro Tyr Ser
     50                  55                  60

Val Gly Cys Thr Asp Leu Met Phe Asp His Thr Asn Lys Gly Thr Phe
 65                  70                  75                  80

Leu Arg Leu Tyr Tyr Pro Ser Gln Asp Asn Asp Arg Leu Asp Thr Leu
                 85                  90                  95

Trp Ile Pro Asn Lys Glu Tyr Phe Trp Gly Leu Ser Lys Phe Leu Gly
            100                 105                 110

Thr His Trp Leu Met Gly Asn Ile Leu Arg Leu Leu Phe Gly Ser Met
        115                 120                 125

Thr Thr Pro Ala Asn Trp Asn Ser Pro Leu Arg Pro Gly Glu Lys Tyr
    130                 135                 140
```

```
Pro Leu Val Val Phe Ser His Gly Leu Gly Ala Phe Arg Thr Leu Tyr
145                 150                 155                 160

Ser Ala Ile Gly Ile Asp Leu Ala Ser His Gly Phe Ile Val Ala Ala
            165                 170                 175

Val Glu His Arg Asp Arg Ser Ala Ser Ala Thr Tyr Tyr Phe Lys Asp
        180                 185                 190

Gln Ser Ala Ala Glu Ile Gly Asp Lys Ser Trp Leu Tyr Leu Arg Thr
        195                 200                 205

Leu Lys Gln Glu Glu Thr His Ile Arg Asn Glu Gln Val Arg Gln
210                 215                 220

Arg Ala Lys Glu Cys Ser Gln Ala Leu Ser Leu Ile Leu Asp Ile Asp
225                 230                 235                 240

His Gly Lys Pro Val Lys Asn Ala Leu Asp Leu Lys Phe Asp Met Glu
                245                 250                 255

Gln Leu Lys Asp Ser Ile Asp Arg Glu Lys Ile Ala Val Ile Gly His
            260                 265                 270

Ser Phe Gly Gly Ala Thr Val Ile Gln Thr Leu Ser Glu Asp Gln Arg
        275                 280                 285

Phe Arg Cys Gly Ile Ala Leu Asp Ala Trp Met Phe Pro Leu Gly Asp
290                 295                 300

Glu Val Tyr Ser Arg Ile Pro Gln Pro Leu Phe Phe Ile Asn Ser Glu
305                 310                 315                 320

Tyr Phe Gln Tyr Pro Ala Asn Ile Ile Lys Met Lys Lys Cys Tyr Ser
                325                 330                 335

Pro Asp Lys Glu Arg Lys Met Ile Thr Ile Arg Gly Ser Val His Gln
            340                 345                 350

Asn Phe Ala Asp Phe Thr Phe Ala Thr Gly Lys Ile Ile Gly His Met
        355                 360                 365

Leu Lys Leu Lys Gly Asp Ile Asp Ser Asn Ala Ala Ile Asp Leu Ser
370                 375                 380

Asn Lys Ala Ser Leu Ala Phe Leu Gln Lys His Leu Gly Leu His Lys
385                 390                 395                 400

Asp Phe Asp Gln Trp Asp Cys Leu Ile Glu Gly Asp Asp Glu Asn Leu
                405                 410                 415

Ile Pro Gly Thr Asn Ile Asn Thr Thr Asn Gln His Ile Met Leu Gln
            420                 425                 430

Asn Ser Ser Gly Ile Glu Lys Tyr Asn
        435                 440
```

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<221> NAME/KEY: modified_base
<222> LOCATION: (3)..(21)
<223> OTHER INFORMATION: a, c, g, t, unknown or other

<400> SEQUENCE: 4
aannnnnnnn nnnnnnnnnn ntt                                    23

<210> SEQ ID NO 5
<211> LENGTH: 5
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 5

Gly Gly Gly Gly Cys
 1               5
```

METHODS OF TREATMENT AND PREVENTION OF METABOLIC BONE DISEASES AND DISORDERS

CROSS REFERENCE TO RELATED APPLICATIONS

This application claims benefit under 35 U.S.C. §119(e) of U.S. provisional application No. 60/928,921 filed May 11, 2007, the contents of which are incorporated herein by reference in its entirety.

FIELD OF THE INVENTION

The present invention relates generally to methods for the treatment and/or prevention of metabolic bone disease or disorders, and more particularly to treatment and/or prevention of metabolic bone diseases or disorders associated with loss of bone mass and density, such as osteoporosis and osteopenic diseases using agents that inhibit the expression and/or activity of Lp-PLA$_2$ protein.

BACKGROUND OF THE INVENTION

Lipoprotein-Associated Phospholipase A2 (Lp-PLA$_2$), also previously known in the art as Platelet Activating Factor Acetly Hydrolase (PAF acetyl hydrolase) is a member of the super family of phospholipase A2 enzymes that are involved in hydrolysis of lipoprotein lipids or phospholipids. It is secreted by several cells that play a major role in the systemic inflammatory response to injury, including lymphocytes, monocytes, macrophage, T Lymphocytes and mast cells.

During the conversion of LDL to its oxidised form, Lp-PLA$_2$ is responsible for hydrolysing the sn-2 ester of oxidatively modified phosphatidylcholine to give lyso-phosphatidylcholine and an oxidatively modified fatty acid. Lp-PLA$_2$ hydrolyzes the sn2 position of a truncated phospholipid associated with oxidized LDL. As a result, there is a generation of 2 inflammatory cell homing mediators (non-esterfied fatty acids (NEFA) and LYSO PC) Both NEFA and LYSO PCs are chematractants for circulating monocytes, play a role in the activation of macrophages and increase oxidative stress as well as affecting the functional and the immediate responses of T lymphocytes. Lp-PLA$_2$ is bound in humans and pigs to the LDL molecule via lipoprotein B, and once in the arterial wall the oxidized LDL is susceptible to hydrolysis by Lp-PLA$_2$.

Both of these products of Lp-PLA$_2$ action are potent chemoattractants for circulating monocytes. As such, this enzyme is thought to be responsible for the accumulation of cells loaded with cholesterol ester in the arteries, causing the characteristic 'fatty streak' associated with the early stages of atherosclerosis, and inhibition of the Lp-PLA$_2$ enzyme may be useful in preventing the build up of this fatty streak (by inhibition of the formation of lysophosphatidylcholine), and useful in the treatment of atherosclerosis.

In addition, it is proposed that Lp-PLA$_2$ plays a direct role in LDL oxidation. This is due to the poly unsaturated fatty acid-derived lipid peroxide products of Lp-PLA$_2$ action contributing to and enhancing the overall oxidative process. In keeping with this idea, Lp-PLA$_2$ inhibitors inhibit LDL oxidation. Lp-PLA$_2$ inhibitors may therefore have a general application in any disorder that involves lipid peroxidation in conjunction with the enzyme activity, for example in addition to conditions such as atherosclerosis and diabetes other conditions such as rheumatoid arthritis, myocardial infarction and reperfusion injury.

Lp-PLA$_2$ is responsible for hydrolysing the sn-2 ester of oxidatively modified phosphatidylcholine to give lyso-phosphatidylcholine (lysoPC) and an oxidatively modified fatty acid. Both of these products of Lp-PLA$_2$ action are potent chemoattractants for circulating monocytes. Therefore, Lp-PLA$_2$ is thought to be responsible for the accumulation of cells loaded with cholesterol ester in the arteries, characteristic of atherosclerosis.

Osteopenia and osteoporosis are characterized by low bone mass and structural deterioration of bone tissue, leading to bone fragility and an increased susceptibility to fractures. Osteoporosis affects 44 million Americans, or 55 percent of the people 50 years of age and older. One in two women and one in four men over age 50 will have an osteoporosis-related fracture in her/his remaining lifetime. Osteopenia and osteoporosis are responsible for more than 1.5 million fractures annually. The estimated national direct expenditures (hospitals and nursing homes) for osteoporotic hip fractures were $18 billion dollars in 2002, and the cost is rapidly rising.

One approach, for example, for treating bone disorders is inhibition of the osteoclast proton pump. See e.g., Blair et al., Science 1989, 245, 855-857; Finbow et al., Biochem. J. 1997, 324, 697-712; Forgac, M. Soc. Gen. Physiol. Ser. 1996, 51, 121-132; Baron et al., J. Cell. Biol. 1985, 101, 2210-2222; Farina et al., Exp. Opin. Ther. Patents 1999, 9, 157-168; and David, P. and Baron, R. "The Vacuolar II$^+$TPase: A Potential Target for Drug Development in Bone Diseases" Exp. Opin. Invest. Drugs 1995, 4, 725-740.

Another approach to drug discovery for treating bone-related (and other) diseases involves the control of cellular signal transduction. See, for example, Missbach et al., "A Novel Inhibitor of the Tyrosine Kinase Src Suppresses Phosphorylation of Its Major Cellular Substrates and Reduces Bone Resorption in Vitro and in Rodent Models In Vivo." Bone 1999, 24, 437-449; Connolly et al., Bioorg. & Med. Chem. Lett. 1997, 7, 2415-2420; Trump-Kallmeyer et al., J. Med. Chem. 1998, 41, 1752-1763; Klutchko et al., J. Med. Chem. 1998, 41, 3276-3292; Legraverend et al., Bioorg. & Med. Chem. 1999, 7, 1281-1293; Chang et al., Chem. & Biol. 1999, 6, 361-375; Lev et al. Nature 1995, 376, 737-784; Palmer et al., J. Med. Chem. 1997, 40, 1519-1529.

Some approaches for the treatment of bone disorders such as osteoporosis include, for example, estrogens, bisphosphonates, calcitonin, flavonoids, and selective estrogen receptor modulators. Other approaches include peptides from the parathyroid hormone family, strontium ranelate, and growth hormone and insulin-like growth response (see, for example, Reginster et al. "Promising New Agents in Osteoporosis," Drugs R & D 1999, 3, 195-201).

The variety of different approaches represented by the therapeutic agents currently available or under study evidence the variety of biological factors influencing the competing processes of bone production and resorption. Although progress has been made towards developing therapeutic agents for osteoporosis and other bone disorders, to date, there is no cure for osteopenia and osteoporosis. Current medication for osteopenia and osteoporosis is aimed at reducing fracture risk and alleviating symptoms related to fracture.

SUMMARY OF THE INVENTION

The present invention relates to methods for treating and preventing metabolic bone diseases and disorders by inhibiting Lp-PLA$_2$, including inhibiting the expression and/or activity of Lp-PLA$_2$. Metabolic bone diseases and disorders amenable to treatment and/or prevention by the methods of the present invention are diseases and disorders associated with loss of bone mass and density and include but are not limited osteoporosis and osteopenic related diseases. Osteoporosis and osteopenic related diseases include but are not limited to Paget's diseases, hyperparathyroidism and related diseases.

In one embodiment, the methods as disclosed herein comprise administering to a patient in need thereof for treating or preventing a metabolic bone disease, a pharmaceutical composition comprising an effective amount of an agent which inhibits Lp-PLA$_2$, for example an agent which inhibits the expression of Lp-PLA$_2$ and/or the activity of Lp-PLA$_2$ protein. It is not intended that the present invention to be limited to any particular stage of the disease (e.g. early or advanced).

In some embodiments as disclosed herein methods to prevent osteoporosis and/or osteopenic diseases are effected by inhibiting the expression of Lp-PLA$_2$ and/or inhibiting the protein activity of Lp-PLA$_2$. Accordingly some embodiments provide methods for inhibiting Lp-PLA$_2$ by blocking enzyme activity and some embodiments provide methods for inhibiting Lp-PLA$_2$ by reducing and/or downregulating the expression of Lp-PLA$_2$ RNA. In some embodiments preventing and/or reducing loss of bone mass and/or loss of bone density leads to preventing or reducing symptoms associated with metabolic bone diseases or disorders such as osteoporosis and/or osteopenic diseases.

In one aspect the methods as disclosed herein provide methods of treating and/or preventing a metabolic bone disorder or disease in a patient, such as a human patient, wherein the methods comprise administering to the patient in need thereof a pharmaceutical composition comprising an effective amount of an agent that inhibits the activity and/or expression of the Lp-PLA$_2$ protein. Such a metabolic bone disease or disorder includes metabolic bone diseases and disorders associated with loss of bone mass and/or loss of bone density. Such metabolic bone diseases include but are not limited to osteoporosis and osteopenic related diseases such as diseases with bone marrow abnormalities. These include, including dyslipidemia, type II diseases, metabolic syndrome, insulin resistance, Paget's disease, hyperparathyroidism and related diseases. In a further embodiment, the patient administered an effective amount of an agent that inhibits the activity or expression of the Lp-PLA$_2$ protein is a human.

The method of this invention can be effected by administering an effective amount of a reversible or irreversible Lp-PLA$_2$ inhibitor. Examples of reversible inhibitors are small molecules and compounds such as 1-(N-(2-(diethylamino)ethyl)-N-(4-(4-trifluoromethylphenyl)benzyl)-aminocarbonylmethyl)-2-(4-fluorobenzyl)thio-5,6-trimethylenepyrimidin-4-one (which is also known as SB480848). N-(2-diethylaminoethyl)-2-[2-(2-(2,3-difluorophenyl)ethyl)-4-oxo-4,5,6,7-tetrahydro-cyclopentapyrimidin-1-yl]-N-(4'-trifluoromethyl-biphenyl-4-ylmethyl)acetamide, N-(1-(2-Methoxyethyl)piperidin-4-yl)-2-[2-(2,3-difluorobenzylthio)-4-oxo-4H-quinolin-1-yl]-N-(4'-trifluoromethylbiphenyl-4-ylmethyl)acetamide, methyl 2-[4-({[2-[2-(2,3-difluorophenyl)ethyl]-4-oxopyrido[2,3-d]pyrimidin-1(4H)-yl]acetyl}{[4'-(trifluoromethyl)-4-biphenylyl]methyl}amino)-1-piperidinyl]-2-methylpropanoate, or a salt thereof.

Also, the method of this invention comprises identifying a patient at risk for developing a clinical degree of a metabolic bone disease such as osteopenia or having a clinical degree of osteopenia and, for those at risk or having such a condition, administering an effective amount of an Lp-PLA$_2$ inhibitor to those in need thereof, and, optionally, monitoring the effectiveness of the treatment. Bone density and biomarkers can be used to identify patients who could benefit from the therapy as disclosed herein.

The methods can further comprise administering additional therapeutic agents used in the treatment of metabolic bone diseases. For example, where the metabolic bone disorder is osteoporosis one can treat the patient with the likes of bisphosphates such as alendronate, ibandronate, risedronate, calcitonin, raloxifene, a selective estrogen modulator (SERM), estrogen therapy, hormone replacement therapy (ET/HRT) and teriparatide.

BRIEF DESCRIPTION OF FIGURES

FIG. 4 shows representative images of examples from n=4 animals per group.

FIG. 7 shows representative images of examples from n=4 animals per group.

FIG. 9 shows MLO-A5 cells treated with 5 µM LysoPC after 7 days show reduced alkaline phosphatase staining.

DETAILED DESCRIPTION

Figure 1:
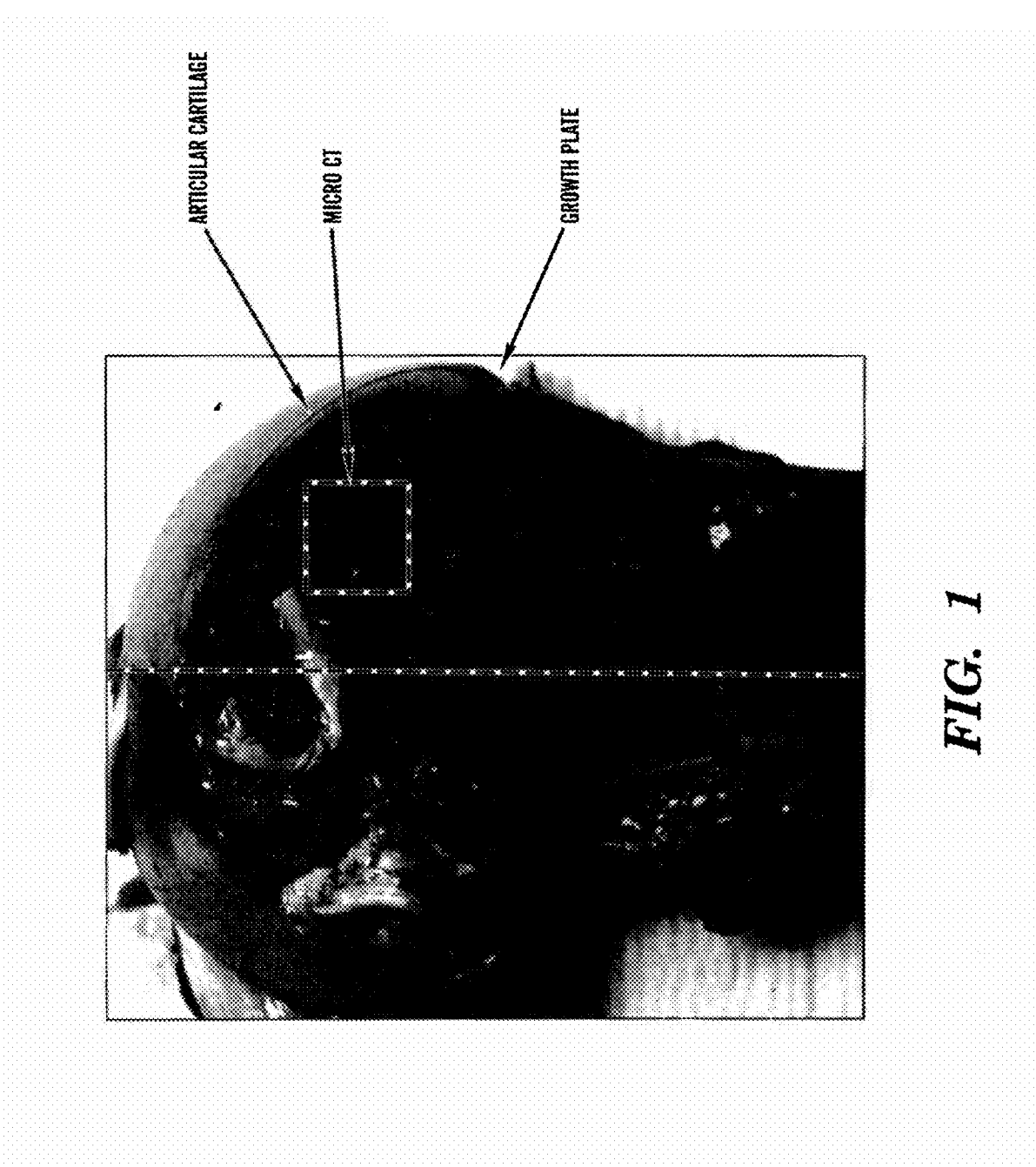
FIG. 1 shows the region of medial femoral condyle scanned and analyzed by micro CT. Bold dashed line represents cut plane. Area to the right indicates wedge of medial femoral condyle scanned. Dotted line box indicates approximate area of analysis.

The inventors have discovered that animals prone to pathological features of metabolic bone diseases exhibit reduced loss of bone density and bone mass when treated with an Lp-PLA$_2$ inhibitor. Animals treated with an Lp-PLA$_2$ inhibitor showed increased bone density and reduced death of osteocytes and osteoblasts as compared to animals not treated with the Lp-PLA$_2$ inhibitor. The animals treated with an Lp-PLA$_2$ inhibitor also had normal trabecular bone marrow as compared to animals not treated with the Lp-PLA$_2$ inhibitor. The latter showed trabecular bone marrow abnormalities such as increased extracellular material, reduced cellularity and shrinkage of adipocytes, demonstrating pathological signs of abnormal bone marrow homeostasis. Therefore, the inventors have discovered that Lp-PLA$_2$ inhibitors can be used in treating or preventing metabolic bone diseases and disorders, particularly metabolic bone diseases and disorders associated with loss of bone mass and/or loss of bone density. Such metabolic bone diseases include osteoporosis and osteopenic related diseases caused by or associated with dyslipidemia, type II diseases, metabolic syndrome, insulin resistance, Paget's disease, and hyperparathyroidism and related diseases.

Definitions

For convenience, certain terms employed in the entire application (including the specification, examples, and appended claims) are collected here. Unless defined otherwise, all technical and scientific terms used herein have the same meaning as commonly understood by one of ordinary skill in the art to which this invention belongs.

The term "metabolic bone disease" as used herein refers to a varied assortment of bone diseases and disorders characterized by gradual and progressive loss of bone tissue. Metabolic bone diseases amenable to prevention and/or treatment using the methods as described herein are metabolic bone diseases whereby there is a condition of diffusely decreased bone density and/or diminished bone strength. Such diseases are characterized by histological appearance. Two examples are osteoporosis which is a common metabolic bone disorder characterized by decreased mineral and bone matrix, and osteomalacia which is characterized by decreased mineral but intact bone matrix.

The term "osteopenic diseases" or "osteopenia" are used interchangeably herein, and refer to conditions with decreased calcification and/or bone density, and is a descriptive term used to refer to all skeletal systems in which the condition is noted. Osteopenia also refers to a reduced bone mass due to inadequate osteoid synthesis.

The term "osteoporosis" refers to conditions in which decreased mineral or bone matrix and reduced bone mass occurs.

The term "disease" or "disorder" is used interchangeably herein, and refers to any alteration in state of the body or of some of the organs, interrupting or disturbing the performance of the functions and/or causing symptoms such as discomfort, dysfunction, distress, or even death to the person afflicted or those in contact with a person. A disease or disorder can also relate to a distemper, ailing, ailment, malady, disorder, sickness, illness, complaint, inderdisposition or affectation.

The term "abnormalities in bone marrow" or "abnormal bone marrow" is used to refer to a dysfunctional or abnormal morphological characteristic of bone marrow, for example where the bone marrow comprises loss or death of osteocytes and/or osteoblasts, resulting in, for example fast bone turn over or reduced bone formation. Abnormal bone marrow can also be used to refer to presence of cells or structures not typically present in normal bone marrow, and/or altered morphology of cells present in the bone marrow, for example presence of increased extracellular material, or altered morphology of adipocytes or reduced numbers of cells present in the bone marrow. Bone marrow abnormalities referred to herein are defined as those where general abnormalities of the biological balance in the bone marrow is indicated, for example, including but not limited to viral or bacterial infections in the bone marrow, cellular infiltration of the bone marrow, abnormalities of the bone marrow haematopoiesis, proliferation of malignant neoplasms in the bone marrow and concentration changes in cell growth differentiation factors.

The term "agent" refers to any entity which is normally not present or not present at the levels being administered in the cell. Agent can be selected from a group comprising: chemicals; small molecules; nucleic acid sequences; nucleic acid analogues; proteins; peptides; aptamers; antibodies; or fragments thereof. A nucleic acid sequence can be RNA or DNA, and can be single or double stranded, and can be selected from a group comprising; nucleic acid encoding a protein of interest, oligonucleotides, nucleic acid analogues, for example peptide-nucleic acid (PNA), pseudo-complementary PNA (pc-PNA), locked nucleic acid (LNA) etc. Such nucleic acid sequences include, for example, but are not limited to, nucleic acid sequence encoding proteins, for example that act as transcriptional repressors, antisense molecules, ribosomes, small inhibitory nucleic acid sequences, for example but are not limited to RNAi, shRNAi, siRNA, micro RNAi (mRNAi), antisense oligonucleotides etc. A protein and/or peptide or fragment thereof can be any protein of interest, for example, but are not limited to: mutated proteins; therapeutic proteins and truncated proteins, wherein the protein is normally absent or expressed at lower levels in the cell. Proteins can also be selected from a group comprising; mutated proteins, genetically engineered proteins, peptides, synthetic peptides, recombinant proteins, chimeric proteins, antibodies, midibodies, minibodies, triabodies, humanized proteins, humanized antibodies, chimeric antibodies, modified proteins and fragments thereof. Alternatively, the agent can be intracellular within the cell as a result of introduction of a nucleic acid sequence into the cell and its transcription resulting in the production of the nucleic acid and/or protein inhibitor of Lp-PLA$_2$ within the cell. In some embodiments, the agent is any chemical, entity or moiety, including without limitation synthetic and naturally-occurring non-proteinaceous entities. The agents of particular interest are small molecules that reversibly or irreversibly inhibit Lp-PLA$_2$. These include unsubstituted or substituted alkyl, aromatic, or heterocyclyl compounds as further illustrated below.

The term "inhibiting" as used herein means that the expression or activity of Lp-PLA$_2$ or variants or homologues thereof is reduced to an extent, and/or for a time, sufficient to produce the desired effect. The reduction in activity can be due to affecting one or more characteristics of Lp-PLA$_2$ including decreasing its catalytic activity or by inhibiting a co-factor of Lp-PLA$_2$ or by binding to Lp-PLA$_2$ with a degree of avidity that is such that the outcome is that of treating or preventing a metabolic bond disorder. In particular, inhibition of Lp-PLA$_2$ can be determined using an assay for Lp-PLA$_2$ inhibition by using the bioassay for Lp-PLA$_2$ protein as disclosed herein.

As used herein, the term "Lp-PLA$_2$" refers to the protein target to be inhibited by the methods as disclosed herein. Lp-PLA$_2$ is used interchangeably with lipoprotein associated phospholipase A$_2$, also previously known in the art as Platelet Activating Factor Acetyl Hydrolase (PAF acetyl hydrolase). Human Lp-PLA$_2$ is encoded by nucleic acid corresponding to accession No: U20157 (SEQ ID NO:1) or Ref Seq ID: NM_005084 (SEQ ID NO:2) or and the human Lp-PLA$_2$ corresponds to protein sequence corresponding to accession No: NP_005075 (SEQ ID NO:3), which are disclosed in U.S. Pat. No. 5,981,252, which is specifically incorporated herein in its entirety by reference.

As used herein, "gene silencing" or "gene silenced" in reference to an activity of n RNAi molecule, for example a siRNA or miRNA refers to a decrease in the mRNA level in a cell for a target gene by at least about 5%, about 10%, about 20%, about 30%, about 40%, about 50%, about 60%, about 70%, about 80%, about 90%, about 95%, about 99%, about 100% of the mRNA level found in the cell without the presence of the miRNA or RNA interference molecule. In one preferred embodiment, the mRNA levels are decreased by at least about 70%, about 80%, about 90%, about 95%, about 99%, about 100%.

As used herein, the term "RNAi" refers to any type of interfering RNA, including but are not limited to, siRNAi, shRNAi, endogenous microRNA and artificial microRNA. For instance, it includes sequences previously identified as siRNA, regardless of the mechanism of down-stream processing of the RNA (i.e. although siRNAs are believed to have a specific method of in vivo processing resulting in the cleavage of mRNA, such sequences can be incorporated into the vectors in the context of the flanking sequences described herein).

As used herein an "siRNA" refers to a nucleic acid that forms a double stranded RNA, which double stranded RNA has the ability to reduce or inhibit expression of a gene or target gene when the siRNA is present or expressed in the same cell as the target gene, for example Lp-PLA$_2$. The double stranded RNA siRNA can be formed by the complementary strands. In one embodiment, a siRNA refers to a nucleic acid that can form a double stranded siRNA. The sequence of the siRNA can correspond to the full length target gene, or a subsequence thereof. Typically, the siRNA is at least about 15-50 nucleotides in length (e.g., each complementary sequence of the double stranded siRNA is about 15-50 nucleotides in length, and the double stranded siRNA is about 15-50 base pairs in length, preferably about 19-30 base nucleotides, preferably about 20-25 nucleotides in length, e.g., 20, 21, 22, 23, 24, 25, 26, 27, 28, 29, or 30 nucleotides in length).

As used herein "shRNA" or "small hairpin RNA" (also called stem loop) is a type of siRNA. In one embodiment, these shRNAs are composed of a short, e.g. about 19 to about 25 nucleotide, antisense strand, followed by a nucleotide loop of about 5 to about 9 nucleotides, and the analogous sense strand. Alternatively, the sense strand can precede the nucleotide loop structure and the antisense strand can follow.

The terms "microRNA" or "miRNA" are used interchangeably herein are endogenous RNAs, some of which are known to regulate the expression of protein-coding genes at the posttranscriptional level. Endogenous microRNA are small RNAs naturally present in the genome which are capable of modulating the productive utilization of mRNA. The term artificial microRNA includes any type of RNA sequence, other than endogenous microRNA, which is capable of modulating the productive utilization of mRNA. MicroRNA sequences have been described in publications such as Lim, et al., Genes & Development, 17, p. 991-1008 (2003), Lim et al Science 299, 1540 (2003), Lee and Ambros Science, 294, 862 (2001), Lau et al., Science 294, 858-861 (2001), Lagos-Quintana et al, Current Biology, 12, 735-739 (2002), Lagos Quintana et al, Science 294, 853-857 (2001), and Lagos-Quintana et al, RNA, 9, 175-179 (2003), which are incorporated by reference. Multiple microRNAs can also be incorporated into a precursor molecule. Furthermore, miRNA-like stem-loops can be expressed in cells as a vehicle to deliver artificial miRNAs and short interfering RNAs (siRNAs) for the purpose of modulating the expression of endogenous genes through the miRNA and or RNAi pathways.

As used herein, "double stranded RNA" or "dsRNA" refers to RNA molecules that are comprised of two strands. Double-stranded molecules include those comprised of a single RNA molecule that doubles back on itself to form a two-stranded structure. For example, the stem loop structure of the progenitor molecules from which the single-stranded miRNA is derived, called the pre-miRNA (Bartel et al. 2004. Cell 116: 281-297), comprises a dsRNA molecule.

The terms "patient", "subject" and "individual" are used interchangeably herein and refer to an animal, particularly a human, to whom treatment is provided.

The term "gene" used herein can be a genomic gene comprising transcriptional and/or translational regulatory sequences and/or a coding region and/or non-translated sequences (e.g., introns, 5'- and 3'-untranslated sequences and regulatory sequences). The coding region of a gene can be a nucleotide sequence coding for an amino acid sequence or a functional RNA, such as tRNA, rRNA, catalytic RNA, siRNA, miRNA and antisense RNA. A gene can also be an mRNA or cDNA corresponding to the coding regions (e.g. exons and miRNA) optionally comprising 5'- or 3' untranslated sequences linked thereto. A gene can also be an amplified nucleic acid molecule produced in vitro comprising all or a part of the coding region and/or 5'- or 3'-untranslated sequences linked thereto.

The term "nucleic acid" or "oligonucleotide" or "polynucleotide" used herein can mean at least two nucleotides covalently linked together. As will be appreciated by those in the art, the depiction of a single strand also defines the sequence of the complementary strand. Thus, a nucleic acid also encompasses the complementary strand of a depicted single strand. As will also be appreciated by those in the art, many variants of a nucleic acid can be used for the same purpose as a given nucleic acid. Thus, a nucleic acid also encompasses substantially identical nucleic acids and complements thereof. As will also be appreciated by those in the art, a single strand provides a probe for a probe that can hybridize to the target sequence under stringent hybridization conditions. Thus, a nucleic acid also encompasses a probe that hybridizes under stringent hybridization conditions.

Nucleic acids can be single stranded or double stranded, or can contain portions of both double stranded and single stranded sequence. The nucleic acid can be DNA, both genomic and cDNA, RNA, or a hybrid, where the nucleic acid can contain combinations of deoxyribo- and ribo-nucleotides, and combinations of bases including uracil, adenine, thymine, cytosine, guanine, inosine, xanthine hypoxanthine, isocytosine and isoguanine. Nucleic acids can be obtained by chemical synthesis methods or by recombinant methods.

A nucleic acid will generally contain phosphodiester bonds, although nucleic acid analogs can be included that can have at least one different linkage, e.g., phosphoramidate, phosphorothioate, phosphorodithioate, or O-methylphosphoroamidite linkages and peptide nucleic acid backbones and linkages. Other analog nucleic acids include those with positive backbones; non-ionic backbones, and non-ribose backbones, including those described in U.S. Pat. Nos. 5,235,033 and 5,034,506, which are incorporated by reference. Nucleic acids containing one or more non-naturally occurring or modified nucleotides are also included within one definition of nucleic acids. The modified nucleotide analog can be located for example at the 5'-end and/or the 3'-end of the nucleic acid molecule. Representative examples of nucleotide analogs can be selected from sugar- or backbone-modified ribonucleotides. It should be noted, however, that also nucleobase-modified ribonucleotides, i.e. ribonucleotides, containing a non naturally occurring nucleobase instead of a naturally occurring nucleobase such as uridines or cytidines modified at the 5-position, e.g. 5-(2-amino)propyl uridine, 5-bromo uridine; adenosines and guanosines modified at the 8-position, e.g. 8-bromo guanosine; deaza nucleotides, e.g. 7 deaza-adenosine; O- and N-alkylated nucleotides, e.g. N6-methyl adenosine are suitable. The 2' OH— group can be replaced by a group selected from H. OR, R. halo, SH, SR, $NH_2$, NHR, NR2 or CN, wherein R is C-C6 alkyl, alkenyl or alkynyl and halo is F, Cl, Br or I. Modifications of the ribose-phosphate backbone can be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs can be made.

The term "vector" used herein refers to a nucleic acid sequence containing an origin of replication. A vector can be a plasmid, bacteriophage, bacterial artificial chromosome or yeast artificial chromosome. A vector can be a DNA or RNA vector. A vector can be either a self replicating extrachromosomal vector or a vector which integrate into a host genome.

As used herein, the term "treating" includes reducing or alleviating at least one adverse effect or symptom of a condition, disease or disorder associated with a metabolic bone disease or disorder such as osteoporosis and osteopenic related disorders. The term treating is used to refer to the reduction of a symptom and/or a biochemical marker of a metabolic bone disease or disorder by some useful amount, an amount that can be determined by one skilled in the art. "Treating" with regards to osteoporosis refers to a measurable reduction in a biochemical marker of osteoporosis, or a reduction in the death or loss of osteocytes and/or osteoblasts, i.e. such results would be considered effective treatments by the methods as disclosed herein. Alternatively, treating with regards to osteoporisis refers to a measurable increase in bone or bone matrix mineralization, such as a measurable increase in re-mineralization. As alternative examples, a reduction in a symptom such as a measurable slowing of the rate of decline of bone density or a measurable cessation of the rate bone density loss, or a measurable increase in bone density would also be considered as affective treatments by the methods as disclosed herein.

The term "effective amount" as used herein refers to the amount of agent that reduces or stops at least one symptom of the metabolic bone disease or disorder. An example of an effective amount would be considered as the amount sufficient to reduce a symptom of the disease or disorder by some measurable amount. One possible measure for treating or preventing osteoporosis or a metabolic bone disorder is a reduction in the measured parameter of at least about 10%. An effective amount as used herein would also include an amount sufficient to prevent or delay the development of a symptom of the disease, alter the course of a symptom of the disease or reverse a symptom of the disease.

The term "vectors" is used interchangeably with "plasmid" to refer to a nucleic acid molecule capable of transporting another nucleic acid to which it has been linked. Vectors capable of directing the expression of genes and/or nucleic acid sequence to which they are operatively linked are referred to herein as "expression vectors". In general, expression vectors of utility in recombinant DNA techniques are often in the form of "plasmids" which refer to circular double stranded DNA loops which, in their vector form are not bound to the chromosome. Other expression vectors can be used in different embodiments of the invention, for example, but are not limited to, plasmids, episomes, bacteriophages or viral vectors, and such vectors can integrate into the host's genome or replicate autonomously in the particular cell. Other forms of expression vectors known by those skilled in the art which serve the equivalent functions can also be used. Expression vectors comprise expression vectors for stable or transient expression encoding the DNA.

The articles "a" and "an" are used herein to refer to one or to more than one (i.e., to at least one) of the grammatical object of the article. By way of example, "an element" means one element or more than one element.

Lp-$PLA_2$: General Information

Lp-$PLA_2$ is also referred to in the art as aliases Lp-$PLA_2$, LDL-$PLA_2$, lipoprotein associated phospholipase $A_2$, $PLA_2G7$, phospholipase $A_2$ (group VII), or Platelet Activating Factor Acetyl Hydrolase (PAF acetyl hydrolase or PAFAH). Human Lp-$PLA_2$ is encoded by nucleic acid corresponding to GenBank Accession No: U20157 (SEQ ID NO:1) or Ref Seq ID: NM_005084 (SEQ ID NO:2) and the human Lp-$PLA_2$ corresponds to protein sequence corresponding to GenBank Accession No: NP_005075 (SEQ ID NO:3), which are disclosed in U.S. Pat. No. 5,981,252, which is specifically incorporated herein in its entirety by reference.

Phospholipase $A_2$ enzyme Lipoprotein Associated Phospholipase $A_2$ (Lp-$PLA_2$), the sequence, isolation and purification thereof, isolated nucleic acids encoding the enzyme, and recombinant host cells transformed with DNA encoding the enzyme are disclosed in WO 95/00649 (SmithKline Beecham plc), which is specifically incorporated herein in its entirety by reference. A subsequent publication from the same group further describes this enzyme (Tew D et al, Arterioscler Thromb Vas Biol 1996:16; 591-9) wherein it is referred to as LDL-$PLA_2$ and later patent application (WO 95/09921, Icos Corporation) and a related publication in Nature (Tjoelker et al, vol 374, 6 Apr. 1995, 549) describe the enzyme PAF-AH which has essentially the same sequence as Lp-$PLA_2$.

It has been shown that Lp-$PLA_2$ is responsible for the conversion of phosphatidylcholine to lysophosphatidylcholine, during the conversion of low density lipoprotein (LDL) to its oxidised form. The enzyme is known to hydrolyse the sn-2 ester of the oxidised phosphatidylcholine to give lysophosphatidylcholine and an oxidatively modified fatty acid. Both products of Lp-$PLA_2$ action are biologically active with lysophosphatidylcholine, in particular having several pro-atherogenic activities ascribed to it including monocyte chemotaxis and induction of endothelial dysfunction, both of which facilitate monocyte-derived macrophage accumulation within the artery wall.

The inventors have discovered that animals prone to disorders characterized by metabolic bone disorders have been found to exhibit normal or close to normal bone matrix normal bone density and normal bone marrow characteristics when treated with an Lp-PLA$_2$ inhibitor. Such animals treated with an inhibitor to Lp-PLA$_2$ also showed reduced signs of loss of osteoblasts and osteocytes, and reduced accumulation of bone marrow abnormalities as compared to animals not treated with the inhibitor. Therefore, Lp-PLA$_2$ inhibitors can be used to treat and/or prevent metabolic bone diseases and disorders such as osteoporosis and osteopenic related diseases bone marrow abnormalities and Paget's disease.

Agents that Inhibit Lp-PLA$_2$

The present invention relates to the inhibition of Lp-PLA$_2$. In some embodiments inhibition is inhibition of nucleic acid transcripts encoding Lp-PLA$_2$ such as by inhibition of messenger RNA (mRNA). In alternative embodiments, inhibition of Lp-PLA$_2$ is effected by the inhibition of the expression and/or inhibition of activity of the gene product of Lp-PLA$_2$, including the polypeptide or protein of Lp-PLA$_2$ or its isoforms. As used herein, the term "gene product" refers to RNA transcribed from a gene, or a polypeptide encoded by a gene or translated from RNA.

In some embodiments, inhibition of Lp-PLA$_2$ is by an agent such as nucleic acids, nucleic acid analogues, peptides, phage, phagemids, polypeptides, peptidomimetics, ribosomes, aptamers, antibodies, small or large organic or inorganic molecules, or any combination thereof. These agents include agents that function as inhibitors of Lp-PLA$_2$ expression, inhibitors of mRNA encoding Lp-PLA$_2$ being one example.

Agents useful in the methods as disclosed herein can also inhibit gene expression (i.e. suppress and/or repress the expression of the gene). Such agents are referred to in the art as "gene silencers" and are commonly known to those of ordinary skill in the art. Examples include a nucleic acid sequence, for an RNA, DNA or nucleic acid analogue, and can be single or double stranded, and can be selected from a group comprising nucleic acid encoding a protein of interest, oligonucleotides, nucleic acids, nucleic acid analogues such as peptide nucleic acid (PNA), pseudo-complementary PNA (pc-PNA), locked nucleic acids (LNA) and derivatives thereof etc. Nucleic acid agents also include, but are not limited to nucleic acid sequences encoding proteins that act as transcriptional repressors, antisense molecules, ribozymes, small inhibitory nucleic acid sequences, for example but are not limited to RNAi, shRNAi, siRNA, micro RNAi (miRNA), antisense oligonucleotides, etc.

As used herein, agents useful in the method as inhibitors of Lp-PLA$_2$ expression and/or inhibition of Lp-PLA$_2$ function can be any type of entity. These include small molecules nucleic acid sequences, nucleic acid analogues, proteins, peptides or fragments thereof.

Small Molecules

Particularly useful agents are small molecules such as small synthetic compounds that inhibit Lp-PLA$_2$. Irreversible or reversible inhibitors of Lp-PLA$_2$ can be used in the methods of the present invention.

Irreversible inhibitors of Lp-PLA$_2$ are disclosed in patent applications WO 96/13484, WO96/19451, WO 97/02242, WO97/217675, WO97/217676, WO 97/41098, and WO97/41099 (SmithKline Beecham plc) which are specifically incorporated in their entirety herein by reference and disclose inter alia various series of 4-thionyl/sulfinyl/sulfonyl azetidinone compounds which are inhibitors of the enzyme Lp-PLA$_2$. These are irreversible, acylating inhibitors (Tew et al, Biochemistry, 37, 10087, 1998).

Synthetic small molecule Lp-PLA$_2$ inhibitors effective in humans are commonly known by persons of ordinary skill and include those undergoing pre-clinical and clinical. A number of applications have been filed and published by SmithKline Beecham and its successor GlaxoSmithKline. A list of relevant published applications assigned to same is: WO01/60805, WO02/30904, WO03/016287, WO00/66567, WO03/042218, WO03/042206, WO03/042179, WO03/041712, WO03/086400, WO03/087088, WO02/30911, WO99/24420, WO00/66566, WO00/68208, WO00/10980, and WO2005/021002, which are specifically incorporated in their entirety herein by reference. In addition, reference is made to U.S. provisional applications 60/829,328 and 60/829,327, both having been filed 13 Oct. 2006, which are also specifically incorporated in their entirety herein by reference.

Other Lp-PLA$_2$ inhibitors useful in the methods as disclosed herein are described in published patent applications, for example WO2006063791-A1, WO2006063811-A1, WO2006063812-A1, WO2006063813-A1, all in the name of Bayer Healthcare; and US2006106017-A1 assigned to Korea Res. Inst. Bioscience & Biotechnology, which are specifically incorporated in their entirety herein by reference.

Lp-PLA$_2$ inhibitors encompassed for use in the methods as disclosed herein also include other compounds, such as statins and/or Niacin (see www.genengnews.com/news/bnitem.aspx?name=6724568) and fenofibrate (see www.genengnews.com/news/bnitem.aspx?name=14817756&taxid=19). Such Lp-PLA$_2$ agents can also be administered with the Lp-PLA$_2$ inhibitor agents as disclosed herein.

All of the applications set out in the above paragraphs are incorporated herein by reference. It is believed that any or all of the compounds disclosed in these documents are useful for prophylaxis or treatment of metabolic bone disorders including preventing or treating osteoporosis or osteopenic diseases.

The porcine model of decreased bone density as described herein below and exemplified in the Methods can be used by one of ordinary skill in the art to determine which of the disclosed compounds or other inhibitors of Lp-PLA$_2$, for example antibodies, or RNAi are effective for the treatment and/or prevention of metabolic bone diseases or disorders as claimed herein. In some embodiments, agents inhibiting Lp-PLA$_2$ can be assessed in animal models for effect on increasing bone density and/or bone mass. For example, one can use the porcine model of hyperglycemia and hypercholesterolemia as disclosed in the Examples herein, where the bone marrow is abnormal and having decreased bone density, for example the decreased bone matrix, in which the bone matrix can be assessed in the present and absence of inhibitors for Lp-PLA$_2$ by methods commonly known by persons in the art. In some embodiments, assessment of bone density and/or markers of metabolic bone diseases such as osteoporosis can be used, as disclosed herein.

In a particular embodiment, Lp-PLA$_2$ inhibitors as disclosed in U.S. Pat. Nos. 6,649,619 and 7,153,861, which are specifically incorporated in their entirety herein by reference (and International Application WO 01/60805) and U.S. Pat. No. 7,169,924 which is incorporated in its entirety herein by reference (and International Patent Application WO 02/30911), are useful in the methods disclosed herein for the prophylaxis or for the treatment of metabolic bone diseases or disorder such as osteoporosis or osteopenia. In some embodiments, the Lp-PLA$_2$ inhibitors as disclosed in U.S. publication No. 2005/0033052A1, which is incorporated in its entirety herein by reference, and International Patent Applications WO 02/30904, WO 03/042218, WO 03/042206, WO03/042179, WO 03/041712, WO 03/086400, and WO 03/87088 are reversible Lp-PLA$_2$ inhibitors, which are incorporated herein in their entirety by reference.

Formula (I) One can use a group of reversible Lp-PLA$_2$ inhibitors that are disclosed in international application WO 01/60805, from which arose U.S. Pat. Nos. 6,649,619 and 7,153,861 which are incorporated in their entirety herein by reference, the disclosures of which are incorporated herein in full, as though set out within this document. A narrower group of compounds of interest are those of formula (I) described in WO 01/60805 and claimed in U.S. Pat. Nos. 6,649,619 and 7,153,861, (which are incorporated herein in their entirety by reference) namely:

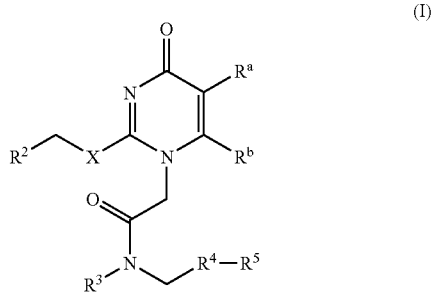

(I)

wherein:
R$^a$ and R$^b$ together with the pyrimidine ring carbon atoms to which they are attached form a fused 5-membered carbocyclic ring;
R$^2$ is phenyl, substituted by one to three fluorine atoms;
R$^3$ is methyl or C$_{(1-3)}$alkyl substituted by NR$^8$R$^9$; or
R$^3$ is Het-C$_{(0-2)}$alkyl in which Het is a 5- to 7-membered heterocyclyl ring having N and in which N is unsubstituted or substituted by C$_{(1-6)}$alkyl;
R$^4$ and R$^5$ together form a 4-(4-trifluoromethylphenyl)phenyl moiety;
R$^8$ and R$^9$ which can be the same or different are selected from the group consisting of hydrogen, or C$_{(1-6)}$alkyl);
X is S, or a pharmaceutically acceptable salt thereof.

Of even more interest are the following compounds, all within the scope of formula (I) and disclosed in the application and patents noted above:
1-(N-(2-(diethylamino)ethyl)-N-(4-(4-trifluoromethylphenyl)benzyl)-aminocarbonylmethyl)-2-(4-fluorobenzyl) thio-5,6-trimethylenepyrimidin-4-one, used in the pig study described herein;
1-(N-(2-(diethylamino)ethyl)-N-(4-(4-trifluoromethylphenyl)benzyl)-aminocarbonylmethyl)-2-(2,3-difluorobenzyl)thio-5,6-trimethylenepyrimidin-4-one;
1-(N-(2-(diethylamino)ethyl)-N-(4-(4-trifluoromethylphenyl)benzyl)amino-carbonylmethyl)-2-(3,4-difluorobenzyl)thio-5,6-trimethylenepyrimidin-4-one;
1-(N-(2-(diethylamino)ethyl)-N-(4-(4-trifluoromethylphenyl)benzyl)amino-carbonylmethyl)-2-(2,3,4-trifluorobenzyl)thio-5,6-trimethylenepyrimidin-4-one;
1-(N-(2-(diethylamino)ethyl)-N-(4-(4-trifluoromethylphenyl)benzyl)amino-carbonylmethyl)-2-(2-fluorobenzyl) thio-5,6-trimethylenepyrimidin-4-one;
1-(N-methyl-N-(4-(4-trifluoromethylphenyl)benzyl)aminocarbonylmethyl)-2-(4-fluorobenzyl)thio-5,6-trimethylenepyrimidin-4-one;
1-(N-(2-(1-piperidino)ethyl)-N-(4-(4-trifluoromethylphenyl)benzyl)aminocarbonylmethyl)-2-(4-fluorobenzyl) thio-5,6-trimethylenepyrimidin-4-one;
1-(N-(1-ethylpiperidin-4-yl)-N-(4-(4-trifluoromethylphenyl)benzyl)amino-carbonylmethyl)-2-(4-fluorobenzyl) thio-5,6-trimethylenepyrimidin-4-one;
1-(N-(2-ethylamino-2-methylpropyl)-N-(4-(4-trifluoromethylphenyl)benzyl)-aminocarbonylmethyl)-2-(4-fluorobenzyl)thio-5,6-trimethylenepyrimidin-4-one;
N-(2-tert-butylaminoethyl)-N-(4-(4-trifluoromethylphenyl) benzyl)amino-carbonylmethyl)-2-(4-fluorobenzyl)thio-5, 6-trimethylenepyrimidin-4-one;
1-(N-(1-methylpiperidin-4-yl)-N-(4-(4-trifluoromethylphenyl)benzyl)-aminocarbonylmethyl)-2-(4-fluorobenzyl) thio-5,6-trimethylenepyrimidin-4-one;
1-(N-(1-isopropylpiperidin-4-yl)-N-(4-(4-trifluoromethylphenyl)benzyl)-aminocarbonylmethyl)-2-(4-fluorobenzyl)thio-5,6-trimethylenepyrimidin-4-one;
1-(N-(1-(2-methoxyethyl)piperidin-4-yl)-N-(4-(4-trifluoromethylphenyl)benzyl)-aminocarbonylmethyl)-2-(4-fluorobenzyl)thio-5,6-trimethylenepyrimidin-4-one;
1-(N-(2-(ethylamino)ethyl)-N-(4-(4-trifluoromethylphenyl) benzyl)-aminocarbonylmethyl)-2-(4-fluorobenzyl)thio-5, 6-trimethylenepyrimidin-4-one; or a pharmaceutically acceptable salt of these compounds.

Methods for Preparing These Compounds are Disclosed in the Cited References and are Incorporated Herein by Reference.

A second process for making 1-(N-(2-(diethylamino) ethyl)-N-(4-(4-trifluoromethylphenyl)benzyl)-aminocarbonylmethyl)-2-(4-fluorobenzyl)thio-5,6-trimethylenepyrimidin-4-one can be found in application WO 03/016287 (U.S. publication No 20050014793A1), which is incorporated herein by reference in its entirety.

Formula (II)

A further group of compounds which can be useful in practicing the methods of this invention are disclosed in WO 02/30911; U.S. Pat. No. 7,169,924 corresponds to this international application. Both are incorporated herein in full. The generic formula in that case, represented here as formula (II), is as follows:

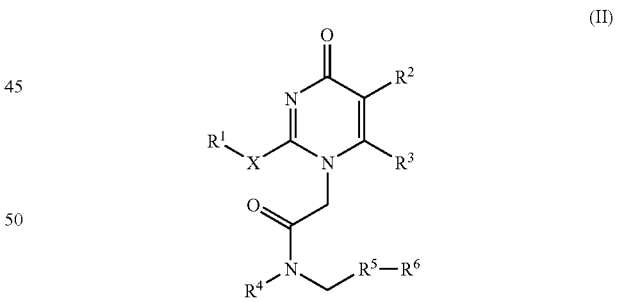

(II)

in which:
R$^1$ is an aryl group, optionally substituted by 1, 2, 3 or 4 substituents which can be the same or different selected from C$_{(1-6)}$alkyl, C$_{(1-6)}$alkoxy, C$_{(1-6)}$alkylthio, hydroxy, halogen, CN, and mono to perfluoro-C$_{(1-4)}$alkyl;
R$^2$ is halogen, C$_{(1-3)}$alkyl, C$_{(1-3)}$alkoxy, hydroxyC$_{(1-3)}$ alkyl, C$_{(1-3)}$alkylthio, C$_{(1-3)}$alkylsulphinyl, aminoC$_{(1-3)}$alkyl, mono- or di-C$_{(1-3)}$alkylaminoC$_{(1-3)}$alkyl, C$_{(1-3)}$alkylcarbonylaminoC$_{(1-3)}$alkyl, C$_{(1-3)}$alkoxyC$_{(1-3)}$alkylcarbonylamino C$_{(1-3)}$alkyl, C$_{(1-3)}$alkylsulphonylaminoC$_{(1-3)}$alkyl, C$_{(1-3)}$ alkylcarboxy, C$_{(1-3)}$alkylcarboxyC$_{(1-3)}$alkyl, and
R$^3$ is hydrogen, halogen, C$_{(1-3)}$alkyl, or hydroxyC$_{(1-3)}$ alkyl; or R² and R³ together with the pyrimidone ring carbon atoms to which they are attached form a fused 5- or 6-membered carbocyclic ring; or R² and R³ together with the pyrimidone ring carbon atoms to which they are attached form a fused benzo or heteroaryl ring optionally substituted by 1, 2, 3 or 4 substituents which can be the same or different selected from halogen, $C_{(1-4)}$alkyl, cyano, $C_{(1-6)}$alkoxy, $C_{(1-6)}$alkylthio or mono to perfluoro-$C_{(1-4)}$alkyl;

R⁴ is hydrogen, $C_{(1-6)}$alkyl which can be unsubstituted or substituted by 1, 2 or 3 substituents selected from hydroxy, halogen, OR⁷, COR⁷, carboxy, COOR⁷, CONR⁹R¹⁰, NR⁹R¹⁰, NR⁷COR⁸, mono- or di-(hydroxy$C_{(1-6)}$alkyl)amino and N-hydroxy$C_{(1-6)}$alkyl-N—$C_{(1-6)}$alkylamino; or R⁴ is Het-$C_{(0-4)}$alkyl in which Het is a 5- to 7-membered heterocyclyl ring comprising N and optionally O or S, and in which N can be substituted by COR⁷, COOR⁷, CONR⁹R¹⁰, or $C_{(1-6)}$alkyl optionally substituted by 1, 2 or 3 substituents selected from hydroxy, halogen, OR⁷, COR⁷, carboxy, COOR⁷, CONR⁹R¹⁰ or NR⁹R¹⁰, for instance, piperidin-4-yl, pyrrolidin-3-yl;

R⁵ is an aryl or a heteroaryl ring optionally substituted by 1, 2, 3 or 4 substituents which can be the same or different selected from $C_{(1-6)}$alkyl, $C_{(1-6)}$alkoxy, $C_{(1-6)}$alkylthio, aryl$C_{(1-6)}$alkoxy, hydroxy, halogen, CN, COR⁷, carboxy, COOR⁷, NR⁷COR⁸, CONR⁹R¹⁰, SO₂NR⁹R¹⁰, NR⁷SO₂R⁸, NR⁹R¹⁰, mono to perfluoro-$C_{(1-4)}$alkyl and mono to perfluoro-$C_{(1-4)}$alkoxy;

R⁶ is an aryl or a heteroaryl ring which is further optionally substituted by 1, 2, 3 or 4 substituents which can be the same or different selected from $C_{(1-8)}$alkyl, $C_{(1-8)}$alkoxy, $C_{(1-6)}$alkylthio, $C_{(1-6)}$alkylsulfonyl, aryl$C_{(1-6)}$alkoxy, hydroxy, halogen, CN, COR⁷, carboxy, COOR⁷, CONR⁹R¹⁰, NR⁷COR⁸, SO₂NR⁹R¹⁰, NR⁷SO₂R⁸, NR⁹R¹⁰, mono to perfluoro-$C_{(1-4)}$alkyl and mono to perfluoro-$C_{(1-4)}$alkoxy, or $C_{(5-10)}$alkyl;

R⁷ is hydrogen or $C_{(1-12)}$alkyl, for instance $C_{(1-4)}$alkyl (e.g. methyl or ethyl);

R⁸ is hydrogen, OC$_{(1-6)}$alkyl, or $C_{(1-12)}$alkyl, for instance $C_{(1-4)}$alkyl (e.g. methyl or ethyl);

R⁹ and R¹⁰ which can be the same or different is each selected from hydrogen, or $C_{(1-12)}$alkyl, or R⁹ and R¹⁰ together with the nitrogen to which they are attached form a 5- to 7 membered ring optionally containing one or more further heteroatoms selected from oxygen, nitrogen and sulphur, and optionally substituted by one or two substituents selected from hydroxy, oxo, $C_{(1-4)}$alkyl, $C_{(1-4)}$alkylcarboxy, aryl, e.g. phenyl, or aralkyl, e.g benzyl, for instance morpholine or piperazine; and X is $C_{(2-4)}$alkylene, optionally substituted by 1, 2 or 3 substituents selected from methyl and ethyl, or CH=CH.

All salts of formula (II), as well, can be used in the instant method of treatment.

Of particular interest are the compounds of formula (II) here, where, as noted in WO 02/30911 for formula (I) there, R¹ can be a phenyl group optionally substituted by 1, 2 or 3 or 4 substituents which can be the same or different selected from halo, $C_1$-$C_6$ alkyl, trifluoromethyl or $C_1$-$C_6$ alkoxy. More specifically, phenyl is unsubstituted or substituted by 1, 2, 3 or 4 halogen substituents, particularly, from 1 to 3 fluoro groups, and most particularly, 2,3-difluoro, 2,4-difluoro or 4-fluoro.

A further embodiment of formula (II) here, is where Y is —CH₂CH₂—.

In addition, of interest are compounds of formula (II) where R² is hydrogen, by default, or is halo, $C_1$-$C_6$ alkyl, mono to perfluoro-$C_1$-$C_4$ alkyl, mono to perfluoro $C_1$-$C_4$ alkoxy, or $C_1$-$C_6$ alkoxy; particularly mono to perfluoro-$C_1$-$C_4$ alkyl, mono to perfluoro-$C_1$-$C_4$ alkoxy, or $C_1$-$C_6$ alkoxy. Of particular interest are the compounds of formula (II) where R² is other than hydrogen, n in (R²)$_n$ is 1, 2, or 3, and the substitution pattern is meta and/or para, particularly para, i.e. a 4-position substituent. See also those compounds where R² is 4-trifluoromethyl or 4-trifluoromethoxy.

R³ and R⁴ can be the same or different and are methyl, ethyl, n-propyl, or n-butyl. Of particular interest are those compounds of formula (II) herein where R³ and R⁴ are the same and are methyl, or ethyl; methyl is of particular interest.

R⁵ can be hydrogen, $C_{(1-6)}$alkyl which is a straight chain, or branched. Of particular interest is methyl, ethyl, propyl, iso-propyl, n-butyl, sec-butyl, iso-butyl, t-butyl, n-pentyl or n-hexyl.

It will be appreciated that within the compounds of formula (II) herein there is a further sub-group of compounds in which:

R¹ is phenyl substituted by 2,3 difluoro;

R² and R³, together with the pyrimidine ring carbon atoms to which they are attached, form a fused 5-membered cyclopentenyl ring;

R⁴ is 2-(diethylamino)ethyl;

R⁵ is phenyl;

R⁶ is phenyl substituted by trifluoromethyl at the 4-position, or thien-2-yl substituted by trifluoromethyl in the 5-position; and X is (CH₂)₂.

Particular compounds of formula (II) herein of interest are:

N-(2-diethylaminoethyl)-2-[2-(2-(2,3-difluorophenyl)ethyl)-4-oxo-4,5,6,7-tetrahydro-cyclopentapyrimidin-1-yl]-N-(4'-trifluoromethyl-biphenyl-4-ylmethyl)acetamide;

N-(2-diethylaminoethyl)-2-[2-(2-(2,3-difluorophenyl)ethyl)-4-oxo-4,5,6,7-tetrahydro-cyclopentapyrimidin-1-yl]-N-(4'-trifluoromethyl-biphenyl-4-ylmethyl)acetamide bitartrate;

N-(2-ethylamino-2-methyl-propyl)-2-(2-(2-(2,3-difluorophenyl)-ethyl)-4-oxo-4,5,6,7-tetrahydro-cyclopentapyrimidin-1-yl)-N-(4'-trifluoromethyl-biphenyl-4-ylmethyl)-acetamide bitartrate;

N-(2-t-butylaminoethyl)-2-(2-(2-(2,3-difluorophenyl)-ethyl)-4-oxo-4,5,6,7-tetrahydro-cyclopentapyrimidin-1-yl)-N-(4'-trifluoromethyl-biphenyl-4-ylmethyl)acetamide bitartrate;

N-(1-ethyl-piperidin-4-yl)-2-(2-(2-(2,3-difluorophenyl)-ethyl)-4-oxo-4,5,6,7-tetrahydro-cyclopentapyrimidin-1-yl)-N-(4'-trifluoromethyl-biphenyl-4-ylmethyl)acetamide bitartrate;

N-(2-diethylaminoethyl)-2-(2-(2-(4-fluoro-2-(trifluoromethyl)phenyl)-ethyl)-4-oxo-4,5,6,7-tetrahydro-cyclopentapyrimidin-1-yl)-N-(4'-trifluoromethyl-biphenyl-4-ylmethyl)acetamide bitartrate;

N-(2-diethylaminoethyl)-2-(2-(2-(4-fluoro-3-(trifluoromethyl)phenyl)-ethyl)-4-oxo-4,5,6,7-tetrahydro-cyclopentapyrimidin-1-yl)-N-(4'-trifluoromethyl-biphenyl-4-ylmethyl)acetamide bitartrate;

N-(2-diethylaminoethyl)-2-(2-(2-(3-chloro-4-fluorophenyl)-ethyl)-4-oxo-4,5,6,7-tetrahydro-cyclopentapyrimidin-1-yl)-N-(4'-trifluoromethyl-biphenyl-4-ylmethyl)acetamide bitartrate;

(+/−)-N-(2-diethylaminoethyl)-2-(2-phenyl-propyl)-4-oxo-4,5,6,7-tetrahydro-cyclopentapyrimidin-1-yl)-N-(4'-trifluoromethyl-biphenyl-4-ylmethyl)acetamide bitartrate;

N-(2-diethylaminoethyl)-2-(2-(2-(2,4-difluorophenyl)-ethyl)-4-oxo-4,5,6,7-tetrahydro-cyclopentapyrimidin-1-yl)-N-(4'-trifluoromethyl-biphenyl-4-ylmethyl)acetamide bitartrate;

N-(2-diethylaminoethyl)-2-(2-(2-(2,5-difluorophenyl)-ethyl)-4-oxo-4,5,6,7-tetrahydro-cyclopentapyrimidin-1-yl)-N-(4'-trifluoromethyl-biphenyl-4-ylmethyl)acetamide bitartrate;

N-(2-diethylaminoethyl)-2-(2-(2-(3,4-difluorophenyl)-ethyl)-4-oxo-4,5,6,7-tetrahydro-cyclopentapyrimidin-1-yl)-N-(4'-trifluoromethyl-biphenyl-4-ylmethyl)acetamide;

N-(2-diethylaminoethyl)-2-(2-(2-(2-fluorophenyl)-ethyl)-4-oxo-4,5,6,7-tetrahydro-cyclopentapyrimidin-1-yl)-N-(4'-trifluoromethyl-biphenyl-4-ylmethyl)acetamide;

N-(2-diethylaminoethyl)-2-(2-(2-(3-fluorophenyl)-ethyl)-4-oxo-4,5,6,7-tetrahydro-cyclopentapyrimidin-1-yl)-N-(4'-trifluoromethyl-biphenyl-4-ylmethyl)acetamide bitartrate;

N-(2-diethylaminoethyl)-2-(2-(2-(3-chlorophenyl)-ethyl)-4-oxo-4,5,6,7-tetrahydro-cyclopentapyrimidin-1-yl)-N-(4'-trifluoromethyl-biphenyl-4-ylmethyl)acetamide;

N-(2-diethylaminoethyl)-2-(2-(2-(4-chlorophenyl)-ethyl)-4-oxo-4,5,6,7-tetrahydro-cyclopentapyrimidin-1-yl)-N-(4'-trifluoromethyl-biphenyl-4-ylmethyl)acetamide;

N-(2-diethylaminoethyl)-2-(2-(2-(4-methylphenyl)-ethyl)-4-oxo-4,5,6,7-tetrahydro-cyclopentapyrimidin-1-yl)-N-(4'-trifluoromethyl-biphenyl-4-ylmethyl)acetamide;

N-(2-diethylaminoethyl)-2-(2-(2-(4-(trifluoromethyl)phenyl)-ethyl)-4-oxo-4,5,6,7-tetrahydro-cyclopentapyrimidin-1-yl)-N-(4'-trifluoromethyl-biphenyl-4-ylmethyl)-acetamide;

N-(2-diethylaminoethyl)-2-(2-(2-(4-methoxyphenyl)-ethyl)-4-oxo-4,5,6,7-tetrahydro-cyclopentapyrimidin-1-yl)-N-(4'-trifluoromethyl-biphenyl-4-ylmethyl)acetamide bitartrate;

N-(2-diethylaminoethyl)-2-(2-(2-(4-(trifluoromethoxy)phenyl)-ethyl)-4-oxo-4,5,6,7-tetrahydro-cyclopentapyrimidin-1-yl)-N-(4'-trifluoromethyl-biphenyl-4-ylmethyl)-acetamide bitartrate;

or the free base of any of the bitartrate salts, or another pharmaceutically acceptable salt.

Further, of interest are compounds of formula (III), disclosed in WO 02/30904:

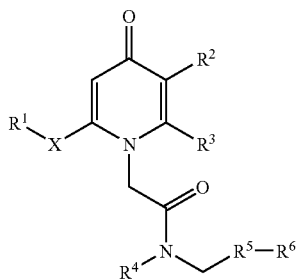

(III)

in which:
$R^1$ is an aryl group, optionally substituted by 1, 2, 3 or 4 substituents which can be the same or different selected from $C_{(1-6)}$alkyl, $C_{(1-6)}$alkoxy, $C_{(1-6)}$alkylthio, hydroxy, halogen, CN, mono to perfluoro-$C_{(1-4)}$alkyl, mono to perfluoro-$C_{(1-4)}$alkoxyaryl, and arylC$_{(1-4)}$alkyl;

$R^2$ is halogen, $C_{(1-3)}$alkyl, $C_{(1-3)}$alkoxy, hydroxyC$_{(1-3)}$alkyl, $C_{(1-3)}$alkylthio, $C_{(1-3)}$alkylsulphinyl, aminoC$_{(1-3)}$alkyl, mono- or di-$C_{(1-3)}$alkylaminoC$_{(1-3)}$alkyl, $C_{(1-3)}$alkylcarbonylaminoC$_{(1-3)}$alkyl, $C_{(1-3)}$alkoxyC$_{(1-3)}$alkylcarbonylamino$C_{(1-3)}$alkyl, $C_{(1-3)}$alkylsulphonylaminoC$_{(1-3)}$alkyl, $C_{(1-3)}$alkylcarboxy, $C_{(1-3)}$alkylcarboxyC$_{(1-3)}$alkyl, and $R^3$ is hydrogen, halogen, $C_{(1-3)}$alkyl, or hydroxyC$_{(1-3)}$alkyl; or $R^2$ and $R^3$ together with the pyridone ring carbon atoms to which they are attached form a fused 5- or 6-membered carbocyclic ring; or $R^2$ and $R^3$ together with the pyridone ring carbon atoms to which they are attached form a fused benzo or heteroaryl ring optionally substituted by 1, 2, 3 or 4 substituents which can be the same or different selected from halogen, $C_{(1-4)}$alkyl, cyano, $C_{(1-3)}$alkoxyC$_{(1-3)}$alkyl, $C_{(1-4)}$alkoxy or $C_{(1-4)}$alkylthio, or mono to perfluoro-$C_{(1-4)}$alkyl;

$R^4$ is hydrogen, $C_{(1-6)}$alkyl which can be unsubstituted or substituted by 1, 2 or 3 substituents selected from hydroxy, halogen, $OR^7$, $COR^7$, carboxy, $COOR^7$, $CONR^9R^{10}$, $NR^9R^{10}$, $NR^7COR^8$, mono- or di-(hydroxyC$_{(1-6)}$alkyl)amino and N-hydroxyC$_{(1-6)}$alkyl-N—C$_{(1-6)}$alkylamino; or $R^4$ is Het-C$_{(0-4)}$alkyl in which Het is a 5- to 7-membered heterocyclyl ring comprising N and optionally O or S, and in which N can be substituted by $COR^7$, $COOR^7$, $CONR^9R^{10}$, or $C_{(1-6)}$alkyl optionally substituted by 1, 2 or 3 substituents selected from hydroxy, halogen, $OR^7$, $COR^7$, carboxy, $COOR^7$, $CONR^9R^{10}$ or $NR^9R^{10}$, for instance, piperidin-4-yl, pyrrolidin-3-yl;

$R^5$ is an aryl or a heteroaryl ring optionally substituted by 1, 2, 3 or 4 substituents which can be the same or different selected from $C_{(1-6)}$alkyl, $C_{(1-6)}$alkoxy, $C_{(1-6)}$alkylthio, aryl $C_{(1-6)}$alkoxy, hydroxy, halogen, CN, $COR^7$, carboxy, $COOR^7$, $NR^7COR^8$, $CONR^9R^{10}$, $SO_2NR^9R^{10}$, $NR^7SO_2R^8$, $NR^9R^{10}$, mono to perfluoro-$C_{(1-4)}$alkyl and mono to perfluoro-$C_{(1-4)}$alkoxy;

$R^6$ is an aryl or a heteroaryl ring which is further optionally substituted by 1, 2, 3 or 4 substituents which can be the same or different selected from $C_{(1-6)}$alkyl, $C_{(1-6)}$alkoxy, $C_{(1-6)}$alkylthio, $C_{(1-6)}$alkylsulfonyl, arylC$_{(1-6)}$alkoxy, hydroxy, halogen, CN, $COR^7$, carboxy, $COOR^7$, $CONR^9R^{10}$, $NR^7COR^8$, $SO_2NR^9R^{10}$, $NR^7SO_2R^8$, $NR^9R^{10}$, mono to perfluoro-$C_{(1-4)}$alkyl and mono to perfluoro-$C_{(1-4)}$alkoxy, or $C_{(5-10)}$alkyl;

$R^7$ and $R^8$ are independently hydrogen or $C_{(1-12)}$alkyl, for instance $C_{(1-4)}$alkyl (e.g. methyl or ethyl);

$R^9$ and $R^{10}$ which can be the same or different is each selected from hydrogen, or $C_{(1-12)}$alkyl, or $R^9$ and $R^{10}$ together with the nitrogen to which they are attached form a 5- to 7 membered ring optionally containing one or more further heteroatoms selected from oxygen, nitrogen and sulphur, and optionally substituted by one or two substituents selected from hydroxy, oxo, $C_{(1-4)}$alkyl, $C_{(1-4)}$alkylcarboxy, aryl, e.g. phenyl, or aralkyl, e.g benzyl, for instance morpholine or piperazine; and X is a $C_{(2-4)}$alkylene group (optionally substituted by 1, 2 or 3 substituents selected from methyl and ethyl), CH=CH, (CH$_2$)$_n$S or (CH$_2$)$_n$O where n is 1, 2 or 3;

or a pharmaceutically acceptable salt thereof.

Of particular interest are those compounds of formula (III) where $R^2$ and $R^3$ together with the pyridone ring carbon atoms to which they are attached form a fused benzo or heteroaryl ring optionally substituted by 1, 2, 3 or 4 substituents which can be the same or different selected from halogen, $C_{(1-4)}$alkyl, cyano, $C_{(1-4)}$alkoxy or $C_{(1-4)}$alkylthio, or mono to perfluoro-$C_{(1-4)}$alkyl. Preferably, $R^1$ is phenyl optionally substituted by halogen, $C_{(1-6)}$alkyl, trifluoromethyl, $C_{(1-6)}$alkoxy, preferably, from 1 to 3 fluoro, more preferably, 2,3-difluoro. Representative examples of $R^4$ include piperidin-4-yl substituted at the 1-position by methyl, isopropyl, 1-(2-methoxyethyl), 1-(2-hydroxyethyl), t-butoxycarbonyl or ethoxycarbonylmethyl; ethyl substituted at the 2-position by aminoethyl; 1-ethylpiperidinylmethyl; piperidin-4-yl; 3-diethylaminopropyl; 4-pyrrolidin-1-ylbutyl and 1-ethylpyrrolidin-3-yl. Preferably $R^4$ is 1-(2-methoxyethyl)piperidin-4-yl, 1-methylpiperidin-4-yl or 1-ethylpyrrolidin-3-yl. Representative examples of $R^5$ include phenyl and pyridyl. Preferably, $R^5$ is phenyl. Representative examples of $R^6$ include phenyl optionally substituted by halogen, or trifluoromethyl, preferably at the 4-position and hexyl. Preferably, $R^6$ is phenyl substituted by trifluoromethyl at the 4-position. Further representative examples of $R^6$ include phenyl substituted by 1 or more $C_{(1-3)}$alkyl. Preferably, $R^6$ is phenyl substituted by ethyl in the 4-position. Preferably, $R^5$ and $R^6$ together form a 4-(phenyl)phenyl or a 2-(phenyl)pyridinyl substituent in which the remote phenyl ring can be optionally substituted by halogen or trifluoromethyl, preferably at the 4-position. Preferably X is $C_{(2-4)}$alkylene, more preferably $C_{(2-3)}$alkylene, most preferably, $(CH_2)_2$, or $CH_2S$.

It will be appreciated that within the group of compounds comprising formula (III) there is sub-group of compounds in which:

$R^1$ is phenyl substituted by 2,3-difluoro;

$R^2$ and $R^3$, together with the pyridone ring carbon atoms to which they are attached, form a fused benzo or pyrido ring;

$R^4$ is 1-(2-methoxyethyl)piperidin-4-yl;

$R^5$ and $R^6$ together form a 4-(phenyl)phenyl substituent in which the remote phenyl ring is substituted by trifluoromethyl, preferably at the 4-position; and X is $CH_2S$ or $(CH_2)_2$.

The following compounds of formula (III) are of interest:

N-(2-diethylaminoethyl)-2-[2-(2,3-difluorobenzylthio)-4-oxo-4H-quinolin-1-yl]-N-(4'-trifluoromethylbiphenyl-4-ylmethyl)acetamide bitartrate;

N-(2-diethylaminoethyl)-2-[2-(2-(2,3-difluorophenyl)ethyl)-4-oxo-4H-quinolin-1-yl]-N-(4'-trifluoromethylbiphenyl-4-ylmethyl)acetamide;

N-(2-diethylaminoethyl)-2-[2-(2-(2,3-difluorophenyl)ethyl)-4-oxo-4H-quinolin-1-yl]-N-(4'-trifluoromethylbiphenyl-4-ylmethyl)acetamide bitartrate;

N-(2-diethylaminoethyl)-2-[2-(2,3-difluorobenzylthio)-4-oxo-5,6-trimethylene-pyridin-1-yl]-N-(4'-trifluoromethylbiphenyl-4-ylmethyl)acetamide bitartrate;

N-(1-(2-methoxyethyl)piperidin-4-yl)-2-[2-(2,3-difluorobenzylthio)-4-oxo-4H-quinolin-1-yl]-N-(4'-trifluoromethylbiphenyl-4-ylmethyl)acetamide;

N-(1-methylpiperidin-4-yl)-2-[2-(2,3-difluorobenzylthio)-4-oxo-4H-quinolin-1-yl]-N-(4'-trifluoromethylbiphenyl-4-ylmethyl)acetamide bitartrate;

N-(1-methylpiperidin-4-yl)-2-[2-(2-(2,3-difluorophenyl)ethyl)-4-oxo-4H-[1,8]naphthyridin-1-yl]-N-(4'-trifluoromethylbiphenyl-4-ylmethyl)acetamide bitartrate;

N-(1-(2-methoxyethyl)piperidin-4-yl)-2-[2-(2-(2,3-difluorophenyl)ethyl)-4-oxo-4H-[1,8]naphthyridin-1-yl]-N-(4'-trifluoromethylbiphenyl-4-ylmethyl)acetamide;

N-(1-(2-methoxyethyl)piperidin-4-yl)-2-[2-(2,3-difluorobenzylthio)-4-oxo-4H-[1,8]naphthyridin-1-yl]-N-(4'-trifluoromethylbiphenyl-4-ylmethyl)acetamide bitartrate;

N-(1-ethylpiperidin-4-yl)-2-[2-(2,3-difluorobenzylthio)-4-oxo-4H-quinolin-1-yl]-N-(4'-ethylbiphenyl-4-ylmethyl)acetamide bitartrate;

N-(1-ethylpiperidin-4-yl)-2-[5-(2-(2,3-difluorophenyl)ethyl)-2-methyl-7-oxo-7H-thiazolo[4,5-b]pyridin-4-yl]-N-(4'-trifluoromethylbiphenyl-4-ylmethyl)acetamide bitartrate;

(±)N-(1-ethylpyrrolidin-3-yl)-2-[2-(2-(2,3-difluorophenyl)ethyl)-4-oxo-4H-quinolin-1-yl]-N-(4'-trifluoromethylbiphenyl-4-ylmethyl)acetamide bitartrate;

(±)N-(1-ethylpyrrolidin-3-yl)-2-[2-(2,3-difluorobenzylthio)-4-oxo-4H-quinolin-1-yl]-N-(4'-trifluoromethylbiphenyl-4-ylmethyl)acetamide bitartrate;

N-(1-(2-methoxyethyl)piperidin-4-yl)-2-[2-(2,3-difluorobenzylthio)-4-oxo-4H-quinolin-1-yl]-N-(4'-trifluoromethylbiphenyl-4-ylmethyl)acetamide bitartrate;

N-(1-(2-methoxyethyl)piperidin-4-yl)-2-[2-(2,3-difluorobenzylthio)-4-oxo-4H-quinolin-1-yl]-N-(4'-trifluoromethylbiphenyl-4-ylmethyl)acetamide dihydrochloride;

N-(1-(2-methoxyethyl)piperidin-4-yl)-2-[2-(2,3-difluorobenzylthio)-4-oxo-4H-quinolin-1-yl]-N-(4'-trifluoromethylbiphenyl-4-ylmethyl)acetamide mono paratoluenesulphonate;

N-(1-(2-methoxyethyl)piperidin-4-yl)-2-[2-(2-(2,3-difluorophenyl)ethyl)-4-oxo-4H-[1,8]naphthyridin-1-yl]-N-(4'-trifluoromethylbiphenyl-4-ylmethyl)acetamide bitartrate;

N-(1-(2-methoxyethyl)piperidin-4-yl)-2-[2-(2-(2,3-difluorophenyl)ethyl)-4-oxo-4H-[1,8]naphthyridin-1-yl]-N-(4'-trifluoromethylbiphenyl-4-ylmethyl)acetamide monohydrochloride;

N-(1-(2-methoxyethyl)piperidin-4-yl)-2-[2-(2-(2,3-difluorophenyl)ethyl)-4-oxo-4H-[1,8]naphthyridin-1-yl]-N-(4'-trifluoromethylbiphenyl-4-ylmethyl)acetamide dihydrochloride;

N-(2-diethylaminoethyl)-2-[2-(4-fluorobenzylthio)-4-oxo-4H-quinolin-1-yl]-N-(4'-trifluoromethylbiphenyl-4-ylmethyl)acetamide bitartrate;

N-(2-diethylaminoethyl)-2-[2-(4-fluorobenzylthio)-4-oxo-5,6-trimethylene-pyridin-1-yl]-N-(4'-trifluoromethyl-biphenyl-4-ylmethyl)acetamide bitartrate;

N-(2-diethylaminoethyl)-2-[2-(2,3-difluorobenzylthio)-4-oxo-5,6-trimethylene-pyridin-1-yl]-N-(4'-trifluoromethyl-biphenyl-4-ylmethyl)acetamide bitartrate;

N-(2-diethylaminoethyl)-2-[2-(4-fluorophenyl)ethyl)-4-oxo-4H-quinolin-1-yl]-N-(4'-trifluoromethylbiphenyl-4-ylmethyl)acetamide;

N-(2-diethylaminoethyl)-2-[2-(2-(3,4-difluorophenyl)ethyl)-4-oxo-4H-quinolin-1-yl]-N-(4'-trifluoromethylbiphenyl-4-ylmethyl)acetamide bitartrate;

N-(2-diethylaminoethyl)-2-[2-(2-(2-fluorophenyl)ethyl)-4-oxo-4H-quinolin-1-yl]-N-(4'-trifluoromethylbiphenyl-4-ylmethyl)acetamide bitartrate;

N-(2-diethylaminoethyl)-2-[2-(2-(3-chlorophenyl)ethyl)-4-oxo-4H-quinolin-1-yl]-N-(4'-trifluoromethylbiphenyl-4-ylmethyl)acetamide bitartrate;

N-(2-diethylaminoethyl)-2-[2-(2-(2,3-difluorophenyl)ethyl)-4-oxo-4H-[1,8]naphthyridin-1-yl)]-N-(4'-trifluoromethylbiphenyl-4-ylmethyl)acetamide bitartrate;

N-(1-ethylpiperidin-4-yl)-2-[2-(2-(2,3-difluorophenyl)ethyl)-4-oxo-4H-[1,8]naphthyridin-1-yl)]-N-(4'-trifluoromethylbiphenyl-4-ylmethyl)acetamide;

N-(1-ethylpiperidin-4-yl)-2-[2-(2-(2,3-difluorophenyl)ethyl)-4-oxo-4H-quinolin-1-yl]-N-(4'-trifluoromethylbiphenyl-4-ylmethyl)acetamide bitartrate;

N-(2-pyrrolidin-1-ylethyl)-2-[2-(2-(2,3-difluorophenyl)ethyl)-4-oxo-4H-quinolin-1-yl]-N-(4'-trifluoromethylbiphenyl-4-ylmethyl)acetamide bitartrate;

N-(1-isopropylpiperidin-4-yl)-2-[2-(2-(2,3-difluorophenyl)ethyl)-4-oxo-4H-quinolin-1-yl]-N-(4'-trifluoromethylbiphenyl-4-ylmethyl)acetamide bitartrate;

N-(2-piperidin-1-ylethyl)-2-[2-(2-(2,3-difluorophenyl)ethyl)-4-oxo-4H-quinolin-1-yl]-N-(4'-trifluoromethylbiphenyl-4-ylmethyl)acetamide bitartrate;

N-(2-diethylaminoethyl)-2-[2-(2,3-difluorobenzylthio)-7-fluoro-4-oxo-4H-quinolin-1-yl]-N-(4'-trifluoromethylbiphenyl-4-ylmethyl)acetamide bitartrate;

N-(2-diethylaminoethyl)-5-[2-(2-(2,3-difluorophenyl)ethyl)-2-methyl-7-oxo-7H-thieno[3,2-b]pyridin-4-yl]-N-(4'-trifluoromethylbiphenyl-4-ylmethyl)acetamide bitartrate;

N-(2-diethylaminoethyl)-2-[2-(2-(2,3-difluorophenyl)ethyl)-5,6-dimethyl-4-oxo-4H-pyridin-1-yl]-N-(4'-trifluoromethylbiphenyl-4-ylmethyl)acetamide bitartrate;

N-(2-diethylaminoethyl)-2-[2-(2-(2,3-difluorophenyl)ethyl)-5-ethyl-4-oxo-4H-pyridin-1-yl]-N-(4'-trifluoromethylbiphenyl-4-ylmethyl)acetamide bitartrate;

N-(1-(2-methoxyethyl)piperidin-4-yl)-2-[2-(2-(2,3-difluorophenyl)ethyl)-4-oxo-4H-quinolin-1-yl]-N-(4'-trifluoromethylbiphenyl-4-ylmethyl)acetamide bitartrate;

N-(1-methylpiperidin-4-yl)-2-[2-(2-(2,3-difluorophenyl)ethyl)-4-oxo-4H-quinolin-1-yl]-N-(4'-trifluoromethylbiphenyl-4-ylmethyl)acetamide bitartrate;

N-(2-diethylaminoethyl)-2-[2-(2-(2,3-difluorophenyl)ethyl)-4-oxo-4H-thieno[3,4-b]pyridin-1-yl]-N-(4'-trifluoromethylbiphenyl-4-ylmethyl)acetamide bitartrate;

N-(1-ethylpiperidin-4-yl)-2-[2-(2,3-difluorobenzylthio)-4-oxo-4H-quinolin-1-yl]-N-(4'-trifluoromethylbiphenyl-4-ylmethyl)acetamide bitartrate;

N-(2-pyrrolidin-1-ylethyl)-2-[2-(2,3-difluorobenzylthio)-4-oxo-4H-quinolin-1-yl]-N-(4'-trifluoromethylbiphenyl-4-ylmethyl)acetamide bitartrate;

N-(1-ethylpiperidin-4-yl)-2-[6-(2-(2,3-difluorophenyl)ethyl)-2-methyl-4-oxo-4H-pyrazolo[3,4-b]pyridin-7-yl]-N-(4'-trifluoromethylbiphenyl-4-ylmethyl)acetamide bitartrate;

N-(1-isopropylpiperidin-4-yl)-2-[2-(2,3-difluorobenzylthio)-4-oxo-4H-quinolin-1-yl]-N-(4'-trifluoromethylbiphenyl-4-ylmethyl)acetamide bitartrate;

N-(1-ethylpiperidin-4-ylmethyl)-2-[2-(2-(2,3-difluorophenyl)ethyl)-4-oxo-4H-quinolin-1-yl]-N-(4'-trifluoromethylbiphenyl-4-ylmethyl)acetamide bitartrate;

N-(3-diethylaminopropyl)-2-[2-(2,3-difluorobenzylthio)-4-oxo-4H-quinolin-1-yl]-N-(4'-trifluoromethylbiphenyl-4-ylmethyl)acetamide bitartrate;

N-(4-pyrrolidin-1-ylbutyl)-2-[2-(2-(2,3-difluorophenyl)ethyl)-4-oxo-4H-quinolin-1-yl]-N-(4'-trifluoromethylbiphenyl-4-ylmethyl)acetamide bitartrate;

N-(3-diethylaminopropyl)-2-[2-(2-(2,3-difluorophenyl)ethyl)-4-oxo-4H-quinolin-1-yl]-N-(4'-trifluoromethylbiphenyl-4-ylmethyl)acetamide bitartrate;

N-(4-pyrrolidin-1-ylbutyl)-2-[2-(2,3-difluorobenzylthio)-4-oxo-4H-quinolin-1-yl]-N-(4'-trifluoromethylbiphenyl-4-ylmethyl)acetamide bitartrate;

N-(1-ethylpiperidin-4-yl)-2-[5-(2,3-difluorobenzylthio)-7-oxo-7H-thieno[3,2-b]pyridin-4-yl]-N-(4'-trifluoromethylbiphenyl-4-ylmethyl)acetamide bitartrate;

N-(2-diethylaminoethyl)-2-[5-(2-(2,3-difluorophenyl)ethyl)-2-methyl-7-oxo-7H-thiazolo[4,5-b]pyridin-4-yl]-N-(4'-trifluoromethylbiphenyl-4-ylmethyl)acetamide bitartrate;

N-(2-diethylaminoethyl)-2-[2-(2,3-difluorobenzylthio)-4-oxo-4H-quinolin-1-yl]-N-(4'-ethylbiphenyl-4-ylmethyl)acetamide bitartrate;

N-(2-diethylaminoethyl)-2-[2-(2-(2,3-difluorophenyl)ethyl)-4-oxo-4H-quinolin-1-yl]-N-(4'-ethylbiphenyl-4-ylmethyl)acetamide bitartrate;

N-(2-diethylaminoethyl)-2-[2-(2,3-difluorobenzylthio)-4-oxo-4H-quinolin-1-yl]-N-(4'-isopropylbiphenyl-4-ylmethyl)acetamide bitartrate;

N-(2-diethylaminoethyl)-2-[2-(2-(2,3-difluorophenyl)ethyl)-4-oxo-4H-quinolin-1-yl]-N-(4'-isopropylbiphenyl-4-ylmethyl)acetamide bitartrate;

N-(2-diethylaminoethyl)-2-[2-(2,3-difluorobenzylthio)-4-oxo-4H-[1,8]naphthyridin-1-yl]-N-(4'-trifluoromethylbiphenyl-4-ylmethyl)acetamide bitartrate;

N-(1-ethylpiperidin-4-yl)-2-[2-(2,3-difluorobenzylthio)-4-oxo-4H-[1,8]naphthyridin-1-yl]-N-(4'-trifluoromethylbiphenyl-4-ylmethyl)acetamide bitartrate;

N-(2-diethylaminoethyl)-2-[2-(2-(2,3-difluorophenyl)ethyl)-4-oxo-4H-quinolin-1-yl]-N-(4'-methylbiphenyl-4-ylmethyl)acetamide bitartrate;

N-(2-diethylaminoethyl)-2-[2-(2,3-difluorobenzylthio)-4-oxo-4H-quinolin-1-yl]-N-(4'-methylbiphenyl-4-ylmethyl)acetamide bitartrate;

N-(1-ethoxycarbonylmethylpiperidin-4-yl)-2-[2-(2-(2,3-difluorophenyl)ethyl)-4-oxo-4H-quinolin-1-yl]-N-(4'-trifluoromethylbiphenyl-4-ylmethyl)acetamide bitartrate;

N-(1-isopropylpiperidin-4-yl)-2-[2-(2-(2,3-difluorophenyl)ethyl)-4-oxo-4H-[1,8]naphthyridin-1-yl]-N-(4'-trifluoromethylbiphenyl-4-ylmethyl)acetamide bitartrate;

N-(2-diethylaminoethyl)-2-[2-(2,3-difluorobenzylthio)-4-oxo-4H-quinolin-1-yl]-N-(3',4'-dimethylbiphenyl-4-ylmethyl)acetamide bitartrate;

N-(1-(t-butoxycarbonyl)piperidin-4-yl)-2-[2-(2-(2,3-difluorophenyl)ethyl)-4-oxo-4H-[1,8]naphthyridin-1-yl]-N-(4'-trifluoromethylbiphenyl-4-ylmethyl)acetamide bitartrate;

N-(2-diethylaminoethyl)-2-[2-(2,3-difluorobenzylthio)-4-oxo-4H-quinolin-1-yl]-N-(3',4'-difluorobiphenyl-4-ylmethyl)acetamide bitartrate;

N-(2-diethylaminoethyl)-2-[6-(2,3-difluorobenzylthio)-4-oxo-4H-thieno-[2,3-b]pyridin-7-yl]-N-(4'-trifluoromethylbiphenyl-4-ylmethyl)acetamide bitartrate;

N-(1-methylpiperidin-4-yl)-2-[2-(2,3-difluorobenzylthio)-4-oxo-4H-[1,8]naphthyridin-1-yl]-N-(4'-trifluoromethylbiphenyl-4-ylmethyl)acetamide bitartrate;

N-(1-ethylpiperidin-4-yl)-2-[2-(2-(2,3,4-trifluorophenyl)ethyl)-4-oxo-4H-quinolin-1-yl]-N-(4'-trifluoromethylbiphenyl-4-ylmethyl)acetamide bitartrate;

N-(2-diethylaminoethyl)-2-[6-(2,3-difluorobenzylthio)-2-methyl-4-oxo-2,4-dihydropyrazolo[3,4-b]pyridin-7-yl]-N-(4'-trifluoromethylbiphenyl-4-ylmethyl)acetamide bitartrate;

N-(1-ethylpiperidin-4-yl)-2-[6-(2-(2,3-difluorophenyl)ethyl)-2-ethyl-4-oxo-2,4-dihydropyrazolo[3,4-b]pyridin-7-yl]-N-(4'-trifluoromethylbiphenyl-4-ylmethyl)acetamide bitartrate;

N-(1-ethylpiperidin-4-yl)-2-[6-(2-(2,3-difluorophenyl)ethyl)-2-isopropyl-4-oxo-2,4-dihydropyrazolo[3,4-b]pyridin-7-yl]-N-(4'-trifluoromethylbiphenyl-4-ylmethyl)-acetamide bitartrate;

N-(1-ethylpiperidin-4-yl)-2-[2-(2-(2,3-difluorophenyl)ethyl)-4-oxo-4H-quinolin-1-yl]-N-(4'-ethylbiphenyl-4-ylmethyl)acetamide bitartrate;

N-(1-isopropylpiperidin-4-yl)-2-[5-(2-(2,3-difluorophenyl)ethyl)-2-methyl-7-oxo-7H-thiazolo[4,5-b]pyridin-4-yl]-N-(4'-trifluoromethylbiphenyl-4-ylmethyl)acetamide bitartrate;

N-(1-(2-methoxyethyl)piperidin-4-yl)-2-[5-(2-(2,3-difluorophenyl)ethyl)-2-methyl-7-oxo-7H-thiazolo[4,5-b]pyridin-4-yl]-N-(4'-trifluoromethylbiphenyl-4-ylmethyl)-acetamide bitartrate;

N-(1-ethylpiperidin-4-yl)-2-[2-(2-(2,3-difluorophenyl)ethyl)-4-oxo-5,6-trimethylenepyridin-1-yl]-N-(4'-trifluoromethylbiphenyl-4-ylmethyl)acetamide bitartrate;

N-(1-methylpiperidin-4-yl)-2-[2-(2-(2,3-difluorophenyl)ethyl)-4-oxo-5,6-trimethylenepyridin-1-yl]-N-(4'-trifluoromethylbiphenyl-4-ylmethyl)acetamide bitartrate;

N-(1-(2-methoxyethyl)piperidin-4-yl)-2-[2-(2-(2,3-difluorophenyl)ethyl)-4-oxo-5,6-trimethylenepyridin-1-yl]-N-(4'-trifluoromethylbiphenyl-4-ylmethyl)acetamide bitartrate;

N-(1-isopropylpiperidin-4-yl)-2-[2-(2-(2,3-difluorophenyl)ethyl)-4-oxo-5,6-trimethylenepyridin-1-yl]-N-(4'-trifluoromethylbiphenyl-4-ylmethyl)acetamide bitartrate;

N-(1-ethylpiperidin-4-yl)-2-[5-(2-(2,3-difluorophenyl)ethyl)-2-methyl-7-oxo-2,7-dihydropyrazolo[4,3-b]pyridin-4-yl]-N-(4'-trifluoromethylbiphenyl-4-ylmethyl)acetamide bitartrate;

N-(1-ethylpiperidin-4-yl)-2-[5-(2-(2,3-difluorophenyl)ethyl)-1-methyl-7-oxo-1,7-dihydropyrazolo[4,3-b]pyridin-4-yl]-N-(4'-trifluoromethylbiphenyl-4-ylmethyl)acetamide bitartrate;

N-(1-ethylpiperidin-4-yl)-2-[2-(2-(2,3-difluorophenyl)ethyl)-4-oxo-5,6-trimethylenepyridin-1-yl]-N-(4'-trifluoromethylbiphenyl-4-ylmethyl)acetamide bitartrate;

N-(1-ethylpiperidin-4-yl)-2-[2-(2-(2,3-difluorophenyl)ethyl)-7-methyl-4-oxo-4H-[1,8]naphthyridin-1-yl]-N-(4'-trifluoromethylbiphenyl-4-ylmethyl)acetamide bitartrate;

N-(2-diethylaminoethyl)-2-[2-(2-(2,3-difluorophenyl)ethyl)-7-methyl-4-oxo-4H-[1,8]naphthyridin-1-yl]-N-(4'-trifluoromethylbiphenyl-4-ylmethyl)acetamide bitartrate;

N-(1-methylpiperidin-4-yl)-2-[2-(2-(2,3-difluorophenyl)ethyl)-7-methyl-4-oxo-4H-[1,8]naphthyridin-1-yl]-N-(4'-trifluoromethylbiphenyl-4-ylmethyl)acetamide bitartrate;

N-(1-isopropylpiperidin-4-yl)-2-[2-(2-(2,3-difluorophenyl)ethyl)-7-methyl-4-oxo-4H-[1,8]naphthyridin-1-yl]-N-(4'-trifluoromethylbiphenyl-4-ylmethyl)acetamide bitartrate;

N-(1-(2-methoxyethyl)piperidin-4-yl)-2-[2-(2-(2,3-difluorophenyl)ethyl)-7-methyl-4-oxo-4H-[1,8]naphthyridin-1-yl]-N-(4'-trifluoromethylbiphenyl-4-ylmethyl)-acetamide bitartrate;

N-(1-methylpiperidin-4-yl)-2-[2-(2,3-difluorobenzylthio)-4-oxo-5,6-trimethylene-pyridin-1-yl]-N-(4'-trifluoromethylbiphenyl-4-ylmethyl)acetamide bitartrate;

N-(1-ethylpiperidin-4-yl)-2-[2-(2,3-difluorobenzylthio)-4-oxo-5,6-trimethylene-pyridin-1-yl]-N-(4'-trifluoromethylbiphenyl-4-ylmethyl)acetamide bitartrate;

N-(1-isopropylpiperidin-4-yl)-2-[2-(2,3-difluorobenzylthio)-4-oxo-5,6-trimethylenepyridin-1-yl]-N-(4'-trifluoromethylbiphenyl-4-ylmethyl)acetamide bitartrate;

N-(1-(2-methoxyethyl)piperidin-4-yl)-2-[2-(2,3-difluorobenzylthio)-4-oxo-5,6-trimethylenepyridin-1-yl]-N-(4'-trifluoromethylbiphenyl-4-ylmethyl)acetamide bitartrate;

N-(2-diethylaminoethyl)-2-[2-(2-(2,3-difluorophenyl)ethyl)-4-oxo-5,6-tetramethylenepyridin-1-yl]-N-(4'-trifluoromethylbiphenyl-4-ylmethyl)acetamide bitartrate;

N-(1-methylpiperidin-4-yl)-2-[2-(2,3-difluorobenzylthio)-4-oxo-4H-quinolin-1-yl]-N-(4'-chlorobiphenyl-4-ylmethyl)acetamide bitartrate;

N-(1-methylpiperidin-4-yl)-2-[2-(2-(2,3-difluorophenyl)ethyl)-4-oxo-4H-quinolin-1-yl]-N-(4'-chlorobiphenyl-4-ylmethyl)acetamide bitartrate;

N-(1-ethylpiperidin-4-yl)-2-[2-(2-(2,3-difluorophenyl)ethyl)-4-oxo-4H-quinolin-1-yl]-N-(4'-chlorobiphenyl-4-ylmethyl)acetamide bitartrate;

N-(1-(2-methoxyethyl)piperidin-4-yl)-2-[2-(2-(2,3-difluorophenyl)ethyl)-4-oxo-4H-quinolin-1-yl]-N-(4'-chlorobiphenyl-4-ylmethyl)acetamide bitartrate;

N-(1-isopropylpiperidin-4-yl)-2-[2-(2-(2,3-difluorophenyl)ethyl)-4-oxo-4H-quinolin-1-yl]-N-(4'-chlorobiphenyl-4-ylmethyl)acetamide bitartrate;

N-(2-diethylaminoethyl)-2-[6-(2-(2,3-difluorophenyl)ethyl)-2-methyl-4-oxo-4H-pyrazolo[3,4-b]pyridin-7-yl]-N-(4'-trifluoromethylbiphenyl-4-ylmethyl)acetamide bitartrate;

N-(1-(t-butoxycarbonyl)piperidin-4-yl)-2-[2-(2,3-difluorobenzylthio)-4-oxo-4H-[1,8]naphthyridin-1-yl]-N-(4'-trifluoromethylbiphenyl-4-ylmethyl)acetamide;

N-(1-ethylpiperidin-4-yl)-2-[6-(2-(2,3-difluorophenyl)ethyl)-2-(2-methoxyethyl)-4-oxo-4H-pyrazolo[3,4-b]pyridin-7-yl]-N-(4'-trifluoromethylbiphenyl-4-ylmethyl)acetamide bitartrate;

N-(2-diethylaminoethyl)-2-[4-oxo-2-(2-(2,3,4-trifluorophenyl)ethyl)-4H-quinolin-1-yl]-N-(4'-trifluoromethyl-biphenyl-4-ylmethyl)acetamide bitartrate;

N-(2-diethylaminoethyl)-2-[2-(2-(2,4-difluorophenyl)ethyl)-4-oxo-4H-quinolin-1-yl]-N-(4'-trifluoromethylbiphenyl-4-ylmethyl)acetamide bitartrate;

N-(2-diethylaminoethyl)-2-[2-(2-(3-fluorophenyl)ethyl)-4-oxo-4H-quinolin-1-yl]-N-(4'-trifluoromethylbiphenyl-4-ylmethyl)acetamide bitartrate;

N-(piperidin-4-yl)-2-[2-(2,3-difluorobenzylthio)-4-oxo-4H-quinolin-1-yl]-N-(4'-trifluoromethylbiphenyl-4-ylmethyl)acetamide bitartrate;

N-(piperidin-4-yl)-2-[2-(2-(2,3-difluorophenyl)ethyl)-4-oxo-4H-quinolin-1-yl]-N-(4'-trifluoromethylbiphenyl-4-ylmethyl)acetamide bitartrate;

N-(piperidin-4-yl)-2-[2-(2-(2,3-difluorophenyl)ethyl)-4-oxo-5,6-trimethylene-pyridin-1-yl]-N-(4'-trifluoromethylbiphenyl-4-ylmethyl)acetamide bitartrate;

N-(piperidin-4-yl)-2-[2-(2-(2,3-difluorophenyl)ethyl)-4-oxo-4H-[1,8]naphthyridin-1-yl]-N-(4'-trifluoromethylbiphenyl-4-ylmethyl)acetamide bitartrate;

N-(piperidin-4-yl)-2-[2-(2,3-difluorobenzylthio)-4-oxo-4H-[1,8]naphthyridin-1-yl]-N-(4'-trifluoromethylbiphenyl-4-ylmethyl)acetamide trifluoroacetate;

N-(2-ethylaminoethyl)-2-[2-(2,3-difluorobenzylthio)-4-oxo-4H-quinolin-1-yl]-N-(4'-trifluoromethylbiphenyl-4-ylmethyl)acetamide;

N-(2-ethylaminoethyl)-2-[2-(2-(2,3-difluorophenyl)ethyl)-4-oxo-4H-quinolin-1-yl]-N-(4'-trifluoromethylbiphenyl-4-ylmethyl)acetamide;

N-(1-(2-hydroxyethyl)piperidin-4-yl)-2-[2-(2-(2,3-difluorophenyl)ethyl)-4-oxo-4H-quinolin-1-yl]-N-(4'-trifluoromethylbiphenyl-4-ylmethyl)acetamide bitartrate; or the free base thereof, or another pharmaceutically acceptable salt.

Formula (IV)

Also of interest are compounds of formula (IV)

(IV)

wherein:

$R^1$ is an aryl group, unsubstituted or substituted by 1, 2, 3 or 4 substituents which can be the same or different selected from the group consisting of $C_1$-$C_6$ alkyl, $C_1$-$C_6$ alkoxy, $C_1$-$C_6$ alkylthio, aryl $C_1$-$C_6$ alkoxy, hydroxy, halo, CN, $COR^6$, $COOR^6$, $NR^6COR^7$, $CONR^8R^9$, $SO_2NR^8R^9$, $NR^6SO_2R^7$, $NR^8R^9$, halo $C_1$-$C_4$ alkyl, and halo $C_1$-$C_4$ alkoxy;

W is CH and X is N, or W is N and X is CH, W and X are both CH, or W and X are N;

Y is $C_2$-$C_4$ alkyl, $R^2$ is hydrogen, $C_1$-$C_6$ alkyl, $C_1$-$C_6$ alkoxy, $C_1$-$C_6$ alkylthio, aryl $C_1$-$C_6$ alkoxy, hydroxy, halo, CN, $COR^6$, carboxy, $COOR^6$, $NR^6COR^7$, $CONR^8R^9$, $SO_2NR^8R^9$, $NR^6SO_2R^7$, $NR^8R^9$, mono to perfluoro-$C_1$-$C_6$ alkyl, or mono to perfluoro-$C_1$-$C_6$ alkoxy;

n is 0-5;

$R^3$ is $C_1$-$C_4$ alkyl;

$R^4$ is $C_1$-$C_4$ alkyl;

$R^5$ is hydrogen, $C_1$-$C_{10}$ alkyl, $C_2$-$C_{10}$ alkenyl, $C_2$-$C_{10}$ alkynyl, halo $C_1$-$C_4$ alkyl, $C_3$-$C_8$ cycloalkyl, $C_3$-$C_8$ cycloalkyl, $C_3$-$C_8$ cycloalkyl $C_1$-$C_4$ alkyl, $C_5$-$C_8$ cycloalkenyl, $C_5$-$C_8$ cycloalkenyl $C_1$-$C_4$ alkyl, 3-8-membered heterocloalkyl, 3-8-membered heterocycloalkyl $C_1$-$C_4$ alkyl, $C_6$-$C_{14}$ aryl, $C_6$-$C_{14}$ aryl $C_1$-$C_{10}$ alkyl, heteroaryl, or heteroaryl $C_1$-$C_{10}$ alkyl; wherein each group is optionally one or more times by the same and/or a different group which is $C_1$-$C_6$ alkoxy, $C_1$-$C_6$ alkylthio, aryl $C_1$-$C_6$ alkoxy, hydroxy, halo, CN, $NR^8R^9$, or halo $C_1$-$C_4$ alkoxy $R^6$ and $R^7$ are independently hydrogen or $C_1$-$C_{10}$ alkyl;

$R^8$ and $R^9$ are the same or different and are hydrogen or $C_1$-$C_{10}$ alkyl, or $R^9$ and $R^{10}$ together with the nitrogen to which they are attached form a 5- to 7 membered ring optionally containing one or more further heteroatoms selected from oxygen, nitrogen and sulphur, and optionally substituted by one or two substituents selected from the group consisting of hydroxy, oxo, $C_1$-$C_4$ alkyl, $C_1$-$C_4$ alkylcarboxy, aryl, and aryl $C_1$-$C_4$ alkyl;

or a pharmaceutically acceptable salt thereof.

Without intending to exclude any defined substituents and/or their recited radicals from the scope of formula (IV), the following R groups and the associated radicals are of particular interest:

As regards $R^1$, it can be an phenyl group optionally substituted by 1, 2, 3 or 4 substituents which can be the same or different selected from halo, $C_1$-$C_6$ alkyl, trifluoromethyl or $C_1$-$C_6$ alkoxy. More specifically, phenyl is unsubstituted or substituted by 1, 2, 3 or 4 halogen substituents, particularly, from 1 to 3 fluoro groups, and most particularly, 2,3-difluoro, 2,4-difluoro or 4-fluoro.

A further embodiment of formula (I) is where Y is —$CH_2CH_2$—.

The invention also provides a compound of formula (I) in which $R^2$ is hydrogen, by default, or is halo, $C_1$-$C_6$ alkyl, mono to perfluoro-$C_1$-$C_4$ alkyl, mono to perfluoro $C_1$-$C_4$$_6$ alkoxy, or $C_1$-$C_6$ alkoxy; particularly mono to perfluoro-$C_1$-$C_4$ alkyl, mono to perfluoro-$C_1$-$C_4$ alkoxy, or $C_1$-$C_6$ alkoxy.

Of particular interest are the compounds where $R^2$ is other than hydrogen, n in $(R^2)_n$ is 1, 2, or 3, and the substitution pattern is meta and/or para, particularly para, i.e. a 4-position substituent. Exemplified compounds include those where $R^2$ is 4-trifluoromethyl or 4-trifluoromethoxy.

$R^3$ and $R^4$ can be the same or different and are methyl, ethyl, n-propyl, or n-butyl. Of particular interest are those compounds of formula (I) where $R^3$ and $R^4$ are the same and are methyl, or ethyl; methyl is of particular interest.

$R^5$ can be hydrogen, $C_{(1-6)}$ alkyl which is a straight chain, or branched. Of particular interest is methyl, ethyl, propyl, isopropyl, n-butyl, sec-butyl, iso-butyl, t-butyl, n-pentyl or n-hexyl.

Any of the compounds described herein above can be prepared in crystalline or non-crystalline form, and, if crystalline, can be solvated, e.g. as the hydrate. This invention includes within its scope stoichiometric solvates (e.g. hydrates).

Certain of the compounds described herein can contain one or more chiral atoms, or can otherwise be capable of existing as two enantiomers. The compounds useful in the methods as described herein include mixtures of enantiomers as well as purified enantiomers or enantiomerically enriched mixtures. Also included within the scope of the invention are the individual isomers of the compounds represented by formulas (I)-(IV), as well as any wholly or partially equilibrated mixtures thereof. The present invention also covers the individual isomers of the claimed compounds as mixtures with isomers thereof in which one or more chiral centers are inverted. Also, it is understood that any tautomers and mixtures of tautomers of the claimed compounds are included within the scope of the compounds of formulas (I)-(IV). The different isomeric forms can be separated or resolved one from the other by conventional methods, or any given isomer can be obtained by conventional synthetic methods or by stereospecific or asymmetric syntheses.

Syntheses of the Compounds of Formula (I), (II), (III) and (IV)

Methods for preparing compounds of formula (I), (II) and (III) have been published in the patent literature. For example, methods for making formula (I) can be found in WO 01/60805 and WO03/016287. Methods for making compounds of formula (II) have been set out in WO 02/30911. And methods for making compounds of formula (III) can be found in WO 02/30904. This document provides methods for making compounds of formula (IV), methods copied from U.S. provisional applications 60/829,328 and 60/829,327, which are specifically incorporated herein by reference.

Some examples of syntheses are provided below. To differentiate between the several generic groups of compounds in the examples herein, materials relating to formula (I) will be labeled as "Example of Synthesis Approach (I)-1" et seq., for formula (II) "Example of Synthesis Approach (II)-1" et seq., for formula (III), "Example of Synthesis Approach (III)-1 et seq., and for formula (I), "Example of Synthesis Approach (IV)-1, et seq.

Synthesis of Formula (I)

Compounds of formulae (I) can be prepared by processes scheme I, as disclosed in WO 01/60805 which is incorporated herein by reference:

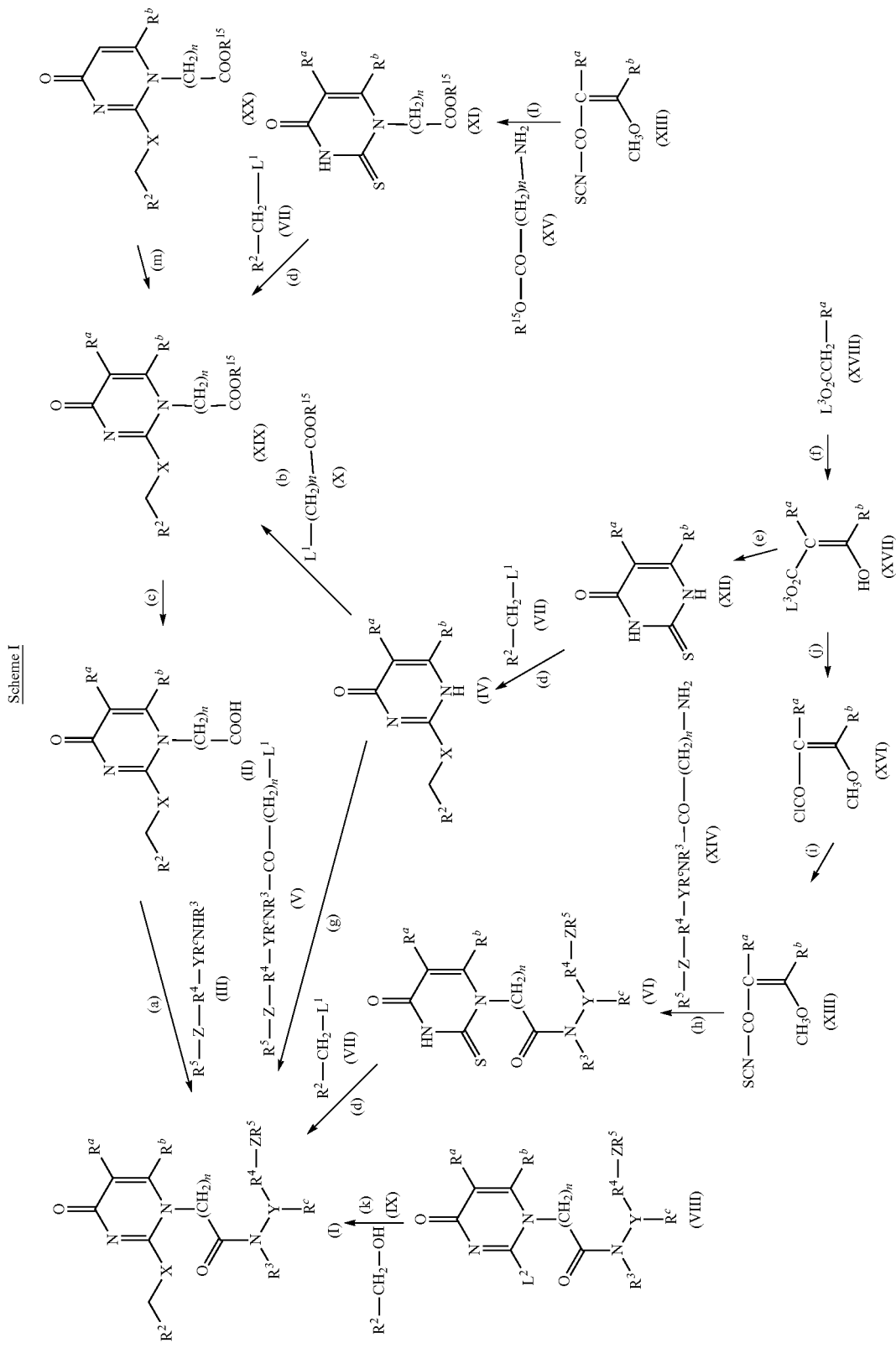

n which:

L³ is a $C_{(1-6)}$alkyl group, for instance methyl;
R¹⁵ is a $C_{(1-6)}$alkyl group, for instance ethyl or t-butyl and
L¹, L², Rᵃ, Rᵇ, Rᶜ, R², R³, R⁴, R⁵, n, X, Y and Z are as defined in WO 01/60805.

An exemplary reaction for making a compound of formula (I) of interest is as follows:

Example of Synthesis Approach (I)-1(a)

1-(N-(2-(Diethylamino)ethyl)-N-(4-(4-trifluoromethylphenyl)benzyl)aminocarbonyl-methyl)-2-(4-fluorobenzyl)thio-5,6-trimethylenepyrimidin-4-one

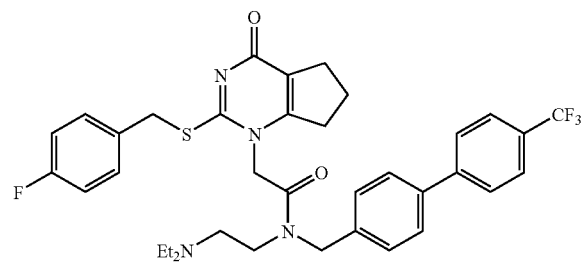

Intermediate B69 of WO 01/60805 (87.1 g, 0.26 mol.) was suspended in dichloromethane (2.9 liter). 1-Hydroxybenzotriazole hydrate (35.2 g, 0.26 mol.) and 1-(3-dimethylaminopropyl)-3-ethylcarbodiimide hydrochloride (99.7 g, 0.52 mol.) were added and the suspension stirred for 45 minutes by which time complete solution had been obtained. Intermediate A30 of WO 01/60805 (91.2 g, 0.26 mol.) was added as a solution in dichloromethane (100 ml) over 5 minutes and the solution stirred for 4 hours. Saturated ammonium chloride solution:water mixture (1:1, 1 liter) was added and the solution stirred for 10 minutes. The organic phase was separated and extracted with saturated ammonium chloride:water mixture (1:1, 1 liter), extracts were pH 6. The organic phase was separated and extracted with water (1 liter) containing acetic acid (10 ml), extract pH 5. The dichloromethane layer was separated and extracted with saturated sodium carbonate solution:water:saturated brine mixture (1:3:0.2, 1 liter), pH 10.5, then with saturated brine:water mixture (1:1, 1 liter). The brown solution was dried over anhydrous sodium sulfate in the presence of decolourising charcoal (35 g), filtered and the solvent removed in vacuo to give a dark brown foam. The foam was dissolved in iso-propyl acetate (100 ml) and the solvent removed in vacuo. The dark brown gummy residue was dissolved in boiling iso-propyl acetate (500 ml), cooled to room temperature, seeded and stirred overnight. The pale cream solid produced was filtered off and washed with iso-propyl acetate (100 ml). The solid was sucked dry in the sinter for 1 hour then recrystallized from iso-propyl acetate (400 ml). After stirring overnight the solid formed was filtered off, washed with iso-propyl acetate (80 ml) and dried in vacuo to give the title compound, 110 g, 63.5% yield. ¹H NMR (CDCl₃, ca 1.9:1 rotamer mixture) δ 0.99 (6H, t), 2.10 (2H, m), 2.50 (4H, q), 2.58/2.62 (2H, 2×t), 2.70/2.82 (2H, 2×t), 2.86 (2H, t), 3.28/3.58 (2H, 2×t), 4.45/4.52 (2H, 2×s), 4.68/4.70 (2H, 2×s), 4.93 (2H, s), 6.95 (2H, m), 7.31 (2H, d), 7.31/7.37 (2H, 2×m), 7.48/7.52 (2H, d), 7.65 (2H, m), 7.72 (2H, m); MS (APCI) (M+H)⁺ 667; mp 125° C. (by DSC—assymetric endotherm).

Example of Synthesis Approach (I)-1(b)

1-(N-(2-(Diethylamino)ethyl)-N-(4-(4-trifluoromethylphenyl)benzyl)aminocarbonyl-methyl)-2-(4-fluorobenzyl)thio-5,6-trimethylenepyrimidin-4-one bitartrate Prepared from intermediates A30 and B69 in WO 01/60805 by the method of Example 1 in WO 01/60805. ¹H-NMR (d₆-DMSO, ca 1:1 rotamer mixture) ☐ 0.92/0.99 (6H,2×t), 1.99 (2H, m), 2.54 (6H, m), 2.68/2.74 (4H, m), 3.36 (2H, m), 4.21 (2H, s), 4.37/4.44 (2H,2×s), 4,63/4.74 (2H,2× s), 4,89/5.13 (2H,2×s), 7.08/7.14 (2H,2×m), 7.36-7.50 (4H, m), 7.64/7.70 (2H,2×d), 7.83 (4H, m); MS (APCI+) found (M+1)=667; $C_{36}H_{38}F_4N_4O_2S$ requires 666.

Example of Synthesis Approach (I)-1(c)

1-(N-(2-(Diethylamino)ethyl)-N-(4-(4-trifluoromethylphenyl)benzyl)aminocarbonyl-methyl)-2-(4-fluorobenzyl)thio-5,6-trimethylenepyrimidin-4-one hydrochloride The free base from Example (I)-1(a) (3.00 g, 0.0045 mol) was suspended with stirring in isopropanol (30 ml) and warmed to 45° C. to give a clear solution. The solution was then cooled to ambient temperature and conc. hydrochloric acid (0.40 ml, 0.045 mol) was added. The resultant slurry was then stirred at ambient temperature for 35 minutes, before being cooled to 0° C. for 35 minutes. The slurry was then filtered and washed with isopropanol (10 ml), followed by heptane (30 ml), before being dried under vacuum to give the title compound as a white solid (3.00 g, 95%). ¹H NMR (CDCl₃) δ 1.38 (6H, t), 2.08 (2H, m), 2.82 (2H, t), 2.99 (2H, t), 3.19 (4H, m), 3.35 (2H, m), 3.97 (2H, s), 4.42 (2H, s), 4.81 (2H, s), 4.99 (2H, s), 6.87 (2H, t), 7.26 (2H, t), 7.33 (2H, d), 7.41 (2H, d), 7.53 (2H, d), 7.71 (2H, d), 11.91 (1H, s).

Synthesis of Formula (II)

A description of how to make the compounds of formula (II) and examples of intermediates and final products for the compounds named above can be found in published international application WO 02/30911, which is incorporated herein by reference. A last-step method for making a compound useful in this invention is Example (II)-1.

Example of Synthesis Approach (II)-1

N-(2-Diethylaminoethyl)-2-[2-(2-(2,3-difluorophenyl)ethyl)-4-oxo-4,5,6,7-tetrahydro-cyclopentapyrimidin-1-yl]-N-(4'-trifluoromethyl-biphenyl-4-ylmethyl)acetamide bitartrate

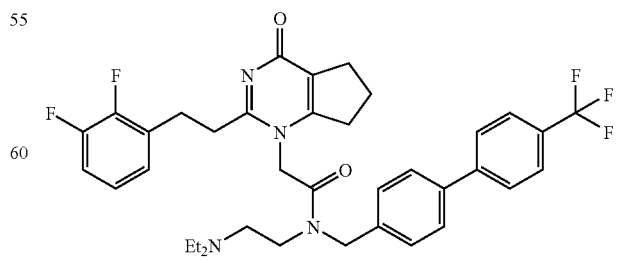

A solution of N,N-diethyl-N'-(4'-trifluoromethyl-biphenyl-4-ylmethyl)-ethane-1,2-diamine (Int D4 in WO 02/30911) (0.50 g, 1.44 mmol), 1-(3-dimethylaminopropyl)-3-ethylcarbodiimide (0.56 g, 1.45 mmol), 1-hydroxybenzotriazole hydrate (0.12 g) and 2-(2-[2-(2,3-difluorophenyl)-ethyl]-4-oxo-4,5,6,7-tetrahydro-cyclopentapyrimidin-1-yl)-acetic acid (Int C1 in WO 02/30911) (0.48 g, 1.44 mmol) in dichloromethane (10 ml) was stirred at ambient temperature overnight then diluted with dichloromethane (30 ml), washed with aqueous sodium bicarbonate and evaporated. The residue was purified by chromatography (10 g silica cartridge, ethyl acetate-acetone) to give the title compound as a yellow foam (free base) (0.50 g, 52%). $^1$H-NMR (DMSO, rotamer mixture) δ 0.83-0.89 (6H, m), 1.98 (2H, m), 2.40 (4H, m), 2.45-2.82 (10H, m), 3.02 (2H, m), 4.64/4.75 (2H,2×s), 4.96/5.19 (2H,2×s), 7.11-7.40 (5H, m), 7.65 (2H, m), 7.84 (4H, m); MS (APCI+) found (M+1)=667; $C_{37}H_{39}F_5N_4O_2$ requires 666.

d-Tartaric acid (0.09 g, 0.60 mmol) was added to a solution of the free base (0.40 g, 0.60 mmol) in methanol (10 ml) with stirring. The resulting solution was evaporated to yield the salt (0.49 g). $^1$H-NMR (DMSO, rotamer mixture) δ 0.85-0.97 (6H, m), 1.91-2.00 (2H, m), 2.40-2.49 (4H, m), 2.54-2.82 (10H, m), 3.02-3.46 (2H, m), 4.20 (2H, s), 4.64/4.75 (2H, 2×s), 4.97/5.18 (2H, 2×s), 7.11-7.40 (5H, m), 7.65 (2H, m), 7.84 (4H, m); MS (APCI+) found (M+1)=667; $C_{37}H_{39}F_5N_4O_2$ requires 666.

Following this process, or alternatively other processes described in WO 02/30911 (which is incorporated herein by reference), one can prepare the other compounds named above that have the structure of formula (II).

Synthesis of Formula (III)

The overall synthesis of compounds of formula (III) is illustrated in the following scheme III, as presented in WO02/30904 which is incorporated herein by reference:

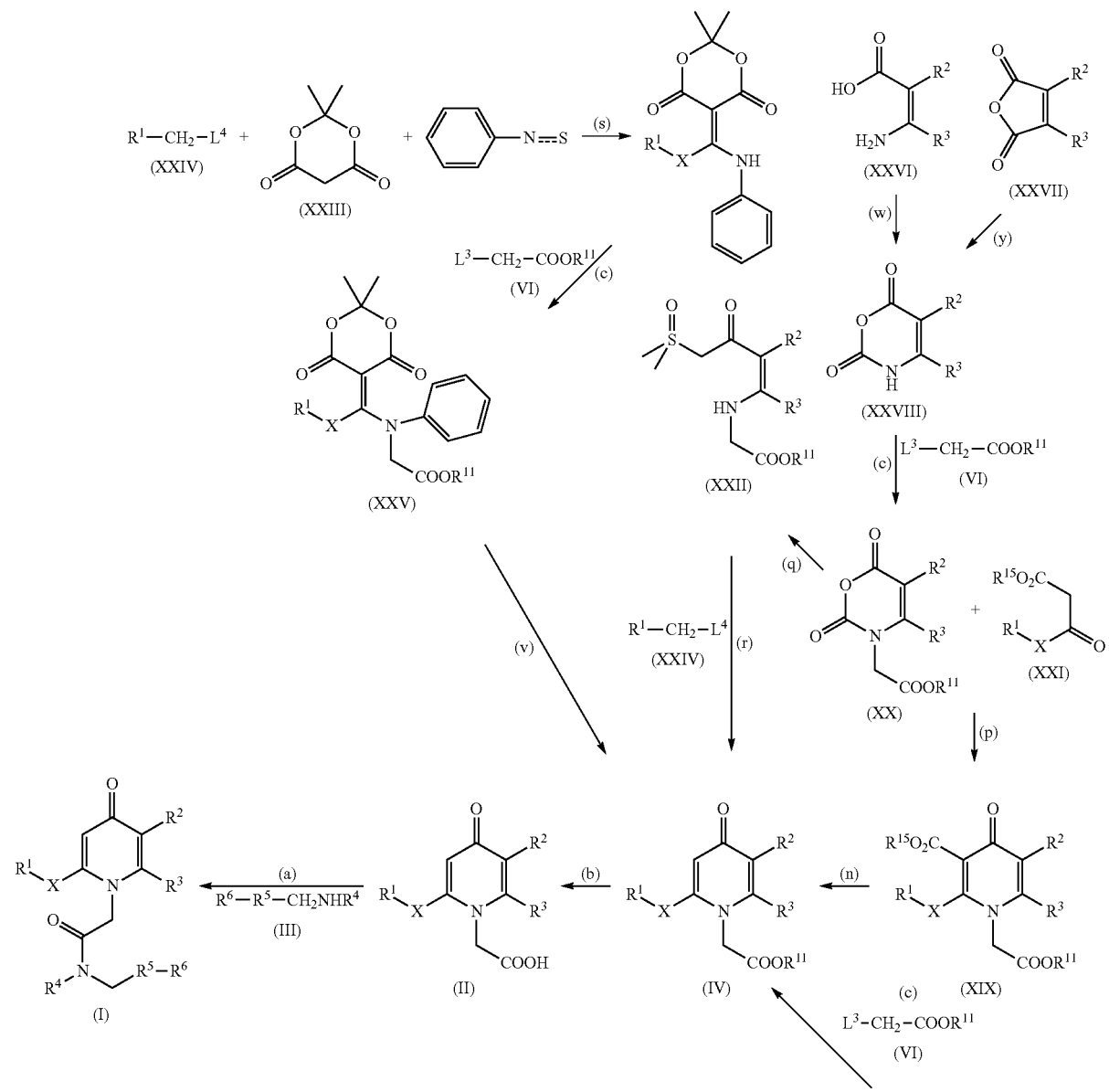

Scheme III

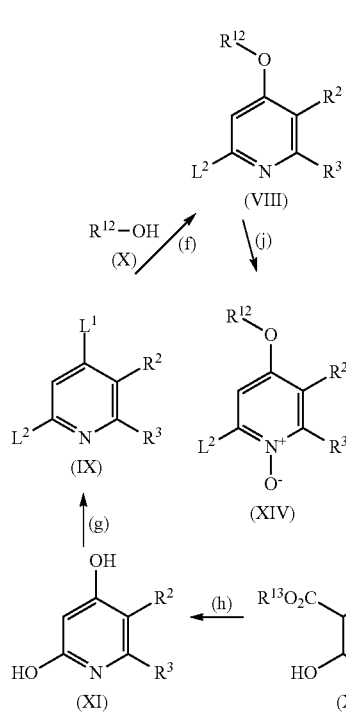
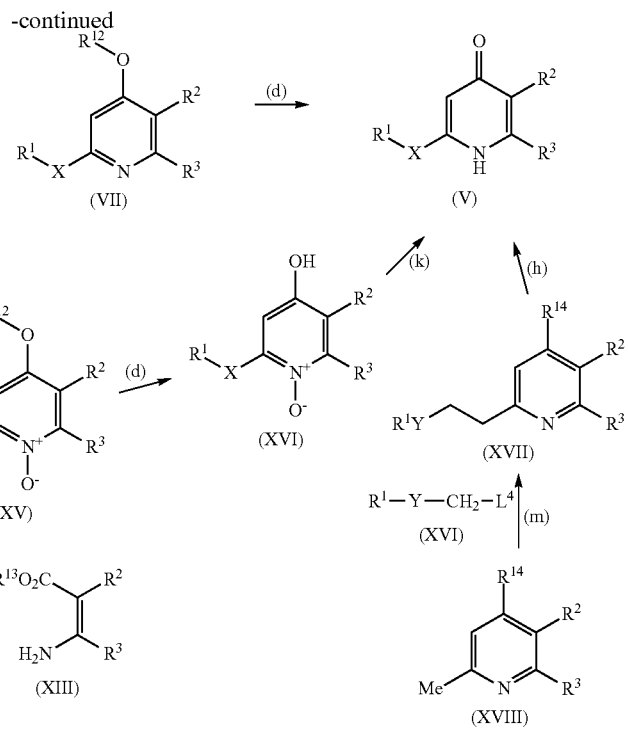

Referring to this scheme, the ester (IV) is usually prepared by N-1 alkylation of (V) using (VI), in which $R^{11}$ is as hereinbefore defined e.g. (VI) is t-butyl bromoacetate or ethyl bromoacetate, in the presence of a base e.g. BuLi in THF or sodium hydride in N-methyl pyrrolidinone (NMP) (step c).

When X is $CH_2S$, the key intermediate (IV) can be synthesised by reacting (XX) with dimethyloxosulfonium methylide, generated via the treatment of trimethylsulfoxonium iodide with sodium hydride at low temperature, to yield a sulfur ylid (XXII) (step q). Subsequent treatment of (XXII) with carbon disulfide in the presence of diisopropylamine, followed by $R^1CH_2$-$L^4$, where $L^4$ is a leaving group, yields intermediate (IV) (step r).

Alternatively, when X is $CH_2S$, the $R^1X$ substituent can be introduced by displacement of a leaving group $L^2$ (e.g. Cl) (step e) either on a pyridine (VIII) or pyridine N-oxide (XIV), to give 2-substituted pyridines (VII) and (XV). Transformation of (VII) or (XV) to the 4-pyridone (V) is accomplished by deprotection of the 4-oxygen (e.g. using $(Ph_3P)_3RhCl$ when in aq. ethanol when $R^{12}$=allyl) (step d), followed, for (XVI), by removal of the N-oxide substituent, using hydrogen in the presence of Pd/C in acetic acid (step k). The pyridine (VIII) or pyridine N-oxide (XIV) can be prepared by steps (i), (h), (g), (f), and (j), in which:

(j) treatment of (VIII) with m-chloroperbenzoic acid in dichloromethane;

(f) treatment of (IX) with $R^{12}OH(X)$, in which $R^{12}$ is allyl, and sodium hydride in DMF;

(g) treatment of (XI) with phosphorus oxychloride;

(h) treatment of (XII) with aq HCl with heating;

(i) treatment of (XIII) with di-lower alkyl malonate and sodium alkoxide in alcohol (in which $R^{13}$ is $C_{(1-6)}$alkyl, typically $R^{13}$=Et); and $R^1$—$CH_2SH$(XIX) is typically prepared from the thioacetate, which is formed from the corresponding alkyl bromide $R_1$—$CH_2Br$.

Alternatively, when X is $CH_2S$ and $R^2$ and $R^3$, together with the pyridone ring carbon atoms to which they are attached, form a fused benzo ring, intermediate (IV) can be synthesised from known starting materials by steps (s), (c) and (v) in which:

(s) treatment of Meldrum's acid (XXIII) with sodium hydride at low temperature, followed by reaction with phenylisothiocyanate and subsequent treatment with $R^1CH_2$-$L^4$;

(c) as hereinbefore discussed;

(v) treatment of (XXV) with trifluoroacetic acid.

When X is alkylene, it is preferable to use steps (m) and (h) (intermediates (XVII), (XVIII)) or steps (n) and (p) (intermediates (XIX), (XX), (XXI)) in which:

(h) transformation of a 4-substituted pyridine into a 4-pyridone e.g. by treatment of (XVII) $R^{14}$=Cl with aq HCl and dioxan, or deprotection of $R^{14}$=$OR^{12}$, e.g. using conditions of step (d).

(m) chain extension of a 2-alkyl pyridine, e.g. where X=$YCH_2CH_2$ by treatment of a 2-methylpyridine (XVIII) with $R^1$—Y—$CH_2$-$L^4$ (XVI) in which $L^4$ is a leaving group and a strong base, such as BuLi, in THF.

In the alternative route, the 3-ester group is removed from intermediate (XIX) $R^{15}$=$C_{(1-6)}$alkyl by heating in diphenyl ether where $R^{15}$=tBu (step n); Intermediate (XIX) is formed from the 2,6-dioxo-1,3-oxazine (XX) and ester (XXI) by treatment with a base such as NaH in DMF or 1,8-diazabicyclo[5.4.0]undec-7-ene in dichloromethane.

Synthesis of (XX) from known starting materials can be achieved via steps (w) and (c) or steps (y) and (c) in which:

(w) treatment of (XXVII) with azidotrimethylsilane in THF;

(y) treatment of (XXVI) with phosgene;

(c) as hereinbefore described.

See WO02/30904, which is incorporated herein by reference, for additional details and exposition of how to make compounds of formula (III).

Example of Synthesis Approach (III)-1

N-(1-(2-Methoxyethyl)piperidin-4-yl)-2-[2-(2,3-difluorobenzylthio)-4-oxo-4H-quinolin-1-yl]-N-(4'-trifluoromethylbiphenyl-4-ylmethyl)acetamide

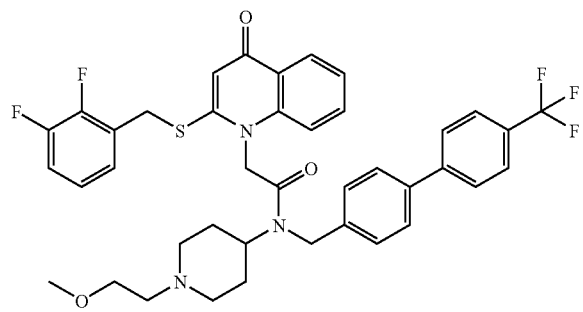 [SMILES: COCCN1CCC(N(Cc2ccc(-c3ccc(C(F)(F)F)cc3)cc2)C(=O)Cn2c(SCc3cccc(F)c3F)cc(=O)c3ccccc32)CC1]

The free base was prepared from Int. E1 and Int. A42 by the method of Example 1 in WO 02/30904, except using DMF as solvent in place of dichloromethane. 1.97 g of this material was crystallised from n.butyl acetate (10 ml) to give the title compound (1.35 g). $^1$H-NMR (CD$_3$OD) δ 1.7-2.05 (4H, m), 2.05-2.3 (2H, 2×t), 2.5-2.65 (2H, m), 2.95-3.1 (2H, m), 3.3 (3H, s), 3.45-3.55 (2H, m), 3.9-4.05+4.4-4.5 (1H, 2×m), 4.37+4.48 (2H, 2×s), 4.71+4.87 (2H, 2×br s), 5.31+5.68 (2H, 2×s), 6.44+6.52 (1H, 2×s), 6.95-7.3 (3H, m), 7.35-7.85 (11H, m), 8.2-8.35 (1H, m); MS (APCI+) found (M+1) 736; C$_{40}$H$_{38}$F$_5$N$_3$O$_3$S requires 735.

Synthesis of Formula (IV)

The following flow chart illustrates a process for making the compounds of this invention.

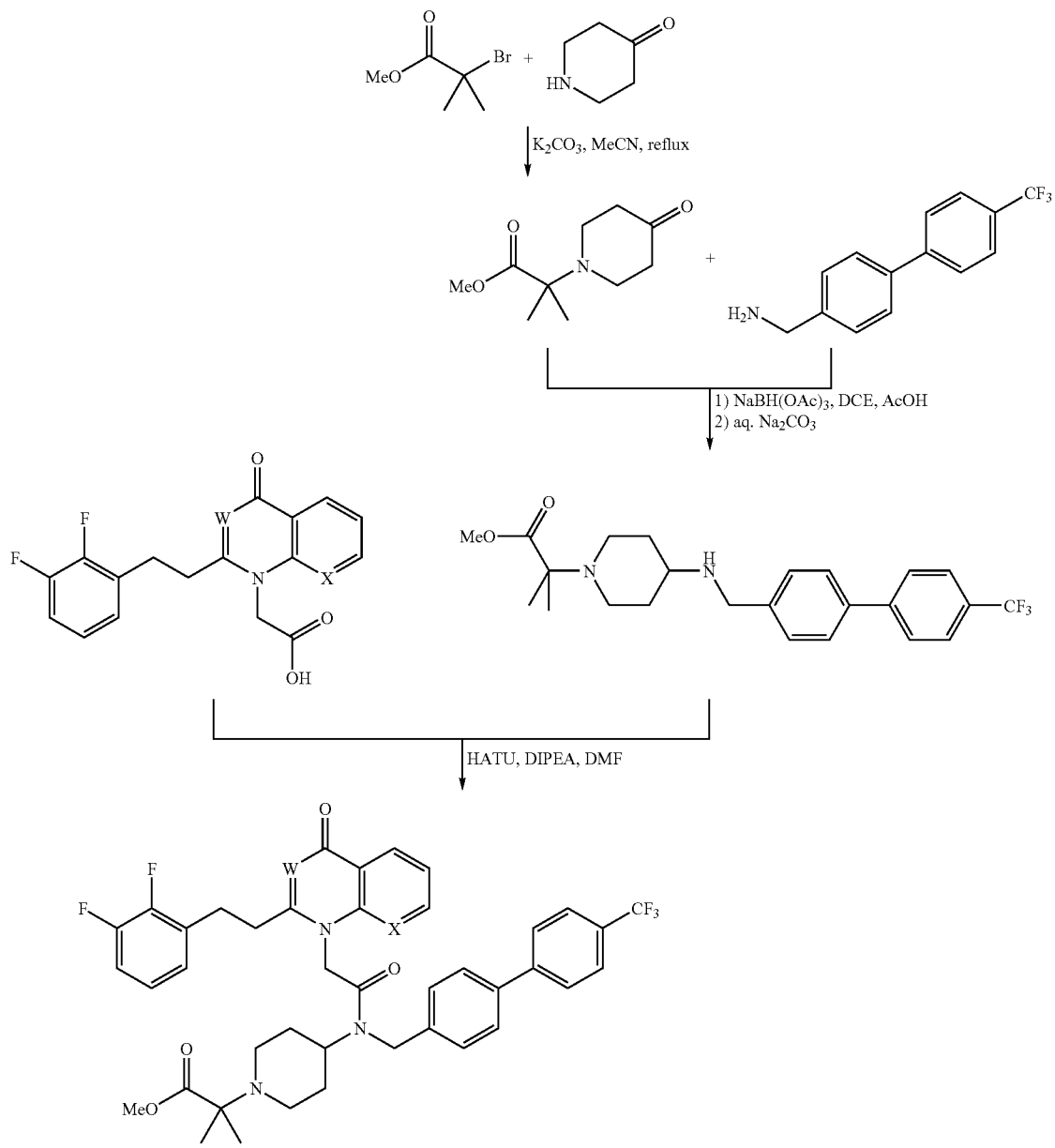

In addition, the reader is referred to published PCT application WO 03/016287, which is incorporated herein by reference for chemistries that can be useful in preparing some of the intermediates set out in this flow chart. Those chemistries, to the extent they are useful in this case, are incorporated herein by reference as though it was fully set out herein. In addition, reference is made to the syntheses set out in published PCT applications WO 01/60805, WO 02/30911, WO 02/30904, WO 03/042218, WO 03/042206, WO 03/041712, WO 03/086400, and WO 03/87088, and co-pending U.S. provisional applications 60/829,328 and 60/829,327 both filed 13 Oct. 2006 noted above, which are incorporated herein by reference. To the extent the reader wishes to prepare the compounds of formula (IV) by using intermediates, reagents, solvents, times, temperatures, etc., other than those in the route on the foregoing page, these published PCT applications and co-pending US applications can provide useful guidance. To the extent the chemistries in these applications are pertinent to making the instant compounds, those materials are incorporated herein by reference.

Intermediate (IV)-A1 {[4'-(Trifluoromethyl)-4-biphenylyl]methyl}amine

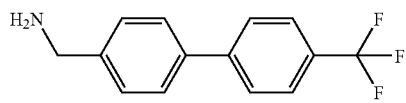 [SMILES: NCc1ccc(-c2ccc(C(F)(F)F)cc2)cc1]

The preparation of this compound was described in WO 02/30911 as Intermediate D7.

Intermediate (IV)-A2 ({4'-[(Trifluoromethyl)oxy]-4-biphenylyl}methyl)amine hydrochloride

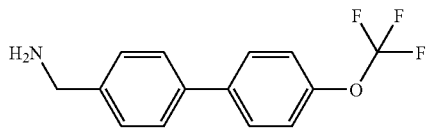 [SMILES: NCc1ccc(-c2ccc(OC(F)(F)F)cc2)cc1]

A solution of 4'-[(trifluoromethyl)oxy]-4-biphenylcarbonitrile (prepared from {4-[(trifluoromethyl)oxy]phenyl}boronic acid by a method analogous to that described for the 4'-trifluoromethyl analogue, Intermediate D6 of WO 02/30911) (66.6 g) in ethanol (2000 ml) and concentrated hydrochloric acid (100 ml) was hydrogenated over Pearlman's catalyst (10 g) at 25 psi until reduction was complete. The catalyst was removed by filtration through celite, then the solvent was removed in vacuo to obtain the desired product.

LCMS Rt=2.212 minutes; m/z [M+H]$^+$=251.0

Intermediates for Making Formula (IV)

Intermediate (IV)-A3

Methyl 2-methyl-2-(4-oxo-1-piperidinyl)propanoate

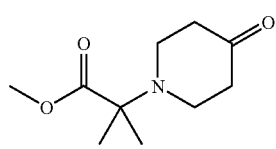

A mixture of methyl 2-bromo-2-methylpropanoate (80.87 ml, 5 equiv), 4-piperidone hydrochloride monohydrate (19.6 g, 1 equiv), acetonitrile (200 ml) and potassium carbonate (69.1 g, 4 equiv) was heated at reflux under nitrogen with mechanical stirring for 17.5 h then cooled in an ice bath before adding diethyl ether (100 ml). Filtration through celite followed by flash chromatography (silica, 10-50% ethyl acetate in hexane) and evaporation of the product fractions gave the desired product as a yellow oil (14.28 g).

$^1$H NMR (CDCl$_3$) δ 1.41 (6H,s), 2.47 (4H,m), 2.88 (4H,m), 3.73 (3H,s).

Intermediate (IV)-A4

Ethyl 2-methyl-2-(4-oxo-1-piperidinyl)propanoate

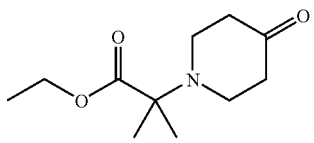

A mixture of ethyl 2-bromo-2-methylpropanoate (48.3 ml, 5 equiv), 4-piperidone hydrochloride monohydrate (100 g, 1 equiv), acetonitrile (1216 ml) and potassium carbonate (353 g, 4 equiv) was heated at reflux under nitrogen with mechanical stirring for 20 h then cooled in an ice bath before adding diethyl ether (approx. 1400 ml). The mixture was filtered through celite, evaporated in vacuo, then excess bromoester distilled off (50° C. still head temperature/10 Torr). Flash chromatography (silica, 5-30% ethyl acetate in hexane) and evaporation of the product fractions gave the crude product as a yellow oil. To remove some remaining bromoester contaminant this was partitioned between ethyl acetate and 2M aqueous hydrochloric acid. The organic layer was discarded and the aqueous layer was basified with sodium carbonate, saturated with sodium chloride and extracted with ethyl acetate. Drying and evaporation of the organic extracts gave the desired product as a yellow oil (54.7 g).

$^1$H NMR (CDCl$_3$) δ 1.27 (3H,t), 1.40 (6H,s), 2.47 (4H,m), 2.90 (4H,m), 4.20 (2H,q).

Intermediate (IV)-A5

1,1-Dimethylethyl 2-methyl-2-(4-oxo-1-piperidinyl)propanoate

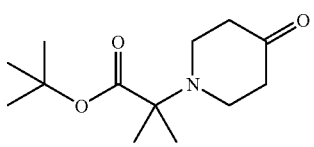 [SMILES: CC(C)(C)OC(=O)C(C)(C)N1CCC(=O)CC1]

A mixture of 1,1-dimethylethyl 2-bromo-2-methylpropanoate (8.0 g, 1.1 equiv), 4-piperidone hydrochloride (5.0 g, 1 equiv), acetone (50 ml) and potassium carbonate (13.0 g, 3 equiv) was heated at reflux with stirring for 24 h, then filtered and the filtrate evaporated. The crude residue was used in the next step without purification.

ES+MS m/z [M+H−tBu]$^+$=186.1

Intermediate (IV)-B1

Methyl 2-methyl-2-[4-({[4'-(trifluoromethyl)-4-biphenylyl]methyl}amino)-1-piperidinyl]propanoate

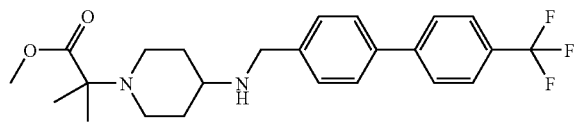 [SMILES: COC(=O)C(C)(C)N1CCC(NCc2ccc(-c3ccc(C(F)(F)F)cc3)cc2)CC1]

A mixture of methyl 2-methyl-2-(4-oxo-1-piperidinyl)propanoate (Int. A3) (14.28 g, 1 equiv), {[4'-(trifluoromethyl)-4-biphenylyl]methyl}amine (Int. A1) (19.6 g, 0.85 equiv), DCE (300 ml), acetic acid (3.8 ml, 0.90 equiv) and sodium triacetoxyborohydride (20.7 g, 1.25 equiv) was stirred at room temperature under nitrogen for 17.5 h. Aqueous sodium carbonate (2M solution, excess) was added and stirred for 4 h, then the mixture was extracted with a mixture of diethyl ether and THF. The organic extracts were backwashed with water and brine, dried over sodium sulfate and filterered through a pad of silica gel which was rinsed with 2.5% methanol in DCM. After evaporation in vacuo, the crude product was crystallised from ether/hexane, finally at ice bath temperature, which after drying yielded a white solid (20.9 g).

LCMS Rt=2.070 minutes; m/z [M+H]$^+$=435.2

$^1$H NMR (d$_6$-DMSO) δ 1.15-1.32 (8H, m), 1.75-187(2H, m), 1.97-2.12 (2H,m), 2.27-2.40 (1H, m), 2.77-2.90 (2H,m), 3.60 (3H,s), 3.76 (2H,s), 7.46 (2H, d, J=8.03 Hz), 7.67 (2H, d, J=8.28 Hz), 7.80 (2H, d, J=8.53 Hz), 7.88 (2H, d, 8.03 Hz)

Intermediate (IV)-B2

Ethyl 2-methyl-2-[4-({[4'-(trifluoromethyl)-4-biphenylyl]methyl}amino)-1-piperidinyl]propanoate

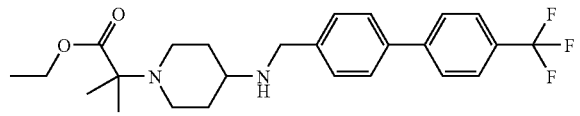 [SMILES: CCOC(=O)C(C)(C)N1CCC(NCc2ccc(-c3ccc(C(F)(F)F)cc3)cc2)CC1]

A mixture of ethyl 2-methyl-2-(4-oxo-1-piperidinyl)propanoate (Int. A4) (25.6 g, 1.2 equiv), {[4'-(trifluoromethyl)-4-biphenylyl]methyl}amine (Int. A1) (31.1 g, 1.0 equiv), DCE (400 ml) and acetic acid (6.3 ml, 1.1 equiv) was stirred at room temperature under nitrogen. Sodium triacetoxyborohydride (33.5 g, 1.5 equiv) was added and stirring continued for 19 hours. Aqueous sodium carbonate (2M solution, excess) was added and stirred for 1.5 h, then the mixture was extracted with a mixture of diethyl ether and THF. The organic extracts were backwashed with water and brine, filterered through a pad of silica gel, dried over sodium sulfate and evaporated in vacuo. The desired product was obtained as a white solid (44.2 g) which was used without further purification.

LCMS Rt=2.194 minutes; m/z [M+H]$^+$=449.3

$^1$H NMR (d$_6$-DMSO) δ 1.06-1.32 (1H,m), 1.74-1.89 (2H, m), 1.99-2.14 (2H, m), 2.25-2.39 (1H, m), 2.69-2.89 (2H, m), 3.75 (2H, s), 4.01-4.12 (2H, m), 7.45 (2H, d, J=7.55 Hz), 7.67 (2H, d, J=7.81 Hz), 7.79 (2H, d, J=8.06 Hz), 7.88 (2H, d, J=8.06 Hz)

Intermediate (IV)-B3

Ethyl 2-methyl-2-{4-[({4'-[(trifluoromethyl)oxy]-4-biphenylyl}methyl)amino]-1-piperidinyl}propanoate

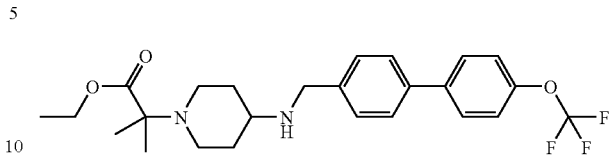

A mixture of ethyl 2-methyl-2-(4-oxo-1-piperidinyl)propanoate (Int. A4) (1.09 g, 1.2 equiv), ({4'-[(trifluoromethyl)oxy]-4-biphenylyl}methyl)amine hydrochloride (Int. A2) (1.28 g, 1.0 equiv), DCE (21 ml) and acetic acid (0.27 ml, 1.1 equiv) was stirred at room temperature under nitrogen. Sodium triacetoxyborohydride (1.42 g, 1.5 equiv) was added and stirring continued for 3 hours. Aqueous sodium carbonate (2M solution, excess) was added and stirred for 45 min, then the mixture was partitioned with a mixture of diethyl ether/THF and water. The organic extracts were backwashed with water and brine, and dried over sodium sulfate and evaporated in vacuo. The desired product was obtained as a light yellow solid (2.14 g) which was used without further purification.

LCMS Rt=2.244 minutes; m/z [M+H]$^+$=465.3

Intermediate (IV)-B4

1,1-Dimethylethyl 2-methyl-2-[4-({[4'-(trifluoromethyl)-4-biphenylyl]methyl}amino)-1-piperidinyl]propanoate

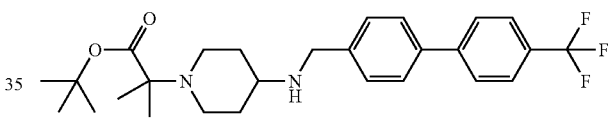

A mixture of 1,1-dimethylethyl 2-methyl-2-(4-oxo-1-piperidinyl)propanoate (Int. A6) (370 mg, 1.2 equiv), {[4'-(trifluoromethyl)-4-biphenylyl]methyl}amine (Int. A1) (397 mg, 1 equiv), sodium triacetoxyborohydride (400 mg, 1.5 equiv), DCM (10 ml) and acetic acid (0.076 ml, 1 equiv) was combined and stirred at room temperature until LCMS confirmed disappearance of the amine starting material (approx. 18 hours). Aqueous sodium carbonate was added and then extracted with DCM. The organics were dried over sodium sulfate and concentrated to give a solid (420 mg) that was used without further purification.

LCMS Rt=2.24 minutes; m/z [M+H]$^+$=477.3

Intermediate (IV)-C1

[2-[2-(2,3-Difluorophenyl)ethyl]-4-oxo-1(4H)-quinazolinyl]acetic acid

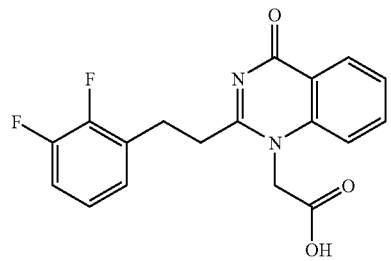 [SMILES: O=C(O)Cn1c(CCc2cccc(F)c2F)nc(=O)c2ccccc21]

The preparation of this compound was described in WO 02/30911 as Intermediate C43.

Intermediate (IV)-C2

[2-[2-(2,3-Difluorophenyl)ethyl]-4-oxo-1,8-naphthyridin-1(4H)-yl]acetic acid

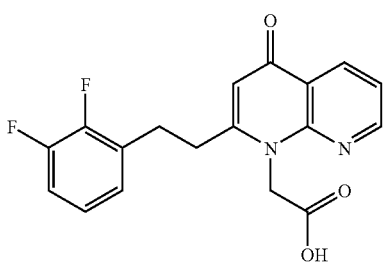 [SMILES: O=C(O)Cn1c(CCc2cccc(F)c2F)cc(=O)c2cccnc21]

The preparation of this compound was described in WO 02/30904 as Intermediate E21.

Intermediate (IV)-C3

[2-[2-(2,4-Difluorophenyl)ethyl]-4-oxo-1(4H)-quinazolinyl]acetic acid

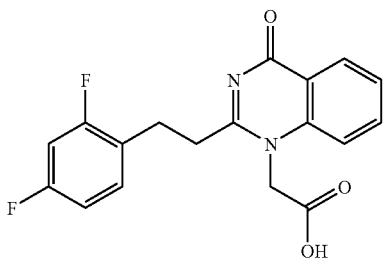 [SMILES: O=C(O)Cn1c(CCc2ccc(F)cc2F)nc(=O)c2ccccc21]

The preparation of this compound was described in WO 02/30911 as Intermediate C45.

Intermediate (IV)-C4

Ethyl [2-[2-(2,4-difluorophenyl)ethyl]-4-oxopyrido[2,3-d]pyrimidin-1(4H)-yl]acetate

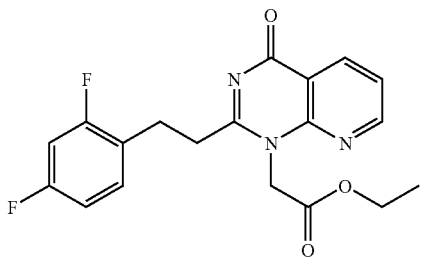 [SMILES: CCOC(=O)Cn1c(CCc2ccc(F)cc2F)nc(=O)c2cccnc21]

A mixture of ethyl (2,4-dioxo-3,4-dihydropyrido[2,3-d]pyrimidin-1(2H)-yl)acetate (WO 02/30911, Intermediate B52) (40.8 g, 1.2 equiv) and 3-(2,4-difluorophenyl)propanimidamide (made by methods analogous to those described for the 2,3-difluoro isomer, Intermediates A1 to A3 of WO 02/30911) (30.0 g, 1 equiv) was fused in a 150° C. oil bath for 25 min, then cooled quickly to room temperature in a water bath. Chromatography (silica, crude product loaded in DCM and eluted with 50-100% ethyl acetate in hexane) gave the desired product (43.56 g).

LCMS Rt=2.521 minutes; m/z [M+H]$^+$=374.1

$^1$H NMR (CDCl$_3$) δ 1.31 (3H, t), 3.13 (2H, m), 3.26 (2H, m), 4.28 (2H, q), 5.27 (2H, s), 6.82 (2H, m), 7.34 (1H, m), 7.50 (1H, m), 8.65 (1H, m), 8.74 (1H, m).

Intermediate (IV)-C5

[2-[2-(2,3-Difluorophenyl)ethyl]-4-oxopyrido[2,3-d]pyrimidin-1(4H)-yl]acetic acid

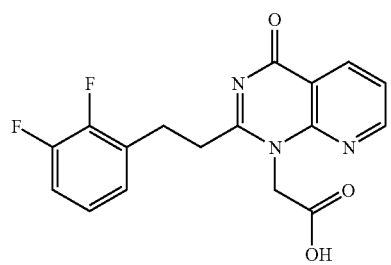 [SMILES: O=C(O)Cn1c(CCc2cccc(F)c2F)nc(=O)c2cccnc21]

The preparation of this compound was described in WO 02/30911 as Intermediate C35.

Intermediate (IV)-C5

[2-[2-(2,4-Difluorophenyl)ethyl]-4-oxopyrido[2,3-d]pyrimidin-1(4H)-yl]acetic acid

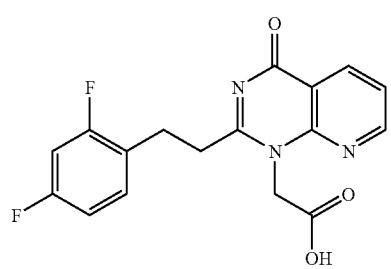 [SMILES: O=C(O)Cn1c(CCc2ccc(F)cc2F)nc(=O)c2cccnc21]

Ethyl [2-[2-(2,4-difluorophenyl)ethyl]-4-oxopyrido[2,3-d]pyrimidin-1(4H)-yl]acetate (Int. C1) (32.76 g, 1 equiv) was dissolved in ethanol (350 ml) and water (70 ml), cooled in ice, then aqueous lithium hydroxide (2M solution, 43.42 ml, 0.99 equiv) was added. Stirring was continued for 2 h at room temperature. The solution was concentrated in vacuo and the residue was redissolved in water (700 ml) and saturated aqueous sodium bicarbonate (50 ml), then washed with ethyl acetate (200 ml). The aqueous layer was acidified to pH 2 with 2M hydrochloric acid, and the precipitate was filtered off, washed with ice water (50 ml) and dried in vacuo (50° C., 16 h) to obtain the desired product (23.2 g).

$^1$H NMR (d$_6$-DMSO) δ 2.4-2.6 (4H, m), 5.24 (2H, s), 7.04 (1H, m), 7.22 (1H, m), 7.48 (1H, m), 7.60 (1H, m), 8.47 (1H, m), 8.84 (1H, m).

EXAMPLE (IV)-1

Methyl 2-[4-({[2-[2-(2,3-difluorophenyl)ethyl]-4-oxo-1(4H)-quinazolinyl]acetyl}{[4'-(trifluoromethyl)-4-biphenylyl]methyl}amino)-1-piperidinyl]-2-methylpropanoate 2,3-dihydroxybutanedioate (salt)

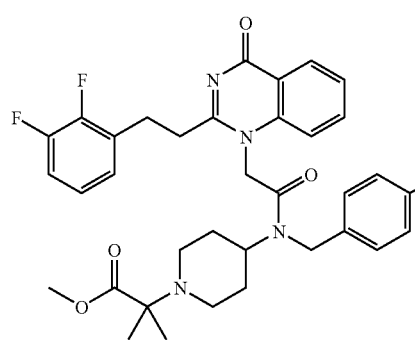

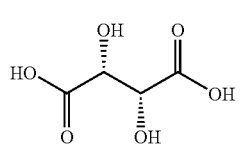

A mixture of [2-[2-(2,3-difluorophenyl)ethyl]-4-oxo-1(4H)-quinazolinyl]acetic acid (Int. C1) (100 mg, 1 equiv), methyl 2-methyl-2-[4-({[4'-(trifluoromethyl)-4-biphenylyl]methyl}amino)-1-piperidinyl]propanoate (Int. B1) (130 mg, 1.03 equiv), DIPEA (0.1 ml, 3.6 equiv), acetonitrile (2 ml) and HATU (130 mg, 1.4 equiv) was stirred at room temperature for 1 h, then evaporated and redissolved in acetonitrile. Purification by reverse phase HPLC (Preparative Method A) gave methyl 2-[4-({[2-[2-(2,3-difluorophenyl)ethyl]-4-oxo-1(4H)-quinazolinyl]acetyl}{[4'-(trifluoromethyl)-4-biphenylyl]methyl}amino)-1-piperidinyl]-2-methylpropanoate (128 mg).

LCMS Rt=2.686 minutes; m/z [M+H]$^+$=761.3

$^1$H NMR (CDCl$_3$) δ 1.33 (3H, s), 1.36 (3H, s), 1.83-2.02 (4H, m), 2.36-2.48 (2H, m), 2.87-2.91 (1H, m), 3.06-3.09 (2H, m), 3.16-3.20 (2H, m), 3.26-3.29 (1H, m), 3.71-3.73 (3H, m), 4.02/4.51 (1H, 2×br m), 4.74 (1H, s), 4.92 (1H, s), 5.12 (1H, s), 5.56 (1H, s), 7.00-7.19 (3H, m), 7.32-7.37 (1H, m), 7.48-7.62 (5H, m), 7.72-7.81 (5H, m), 8.22-8.28 (1H, m).

The free base was converted to the bitartrate salt by adding L-tartaric acid (1.675 g, 1.0 equiv) in one portion and stirred for 30 minutes at room temperature. The solution was concentrated in vacuo to an off-white powder that was dried in a vacuum oven at room temperature.

Example of Synthesis Approach (IV)-2

Methyl 2-[4-({[2-[2-(2,3-difluorophenyl)ethyl]-4-oxo-1,8-naphthyridin-1(4H)-yl]acetyl}-{[4'-(trifluoromethyl)-4-biphenylyl]methyl}amino)-1-piperidinyl]-2-methylpropanoate 2,3-dihydroxybutanedioate (salt)

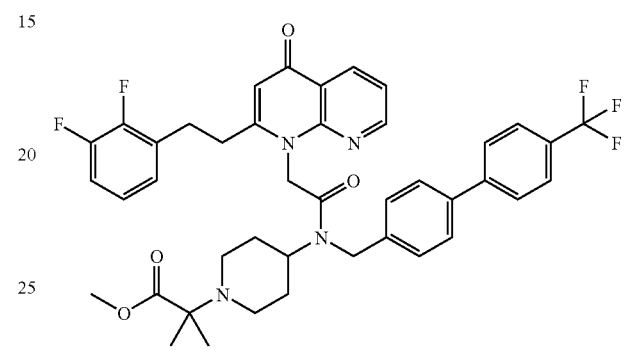

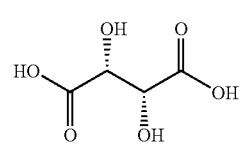

A mixture of [2-[2-(2,3-difluorophenyl)ethyl]-4-oxo-1,8-naphthyridin-1(4H)-yl]acetic acid (Int. C2) (100 mg, 1 equiv), carbonyldiimidazole (50 mg, 1.05 equiv) and dimethyl-acetamide (4 ml) was stirred at 60° C. for 30 min then methyl 2-methyl-2-[4-({[4'-(trifluoro-methyl)-4-biphenylyl]methyl}amino)-1-piperidinyl]propanoate (Int. B1) (132 mg, 1.05 equiv) was added and the temperature raised to 80° C. for 2 h. A further portion of carbonyldiimidazole (0.5 equiv) was added and stirring continued at 80° C. for 15 h. After cooling the crude mixture was applied to reverse phase HPLC (Preparative Method A) to obtain methyl 2-[4-({[2-[2-(2,3-difluorophenyl)ethyl]-4-oxo-1,8-naphthyridin-1(4H)-yl]-acetyl}{[4'-(trifluoromethyl)-4-biphenylyl]methyl}amino)-1-piperidinyl]-2-methyl-propanoate (99 mg).

LCMS Rt=2.845 minutes; m/z [M+H]$^+$=761.3

$^1$H NMR (CDCl$_3$) δ 1.28 (3H, s), 1.31 (3H, s), 1.73-2.05 (4H, m), 2.25 (1H, t), 2.39-2.46 (1H, m), 2.96-2.99 (1H, m), 3.00-3.12 (4H, m), 3.19 (1H, s), 3.68-3.73 (3H, m), 4.11/4.41 (1H, 2×br m), 4.73 (1H, s), 4.97 (1H, s), 5.51 (1H, s), 6.29-6.34 (1H, m), 7.06-7.20 (2H, m), 7.35-7.41 (1H, m), 7.48-7.58 (2H, m), 7.68-7.84 (6H, m), 8.60-8.68 (1H, m), 8.87-8.91 (1H, m).

This was converted to the bitartrate salt by a method analogous to that described for Example of Synthesis Approach (I).

Example of Synthesis Approach (IV)-3

Ethyl 2-[4-({[2-[2-(2,3-difluorophenyl)ethyl]-4-oxo-1(4H)-quinazolinyl]acetyl}{[4'-(trifluoromethyl)-4-biphenylyl]methyl}amino)-1-piperidinyl]-2-methyl-propanoate 2,3-dihydroxybutanedioate (salt)

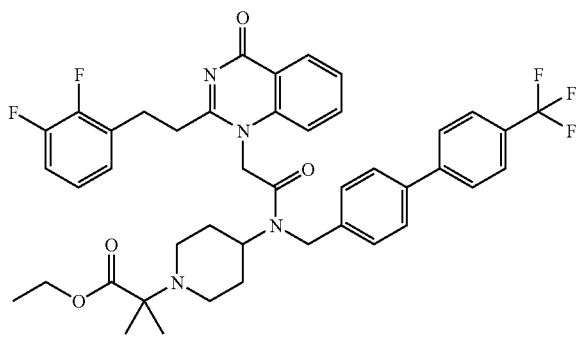

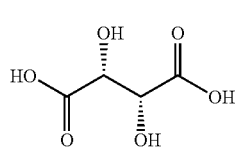

A mixture of [2-[2-(2,3-difluorophenyl)ethyl]-4-oxo-1(4H)-quinazolinyl]acetic acid (Int. C1) (115 mg, 1 equiv), ethyl 2-methyl-2-[4-({[4'-(trifluoromethyl)-4-biphenylyl]methyl}amino)-1-piperidinyl]propanoate (Int. B2) (150 mg, 1 equiv), HATU (51 mg, 1.2 equiv), DMF (2.7 ml) and DIPEA (0.17 ml, 3 equiv) was shaken at room temperature for 5 h. The reaction mixture was partitioned between ethyl acetate/methanol and aqueous sodium bicarbonate, then the organic layer was brine-washed and dried. Flash chromatography (silica, 3-4% methanol in DCM) gave ethyl 2-[4-({[2-[2-(2,3-difluorophenyl)ethyl]-4-oxopyrido[2,3-d]pyrimidin-1(4H)-yl]acetyl}{[4'-(trifluoromethyl)-4-biphenylyl]methyl}amino)-1-piperidinyl]-2-methylpropanoate as a white solid (190 mg).

LCMS Rt=2.55 minutes; m/z [M+H]$^+$=775.3

$^1$H NMR (CDCl$_3$) δ 1.18-1.40 (9H, m), 1.61-2.09 (4H, m), 2.22-2.45 (2H, m), 2.75-2.85 (1H, m), 2.90-3.34 (5H, m), 3.71/4.66 (1H, 2×m), 4.12-4.26 (2H, m), 4.70-4.85 (3H, m), 5.08 (1H, s), 6.80-6.88 (1H,m), 6.95-7.13 (3H, m), 7.27-7.33 (1H, m), 7.34-7.52 (3H,m), 7.56-7.62 (1H, m), 7.63-7.77 (4H, m), 8.29-8.44 (2H, m).

This was converted to the bitartrate salt by a method analogous to that described in Example of Synthesis Approach (I).

Example of Synthesis Approach (IV)-4

Ethyl 2-{4-[{[2-[2-(2,3-difluorophenyl)ethyl]-4-oxo-1(4H)-quinazolinyl]acetyl}({4'-[(trifluoromethyl)oxy]-4-biphenylyl}methyl)amino]-1-piperidinyl}-2-methylpropanoate 2,3-dihydroxybutanedioate (salt)

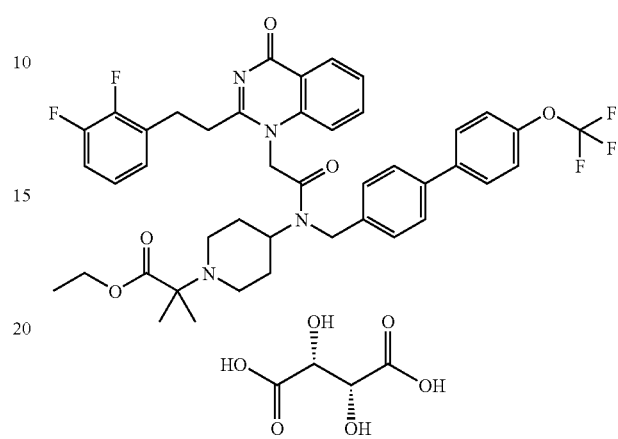

A mixture of [2-[2-(2,3-difluorophenyl)ethyl]-4-oxo-1(4H)-quinazolinyl]acetic acid (Int. C1) (124 mg, 1.2 equiv), ethyl 2-methyl-2-{4-[({4'-[(trifluoromethyl)oxy]-4-biphenylyl}methyl)amino]-1-piperidinyl}propanoate (Int. B3) (139 mg, 1 equiv), DMF (1.2 ml) and DIPEA (0.16 ml, 3 equiv) was shaken at room temperature for 30 min, then HATU (176 mg, 1.5 equiv) was added and shaking continued for 4 h. Reverse phase HPLC (Preparative Method B) gave ethyl 2-{4-[{[2-[2-(2,3-difluorophenyl)ethyl]-4-oxo-1(4H)-quinazolinyl]acetyl}({4'-[(trifluoromethyl)oxy]-4-biphenylyl}methyl)amino]-1-piperidinyl}-2-methylpropanoate as a white solid (174 mg).

LCMS Rt=2.77 minutes; m/z [M+H]$^+$=791.3

$^1$H NMR (CDCl$_3$) Characteristic peaks: δ 1.21-1.42 (9H, m), 1.58-2.08 (4H, m), 2.20-2.48 (2H, m), 2.71-5.1 (13H, br m), 6.79-6.87 (1H, d), 6.92-7.11 (3H, m), 7.30-7.46 (5H, m), 7.48-7.63 (5H, m), 8.26-8.40 (1H, m)

This was converted to the bitartrate salt by a method analogous to that described in Example of Synthesis Approach (I).

Example of Synthesis Approach (IV)-5

Methyl 2-[4-({[2-[2-(2,4-difluorophenyl)ethyl]-4-oxo-1(4H)-quinazolinyl]acetyl}{[4'-(trifluoromethyl)-4-biphenylyl]methyl}amino)-1-piperidinyl]-2-methylpropanoate 2,3-dihydroxybutanedioate (salt)

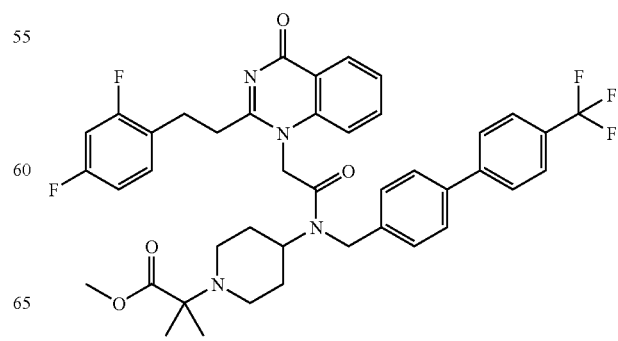

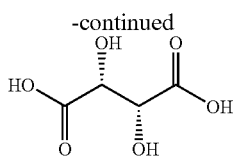

mixture of [2-[2-(2,4-difluorophenyl)ethyl]-4-oxo-1(4H)-quinazolinyl]acetic acid (Int. C3) (100 mg, 1 equiv), methyl 2-methyl-2-[4-({[4'-(trifluoromethyl)-4-biphenylyl]methyl}-amino)-1-piperidinyl]propanoate (Int. B1) (130 mg, 1.03 equiv), DIPEA (0.1 ml, 2 equiv), acetonitrile (2 ml) and HATU (130 mg, 1.4 equiv) was stirred at room temperature for 1 h, then evaporated and redissolved in acetonitrile. Purification by reverse phase HPLC (Preparative Method B) gave methyl 2-[4-({[2-[2-(2,4-difluorophenyl)ethyl]-4-oxo-1(4H)-quinazolinyl]acetyl}{[4'-(trifluoromethyl)-4-biphenylyl]methyl}amino)-1-piperidinyl]-2-methylpropanoate (126 mg).

LCMS Rt=2.698 minutes; m/z [M+H]$^+$=761.3

$^1$H NMR (CDCl$_3$) δ 1.30 (3H, s), 1.34 (3H, s), 1.81-2.03 (4H, m), 2.29-2.35 (1H, m), 2.39-2.45 (1H, m), 2.82-2.87 (1H, m), 3.00-3.14 (4H, m), 3.19-3.24 (1H, m), 3.70-3.73 (3H, m), 4.00/4.51 (1H, 2×br m), 4.74 (1H, s), 4.91 (1H, s), 5.10 (1H, s), 5.54 (1H, s), 6.77-6.84 (1H, m), 6.87-6.98 (1H, m), 7.28-7.43 (2H, m), 7.48-7.61 (5H, m), 7.73-7.81 (5H, m), 8.23-8.29 (1H, m).

This was converted to the bitartrate salt by a method analogous to that described in Example of Synthesis Approach (I).

Example Synthesis Approach (IV)-6

Ethyl 2-[4-({[2-[2-(2,4-difluorophenyl)ethyl]-4-oxo-1(4H)-quinazolinyl]acetyl}{[4'-(trifluoromethyl)-4-biphenylyl]methyl}amino)-1-piperidinyl]-2-methyl-propanoate 2,3-dihydroxybutanedioate (salt)

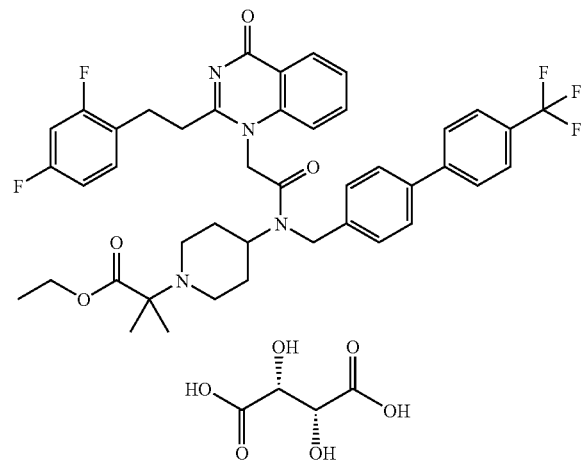

A mixture of [2-[2-(2,4-difluorophenyl)ethyl]-4-oxo-1(4H)-quinazolinyl]acetic acid (Int. C3) (120 mg, 1 equiv), ethyl 2-methyl-2-[4-({[4'-(trifluoromethyl)-4-biphenylyl]methyl}-amino)-1-piperidinyl]propanoate (Int. B2) (204 mg, 1.3 equiv), DMF (1.4 ml) and DIPEA (0.183 ml, 3 equiv) was shaken at room temperature, then HATU (206 mg, 1.5 equiv) was added with vigorous agitation and shaking continued for 1.5 h. A further portion of Intermediate D5 (12 mg, 0.1 equiv) was added then shaking was continued for 2 days. Reverse phase HPLC (Preparative Method B) gave ethyl 2-[4-({[2-[2-(2,4-difluorophenyl)ethyl]-4-oxo-1(4H)-quinazolinyl]acetyl}{[4'-(trifluoromethyl)-4-biphenylyl]-methyl}amino)-1-piperidinyl]-2-methylpropanoate as a white solid (173 mg).

LCMS Rt=2.751 minutes; m/z [M+H]$^+$=775.3

$^1$H NMR (CDCl$_3$) δ (mixture of rotomers) Characteristic peaks: 1.22-1.47 (9H, m), 1.63-2.10 (4H, m), 2.16-5.11 (15H, br m), 6.75-6.88 (2H, m), 7.14-7.80 (12H, m), 8.26-8.40 (1H, m).

This was converted to the bitartrate salt by a method analogous to that described in Example of Synthesis Approach (I).

Example Synthesis Approach (IV)-7

Ethyl 2-{4-[{[2-[2-(2,4-difluorophenyl)ethyl]-4-oxo-1(4H)-quinazolinyl]acetyl}({4'-[(trifluoromethyl)oxy]-4-biphenylyl}methyl)amino]-1-piperidinyl}-2-methylpropanoate 2,3-dihydroxybutanedioate (salt)

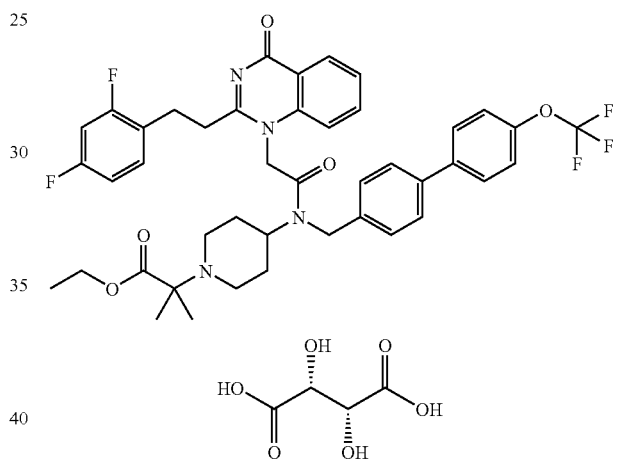

A mixture of [2-[2-(2,4-difluorophenyl)ethyl]-4-oxo-1(4H)-quinazolinyl]acetic acid (Int. C3) (114 mg, 1.1 equiv), ethyl 2-methyl-2-{4-[({4'-[(trifluoromethyl)oxy]-4-biphenylyl}methyl)amino]-1-piperidinyl}propanoate (Int. B3) (139 mg, 1 equiv), DMF (1.2 ml) and DIPEA (0.16 ml, 3 equiv) was shaken at room temperature, then HATU (176 mg, 1.5 equiv) was added with vigorous agitation and shaking continued for 30 min. A further portion of Intermediate D5 (21 mg, 0.2 equiv) was added, followed 1 h later by further HATU (23 mg, 0.2 equiv), then shaking was continued for 18 h. Reverse phase HPLC (Preparative Method B) gave ethyl 2-{4-[{[2-[2-(2,4-difluorophenyl)ethyl]-4-oxo-1(4H)-quinazolinyl]-acetyl}({4'-[(trifluoromethyl)oxy]-4-biphenylyl}methyl)amino]-1-piperidinyl}-2-methylpropanoate as a white solid (149 mg).

LCMS Rt=2.793 minutes; m/z [M+H]$^+$=791.3

$^1$H NMR (CDCl$_3$) Characteristic peaks: δ 1.20-1.45 (9H, m), 1.58-2.12 (4H, m), 2.14-2.48 (2H,m), 2.620-5.11 (11H, m), 6.59-6.72 (1H, m), 6.73-6.90 (2H, m), 7.16-7.64 (11H, m), 8.25-8.40 (1H, m).

This was converted to the bitartrate salt by a method analogous to that described in Example of Synthesis Approach (II).

Example Synthesis Approach (IV)-8

2-[4-({[2-[2-(2,3-Difluorophenyl)ethyl]-4-oxo-1,8-naphthyridin-1(4H)-yl]acetyl}{[4'-(trifluoromethyl)-4-biphenylyl]methyl}amino)-1-piperidinyl]-2-methylpropanoic acid trifluoroacetate

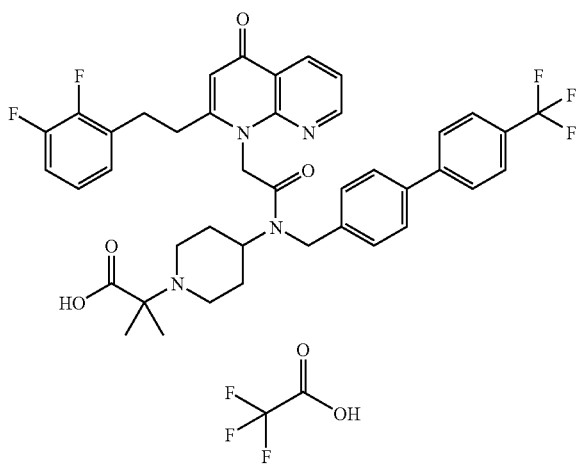

A mixture of 1,1-dimethylethyl 2-methyl-2-[4-({[4'-(trifluoromethyl)-4-biphenylyl]methyl}amino)-1-piperidinyl]propanoate (Int. B4) (1 equiv), [2-[2-(2,3-difluorophenyl)ethyl]-4-oxo-1,8-naphthyridin-1(4H)-yl]acetic acid (Int. C2) (1.2 equiv), DIPEA (3 equiv) and DMF (1.0 ml) is stirred at room temperature for 5 min. HATU (1.5 equiv) is added in 1 portion and stirred an additional 5 min. The crude reaction mixture is concentrated, filtered through a plug of silica eluted with acetone and evaporated to obtain crude 1,1-dimethylethyl 2-[4-({[2-[2-(2,3-difluorophenyl)ethyl]-4-oxo-1,8-naphthyridin-1(4H)-yl]acetyl}{[4'-(trifluoromethyl)-4-biphenylyl]methyl}amino)-1-piperidinyl]-2-methyl propanoate.

The proponate, without isolation, is dissolved in a 1:1 mixture of TFA and DCM and stirred at RT for 4 h. Evaporation and prepative HPLC (Method A) gives the captioned compound.

Other salts can be prepared by conventional means. The free base can also be prepared by conventional means.

Example Synthesis Approach (IV)-9

2-[4-({[2-[2-(2,3-Difluorophenyl)ethyl]-4-oxo-1(4H)-quinazolinyl]acetyl}{[4'-(trifluoromethyl)-4-biphenylyl]methyl}amino)-1-piperidinyl]-2-methyl-propanoic acid trifluoroacetate

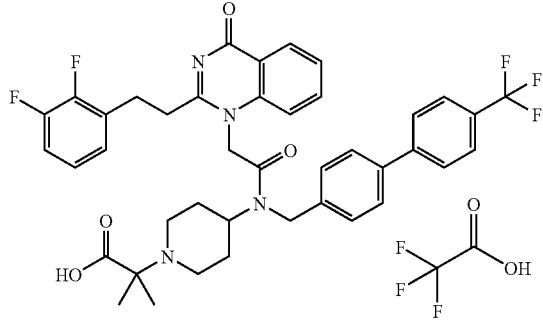

A mixture of 1,1-dimethylethyl 2-methyl-2-[4-({[4'-(trifluoromethyl)-4-biphenylyl]methyl}amino)-1-piperidinyl] propanoate (Int. B4) (1 equiv), [2-[2-(2,3-difluorophenyl)ethyl]-4-oxo-1(4H)-quinazolinyl]acetic acid (Int. C1) (1.2 equiv), DIPEA (3 equiv) and DMF (1.0 ml) is stirred at room temperature for 5 min. HATU (1.5 equiv) is added in 1 portion and stirred an additional 5 min. The crude reaction mixture is concentrated, filtered through a plug of silica eluted with acetone and evaporated to obtain crude 1,1-dimethylethyl 2-[4-({[2-[2-(2,3-difluorophenyl)ethyl]-4-oxo-1(4H)-quinazolinyl]acetyl}{[4'-(trifluoromethyl)-4-biphenylyl]methyl}amino)-1-piperidinyl]-2-methylpropanoate.

The proponate, without isolation, is dissolved in a 1:1 mixture of TFA and DCM and stirred at RT for 4 h. Evaporation and prepative HPLC (Method A) gives the captioned compound.

Example Synthesis Approach (IV)-10

Methyl 2-[4-({[2-[2-(2,3-difluorophenyl)ethyl]-4-oxopyrido[2,3-d]pyrimidin-1(4H)-yl]-acetyl}{[4'-(trifluoromethyl)-4-biphenylyl]methyl}amino)-1-piperidinyl]-2-methyl-propanoate

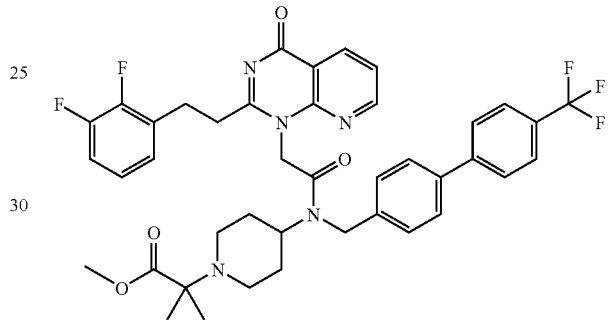

A mixture of [2-[2-(2,3-difluorophenyl)ethyl]-4-oxopyrido[2,3-d]pyrimidin-1(4H)-yl]acetic acid (Int. D1) (20.7 g, 1.3 equiv), methyl 2-methyl-2-[4-({[4'-(trifluoromethyl)-4-biphenylyl]methyl}amino)-1-piperidinyl]propanoate (Int. B1) (20.0 g, 1.3 equiv), DIPEA (24.0 ml, 3 equiv) and DMF (184 ml) was mechanically stirred, then HATU (27.1 g, 1.5 equiv) was added in one portion and stirring continued for 2 h. The reaction mixture was partioned between diethyl ether/THF (1:1) and sodium carbonate (1M, excess). The organic layer was washed with water and brine, dried and evaporated. Chromatography was run sequentially on three silica columns (firstly 3:1 EtOAc/hexanes; secondly 2% MeOH in DCM; thirdly 1:1 EtOAc/hexanes to 100% EtOAc). Product fractions were evaporated to obtain the desired product as an amorphous pink solid (27.5 g).

LCMS Rt=2.702 minutes; m/z [M+H]$^+$=762.3

Crystallisation: A mixture of methyl 2-[4-({[2-[2-(2,3-difluorophenyl)ethyl]-4-oxopyrido[2,3-d]pyrimidin-1(4H)-yl]acetyl}{[4'-(trifluoromethyl)-4-biphenylyl]methyl}-amino)-1-piperidinyl]-2-methylpropanoate (8.0 g) and ethanol (200 ml) was warmed until fully dissolved. The solution was stirred magnetically for 24 h at room temperature, then filtered and 7.5 g of solid collected. These solvated crystals were placed into a 60° C. vacuum oven with a nitrogen bleed to hold the vacuum at approximately 630 Torr for 24 h to provide the unsolvated, crystalline title compound (7.15 g), m.p. 150° C.

$^1$H NMR (CD$_3$OD) δ 1.25 (3H, s), 1.30 (3H, s), 1.63-1.99 (4H, m), 2.16-2.28 (1H, m), 2.3-2.43 (1H, m), 2.89-2.98 (1H, m), 2.98-3.08 (2H, m), 3.16-3.30 (3H, m), 3.66-3.69 (3H, m), 4.02/4.38 (1H, 2×br m), 4.69 (1H, s), 4.87 (1H, s), 5.4/5.73 (2H, 2×s), 6.99-7.19 (3H, m), 7.29-7.35 (1H, m), 7.50-7.61 (3H, m), 7.64-7.82 (5H, m), 8.48-8.57 (1H, m), 8.80-8.89 (1H, m) See FIG. 1 below.

Example Synthesis Approach (IV)-11

Methyl 2-[4-({[2-[2-(2,3-difluorophenyl)ethyl]-4-oxopyrido[2,3-d]pyrimidin-1(4H)-yl]-acetyl}{[4'-(trifluoromethyl)-4-biphenylyl]methyl}amino)-1-piperidinyl]-2-methyl-propanoate 2,3-dihydroxybutanedioate (salt)

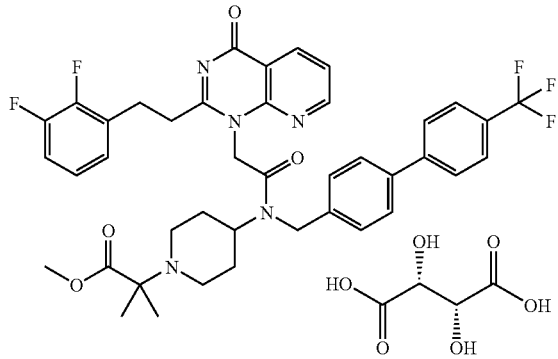

Methyl 2-[4-({[2-[2-(2,3-difluorophenyl)ethyl]-4-oxopyrido[2,3-d]pyrimidin-1(4H)-yl]-acetyl}{[4'-(trifluoromethyl)-4-biphenylyl]methyl}amino)-1-piperidinyl]-2-methylpropanoate (8.5 g, 1 equiv) was suspended in methanol (100 ml) and warmed to 50° C. until the solid dissolved. L-Tartaric acid (1.675 g, 1.0 equiv) was added in one portion and stirred for 30 minutes at room temperature. The solution was concentrated in vacuo to an off-white powder that was dried in a vacuum oven at room temperature.

LCMS Rt=2.697 minutes; m/z [M+H]$^+$=762.3

$^1$H NMR (d$_6$-DMSO) □ 1.17 (3H, s), 1.23 (3H, s), 1.47-1.91 (4H, m), 1.98-2.41 (1H, m), 2.16-2.33 (1H, m), 2.80-3.26 (6H, m), 3.50-3.67 (3H, m), 3.95/4.17 (1H, 2×br m), 4.61 (1H, s), 4.85 (1H, s), 5.39/5.69 (2H, 2×s), 7.08-7.39 (4H, m), 7.53-7.70 (3H, m), 7.72-7.97 (5H, m), 8.42-8.54 (1H, m), 8.85-8.95 (1H, m)

Example Synthesis Approach (IV)-12

Ethyl 2-[4-({[2-[2-(2,3-difluorophenyl)ethyl]-4-oxopyrido[2,3-d]pyrimidin-1(4H)-yl]-acetyl}{[4'-(trifluoromethyl)-4-biphenylyl]methyl}amino)-1-piperidinyl]-2-methylpropanoate 2,3-dihydroxybutanedioate (salt)

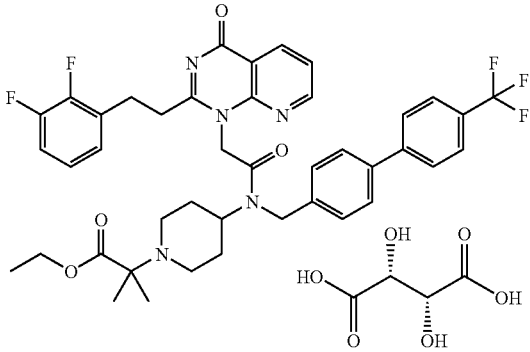

A mixture of [2-[2-(2,3-difluorophenyl)ethyl]-4-oxopyrido[2,3-d]pyrimidin-1(4H)-yl]acetic acid (Int. D1) (116 mg, 1 equiv), ethyl 2-methyl-2-[4-({[4'-(trifluoromethyl)-4-biphenylyl]methyl}amino)-1-piperidinyl]propanoate (Int. B2) (150 mg, 1 equiv), HATU (151 mg, 1.2 equiv), DMF (2.72 ml) and DIPEA (0.17 ml, 3 equiv) was shaken at room temperature for 3.25 h. The reaction mixture was partitioned between ethyl acetate/methanol and aqueous sodium bicarbonate, the organic layer was brine-washed, dried and treated with activated charcoal (250 mg). Flash chromatography (silica, 3-4% methanol in DCM) gave ethyl 2-[4-({[2-[2-(2,3-difluorophenyl)ethyl]-4-oxopyrido[2,3-d]pyrimidin-1(4H)-yl]-acetyl}{[4'-(trifluoromethyl)-4-biphenylyl]methyl}amino)-1-piperidinyl]-2-methylpropanoate as a white solid (178 mg).

LCMS Rt=2.58 minutes; m/z [M+H]$^+$=776.3

$^1$H NMR (CDCl$_3$) δ 1.20-1.40 (9H, m), 1.56-2.02 (4H, m), 2.19-2.44 (2H, m), 2.88-3.20, (4H, m), 3.22-3.40 (2H, m), 3.81/4.58 (1H, 2×m), 4.11-4.27 (2H, m), 4.69/4.84 (2H, 2×s), 5.17/5.49 (2H, 2×s), 6.95-7.14 (3H, m), 7.25-7.31 (1H, m), 7.38-7.54 (3H, m), 7.54, 7.61 (1H, m), 7.62-7.79 (4H, m), 8.57-8.75 (2H, m)

This was converted to the bitartrate salt by a method analogous to that described for Example of Synthesis Approach (II).

Example Synthesis Approach (IV)-13

Ethyl 2-{4-[{[2-[2-(2,3-difluorophenyl)ethyl]-4-oxopyrido[2,3-d]pyrimidin-1(4H)-yl]acetyl}({4'-[(trifluoromethyl)oxy]-4-biphenylyl}methyl)amino]-1-piperidinyl}-2-methylpropanoate 2,3-dihydroxybutanedioate (salt)

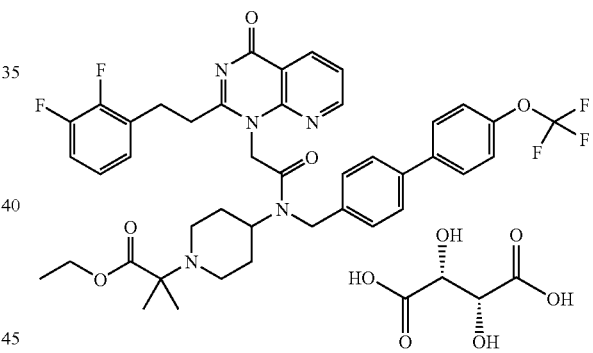

A mixture of [2-[2-(2,3-difluorophenyl)ethyl]-4-oxopyrido[2,3-d]pyrimidin-1(4H)-yl]acetic acid (Int. D1) (114 mg, 1.1 equiv), ethyl 2-methyl-2-{4-[({4'-[(trifluoromethyl)oxy]-4-biphenylyl}methyl)amino]-1-piperidinyl}propanoate (Int. B4) (139 mg, 1 equiv), DMF (1.2 ml) and DIPEA (0.16 ml, 3 equiv) was shaken at room temperature for 30 min, then HATU (176 mg, 1.5 equiv) was added and shaking continued for 3 h. Reverse phase HPLC (Preparative Method B) gave ethyl 2-{4-[{[2-[2-(2,3-difluorophenyl)ethyl]-4-oxo-1(4H)-quinazolinyl]acetyl}({4'-[(trifluoromethyl)oxy]-4-biphenylyl}methyl)amino]-1-piperidinyl}-2-methylpropanoate as a white solid (166 mg).

LCMS Rt=2.87 minutes; m/z [M+H]$^+$=792.3

$^1$H NMR (CDCl$_3$) δ 1.18-1.42 (9H, m), 1.54-2.04 (4H, m), 2.12-2.46 (2H, m), 2.86-3.21 (4H, m), 3.21-3.41 (2H, m), 3.79/4.57 (1H, 2×m), 4.10-4.27 (2H, m), 4.68 (1H, s), 4.82 (1H, s), 5.17 (1H, s), 5.47 (1H, s), 6.94-7.16 (3H, m), 7.20-7.36 (3H, m), 7.37-7.48 (3H, m), 7.48-7.61 (3H, m), 8.56-8.76 (2H, m).

This was converted to the bitartrate salt by a method analogous to that described for Example of Synthesis Approach (II).

Example Synthesis Approach (IV)-14

1-Methylethyl 2-[4-({[2-[2-(2,3-difluorophenyl)ethyl]-4-oxopyrido[2,3-d]pyrimidin-1(4H)-yl]acetyl}{[4'-(trifluoromethyl)-4-biphenylyl]methyl}amino)-1-piperidinyl]-2-methylpropanoate 2,3-dihydroxybutanedioate (salt)

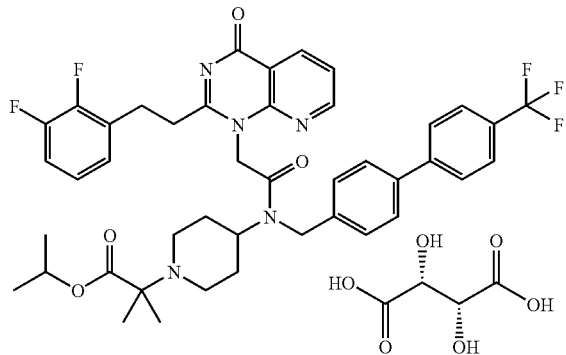

A mixture of 1-methylethyl 2-methyl-2-[4-({[4'-(trifluoromethyl)-4-biphenylyl]methyl}-amino)-1-piperidinyl]propanoate (Int. B3) (420 mg, 1 equiv), [2-[2-(2,3-difluorophenyl)-ethyl]-4-oxopyrido[2,3-d]pyrimidin-1(4H)-yl]acetic acid (Int. D1) (300 mg, 1 equiv), HATU (396 mg, 1.2 equiv), DIPEA (0.22 ml, 1.5 equiv) and DMF (3.0 ml) was stirred at room temperature for 30 min. The crude reaction mixture was applied directly to reverse-phase HPLC (Preparative Method A) to obtain 1-methylethyl 2-[4-({[2-[2-(2,3-difluorophenyl)ethyl]-4-oxopyrido[2,3-d]pyrimidin-1(4H)-yl]acetyl}{[4'-(trifluoromethyl)-4-biphenylyl]methyl}amino)-1-piperidinyl]-2-methylpropanoate (171 mg).

LCMS Rt=2.837 minutes; m/z [M+H]$^+$=790.3

$^1$H NMR (CD$_3$OD) δ 1.16-1.37 (12H, m), 1.62-2.01 (4H, m), 2.27-2.55 (2H, m), 2.95-3.12 (3H, m), 3.12-3.29 (3H, m), 4.06/4.40 (1H, 2×br m), 4.71 (1H, s), 4.89 (1H, s), 4.92-5.07 (1H, m), 5.43/5.76 (2H, 2×s), 7.00-7.21 (3H, m), 7.29-7.38 (1H, m), 7.49-7.65 (3H, m), 7.65-7.87 (5H, m), 8.48-8.58 (1H, m), 8.81-8.90 (1H, m).

This was converted to the bitartrate salt by a method analogous to that described for Example of Synthesis Approach (II).

Example Synthesis Approach (IV)-15

1-Methylethyl 2-{4-[{[2-[2-(2,3-difluorophenyl)ethyl]-4-oxopyrido[2,3-d]pyrimidin-1(4H)-yl]acetyl}({4'-[(trifluoromethyl)oxy]-4-biphenylyl}methyl)amino]-1-piperidinyl}-2-methylpropanoate 2,3-dihydroxybutanedioate (salt)

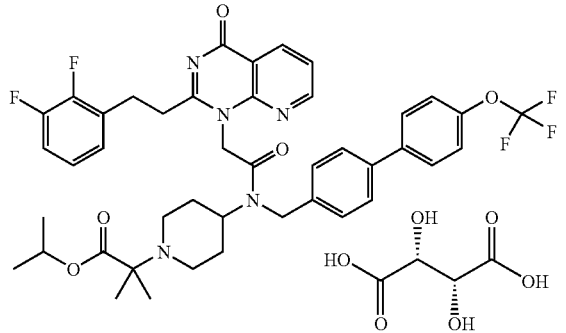

A mixture of 1-methylethyl 2-methyl-2-{4-[({4'-[(trifluoromethyl)oxy]-4-biphenylyl}methyl)amino]-1-piperidinyl}propanoate (Int. B5) (80 mg, 1 equiv), [2-[2-(2,3-difluorophenyl)ethyl]-4-oxopyrido[2,3-d]pyrimidin-1(4H)-yl]acetic acid (Int. D1) (67 mg, 1 equiv), HATU (400 mg, 5 equiv), DIPEA (0.22 ml, 1.5 equiv) and DMF (2.0 ml) was stirred at room temperature for 30 min. The crude reaction mixture was applied directly to reverse-phase HPLC (Preparative Method A) to obtain 1-methylethyl 2-{4-[{[2-[2-(2,3-difluorophenyl)ethyl]-4-oxopyrido[2,3-d]pyrimidin-1(4H)-yl]acetyl}({4'-[(trifluoromethyl)oxy]-4-biphenylyl}methyl)amino]-1-piperidinyl}-2-methylpropanoate (25 mg).

LCMS Rt=2.952 minutes; m/z [M+H]$^+$=806.4

$^1$H NMR (DMSO-d$_6$) δ 1.09-1.25 (12H, m), 1.47-1.91 (4H, m), 2.05-2.20 (1H, m), 2.21-2.38 (1H, m), 2.87-3.07 (3H, m), 3.08-3.22 (3H, m), 3.95/4.17 (1H, 2×br m), 4.59 (1H, s), 4.75-4.97 (2H, m), 5.38/5.68 (2H, 2×s), 7.90-7.21 (1H, m), 7.21-7.36 (3H, m), 7.42-7.55 (3H, m), 7.55-7.64 (2H, m), 7.66-7.77 (2H, m), 7.77-7.85 (1H, m), 8.43-8.52 (1H, m), 8.86-8.95 (1H, m)

This was converted to the bitartrate salt by a method analogous to that described for Example of Synthesis Approach (II).

Example Synthesis Approach (IV)-16

Methyl 2-[4-({[2-[2-(2,4-difluorophenyl)ethyl]-4-oxopyrido[2,3-d]pyrimidin-1(4H)-yl]acetyl}{[4'-(trifluoromethyl)-4-biphenylyl]methyl}amino)-1-piperidinyl]-2-methylpropanoate 2,3-dihydroxybutanedioate (salt)

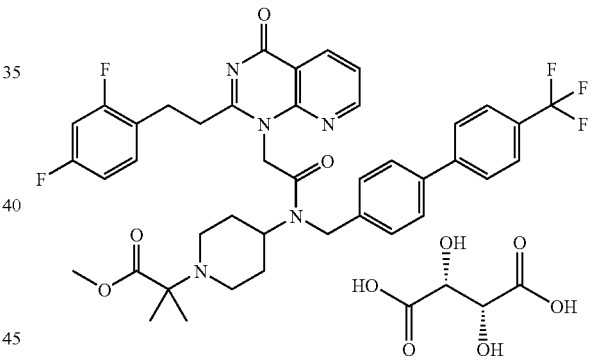

A mixture of [2-[2-(2,4-difluorophenyl)ethyl]-4-oxopyrido[2,4-d]pyrimidin-1(4H)-yl]acetic acid (Int. D2) (100 mg, 1 equiv), methyl 2-methyl-2-[4-({[4'-(trifluoromethyl)-4-biphenylyl]methyl}amino)-1-piperidinyl]propanoate (Int. B1) (130 mg, 1.03 equiv), DIPEA (0.16 ml, 3 equiv), acetonitrile (2 ml) and HATU (130 mg, 1.2 equiv) was stirred at room temperature for 1 h, then evaporated and redissolved in acetonitrile. Purification by reverse phase HPLC (Preparative Method B) gave methyl 2-[4-({[2-[2-(2,4-difluorophenyl)ethyl]-4-oxopyrido[2,3-d]pyrimidin-1(4H)-yl]acetyl}{[4'-(trifluoromethyl)-4-biphenylyl]methyl}amino)-1-piperidinyl]-2-methylpropanoate (145 mg).

LCMS Rt=2.716 minutes; m/z [M+H]$^+$=762.3

$^1$H NMR (CDCl$_3$) δ 1.27 (3H, s), 1.33 (3H, s), 1.69-1.98 (4H, m), 2.22-2.29 (1H, m), 2.36-2.43 (1H, m), 2.96-3.08 (3H, m), 3.13-3.24 (3H, m), 3.69-3.72 (3H, m), 4.04/4.41 (1H, 2×br m), 4.72 (1H, s), 4.91 (1H, s), 5.41/5.73 (2H, 2×s), 6.84-6.97 (2H, m), 7.34-7.44 (2H, m), 7.54-7.63 (3H, m), 7.69-7.83 (5H, m), 8.55-8.60 (1H, m), 8.86-8.91 (1H, m).

This was converted to the bitartrate salt by a method analogous to that described for Example of Synthesis Approach (II).

Example Synthesis Approach (IV)-17

Ethyl 2-[4-({[2-[2-(2,4-difluorophenyl)ethyl]-4-oxopyrido[2,3-d]pyrimidin-1(4H)-yl]acetyl}{[4'-(trifluoromethyl)-4-biphenylyl]methyl}amino)-1-piperidinyl]-2-methylpropanoate 2,3-dihydroxybutanedioate (salt)

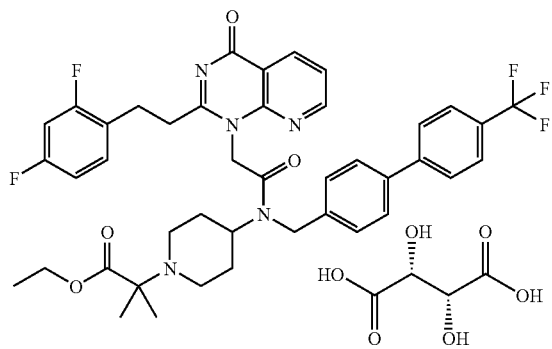

A mixture of [2-[2-(2,4-difluorophenyl)ethyl]-4-oxopyrido[2,3-d]pyrimidin-1(4H)-yl]acetic acid (Int. D2) (120 mg, 1 equiv), ethyl 2-methyl-2-[4-({[4'-(trifluoromethyl)-4-biphenylyl]methyl}amino)-1-piperidinyl]propanoate (Int. B2) (198 mg, 1.3 equiv), DMF (1.4 ml) and DIPEA (0.178 ml, 3 equiv) was shaken at room temperature for 1.5 h, then HATU (200 mg, 1.5 equiv) was added with vigorous agitation and shaking continued for 1.5 h. A further portion of Intermediate D2 (12 mg, 0.1 equiv) was added then shaking was continued for 2 days. Reverse phase HPLC (Preparative Method B) gave ethyl 2-[4-({[2-[2-(2,4-difluorophenyl)ethyl]-4-oxopyrido[2,3-d]pyrimidin-1(4H)-yl]acetyl}{[4'-(trifluoromethyl)-4-biphenylyl]methyl}amino)-1-piperidinyl]-2-methylpropanoate as a white solid (170 mg).

LCMS Rt=2.827 minutes; m/z [M+H]$^+$=776.3

$^1$H NMR (CDCl$_3$) Characteristic peaks: δ 1.14-1.43 (9H, m), 1.57-2.05 (4H, m), 2.10-2.46 (2H, m), 2.84-3.11 (3H, m), 3.12-3.34 (3H, m), 3.65/3.85 (1H, m), 4.06-4.27 (2H, m), 4.65/4.85 (2H, s), 5.15/5.45 (2H, s), 6.62-6.89 (2H, m), 7.18-7.34 (1H, m), 7.37-7.82 (9H, m), 8.59-8.77 (2H, m).

This was converted to the bitartrate salt by a method analogous to that described for Example of Synthesis Approach (II).

Example Synthesis Approach (IV)-18

Ethyl 2-{4-[{[2-[2-(2,4-difluorophenyl)ethyl]-4-oxopyrido[2,3-d]pyrimidin-1(4H)-yl]acetyl}({4'-[(trifluoromethyl)oxy]-4-biphenylyl}methyl)amino]-1-piperidinyl}-2-methylpropanoate 2,3-dihydroxybutanedioate (salt)

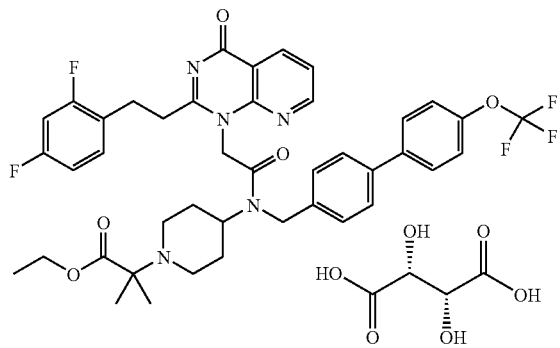

A mixture of [2-[2-(2,4-difluorophenyl)ethyl]-4-oxopyrido[2,4-d]pyrimidin-1(4H)-yl]acetic acid (Int. D2) (114 mg, 1.1 equiv), ethyl 2-methyl-2-{4-[({4'-[(trifluoromethyl)oxy]-4-biphenylyl}methyl)amino]-1-piperidinyl}propanoate (Int. B4) (139 mg, 1 equiv), DMF (1.2 ml) and DIPEA (0.16 ml, 3 equiv) was shaken at room temperature, then HATU (176 mg, 1.5 equiv) was added with vigorous agitation and shaking continued for 2 h. Reverse phase HPLC (Preparative Method B) gave ethyl 2-{4-[{[2-[2-(2,4-difluorophenyl)ethyl]-4-oxopyrido[2,3-d]pyrimidin-1(4H)-yl]acetyl}({4'-[(trifluoromethyl)oxy]-4-biphenylyl}-methyl)amino]-1-piperidinyl}-2-methylpropanoate as a white solid (149 mg).

LCMS Rt=2.801 minutes; m/z [M+H]$^+$=792.3

$^1$H NMR (CDCl$_3$) δ 1.18-1.40 (9H, m), 1.61-2.02 (4H, m), 2.20-2.44 (2H, m), 2.83-3.35 (6H, br m), 3.79/4.57 (1H, 2×br m), 4.07-4.27 (2H, m), 4.68/4.81 (2H, 2×s), 5.14/5.46 (2H, 2×br m), 6.62-6.90 (2H, 2×m), 7.18-7.63 (10H, m), 8.59-8.75 (2H, m).

This was converted to the bitartrate salt by a method analogous to that described for Example of Synthesis Approach (II).

Example Synthesis Approach (IV)-19

1-Methylethyl 2-[4-({[2-[2-(2,4-difluorophenyl)ethyl]-4-oxopyrido[2,3-d]pyrimidin-1(4H)-yl]acetyl}{[4'-(trifluoromethyl)-4-biphenylyl]methyl}amino)-1-piperidinyl]-2-methylpropanoate 2,3-dihydroxybutanedioate (salt)

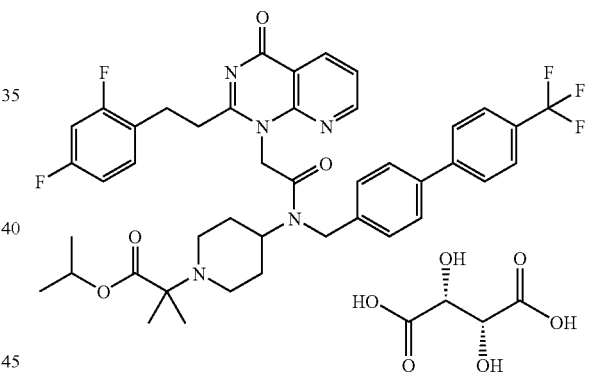

A mixture of 1-methylethyl 2-methyl-2-[4-({[4'-(trifluoromethyl)-4-biphenylyl]methyl}-amino)-1-piperidinyl]propanoate (Int. B3) (70 mg, 1 equiv), [2-[2-(2,4-difluorophenyl)ethyl]-4-oxopyrido[2,4-d]pyrimidin-1(4H)-yl]acetic acid (Int. D2) (52.2 mg, 1 equiv), HATU (69 mg, 1.2 equiv), DIPEA (0.04 ml, 1.5 equiv) and DMF (1.0 ml) was stirred at room temperature for 10 min. The crude reaction mixture was applied directly to reverse-phase HPLC (Preparative Method A) to obtain 1-methylethyl 2-[4-({[2-[2-(2,4-difluorophenyl)ethyl]-4-oxopyrido[2,3-d]pyrimidin-1(4H)-yl]acetyl}{[4'-(trifluoromethyl)-4-biphenylyl]methyl}amino)-1-piperidinyl]-2-methylpropanoate (20 mg).

LCMS Rt=2.910 minutes; m/z [M+H]$^+$=790.4

$^1$H NMR (d$_6$-DMSO) δ 1.08-1.27 (12H, m), 1.40-1.90 (4H, m), 2.03-2.35 (2H, m), 2.85-3.24 (6H, m), 3.95/4.17 (1H, 2×br m), 4.61 (1H, s), 4.80-4.97 (2H, m), 5.36/5.67 (2H, 2×s), 6.96-7.10 (1H, m), 7.13-7.28 (1H, m), 7.28-7.38 (1H, m), 7.39-7.54 (1H, m), 7.54-7.68 (3H, m), 7.72-7.98 (5H, m), 8.43-8.52 (1H, m), 8.86-8.95 (1H, m)

This was converted to the bitartrate salt by a method analogous to that described for Example of Synthesis Approach (II).

Example Synthesis Approach (IV)-20

1-Methylethyl 2-{4-[{[2-[2-(2,4-difluorophenyl)ethyl]-4-oxopyrido[2,3-d]pyrimidin-1(4H)-yl]acetyl}({4'-[(trifluoromethyl)oxy]-4-biphenylyl}methyl)amino]-1-piperidinyl}-2-methylpropanoate 2,3-dihydroxybutanedioate (salt)

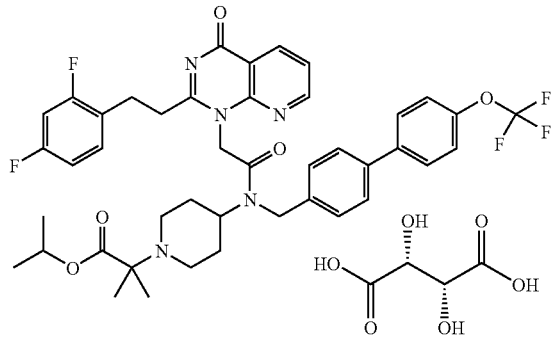

A mixture of 1-methylethyl 2-methyl-2-{4-[({4'-[(trifluoromethyl)oxy]-4-biphenylyl}methyl)amino]-1-piperidinyl}propanoate (Int. B5) (80 mg, 1 equiv), [2-[2-(2,3-difluorophenyl)ethyl]-4-oxopyrido[2,4-d]pyrimidin-1(4H)-yl]acetic acid (Int. D2) (57 mg, 1 equiv), HATU (76 mg, 1.2 equiv), DIPEA (0.04 ml, 1.5 equiv) and DMF (1.0 ml) was stirred at room temperature for 10 min. The crude reaction mixture was applied directly to reverse-phase HPLC (Preparative Method A) to obtain 1-methylethyl 2-{4-[{[2-[2-(2,4-difluorophenyl)ethyl]-4-oxopyrido[2,3-d]pyrimidin-1(4H)-yl]acetyl}({4'-[(trifluoromethyl)-oxy]-4-biphenylyl}methyl)amino]-1-piperidinyl}-2-methylpropanoate (47 mg).

LCMS Rt=2.909 minutes; m/z [M+H]$^+$=806.4

$^1$H NMR (d$_6$-DMSO) δ 1.09-1.27 (12H, m), 1.50-1.90 (4H, m), 2.03-2.17 (1H, m), 2.20-2.37 (1H, m), 2.88-3.18 (6H, m), 3.94/4.17 (1H, 2×m), 4.60 (1H, s), 4.74-4.96 (2H, m), 5.36/5.66 (2H, 2×br s), 6.96-7.09 (1H, m), 7.14-7.32 (2H, m), 7.39-7.55 (4H, m), 7.55-7.66 (2H, m), 7.66-7.87 (3H, m), 8.43-8.54 (1H, m), 8.85-8.96 (1H, m).

This was converted to the bitartrate salt by a method analogous to that described for Example of Synthesis Approach (II).

Example Synthesis Approach (IV)-21

Methyl 2-{4-[{[2-[2-(2,3-difluorophenyl)ethyl]-4-oxopyrido[2,3-d]pyrimidin-1(4H)-yl]acetyl}({4'-[(trifluoromethyl)oxy]-4-biphenylyl}methyl)amino]-1-piperidinyl}-2-methylpropanoate dihydroxybutanedioate (salt)

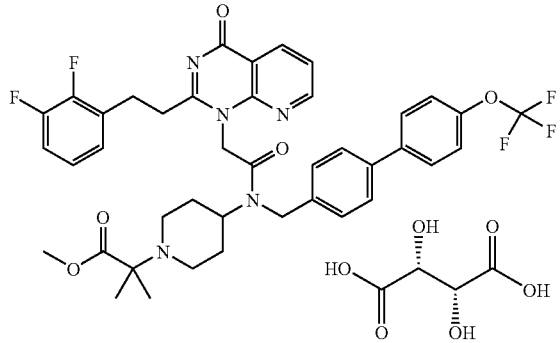 [SMILES: COC(=O)C(C)(C)N1CCC(N(Cc2ccc(-c3ccc(OC(F)(F)F)cc3)cc2)C(=O)Cn2c(CCc3cccc(F)c3F)nc(=O)c3cccnc32)CC1 ; O=C(O)[C@H](O)[C@@H](O)C(=O)O]

A mixture of methyl 2-methyl-2-{4-[({4'-[(trifluoromethyl)oxy]-4-biphenylyl}methyl)amino]-1-piperidinyl}propanoate (Int. B6) (145 mg, 1 equiv), [2-[2-(2,3-difluorophenyl)ethyl]-4-oxopyrido[2,3-d]pyrimidin-1(4H)-yl]acetic acid (Int. D1) (122 mg, 1 equiv), DIPEA (0.084 ml, 1.5 equiv) and DMF (2.0 ml) was stirred at room temperature for 5 min. The HATU (160 mg, 1.3 equiv) was added in 1 portion and stirred an additional 1 hour under nitrogen. The crude reaction mixture was applied directly to reverse-phase HPLC (Preparative Method A) to obtain methyl 2-{4-[{[2-[2-(2,3-difluorophenyl)ethyl]-4-oxopyrido[2,3-d]pyrimidin-1(4H)-yl]acetyl}({4'-[(trifluoromethyl)oxy]-4-biphenylyl} methyl)amino]-1-piperidinyl}-2-methylpropanoate (116 mg).

LCMS Rt=2.721 minutes; m/z [M+H]$^+$=778.3

$^1$H NMR (CDCl$_3$) Characteristic peaks: δ 1.53-1.62 (6H, m), 3.46-5.99 (22H, m), 7.01-7.21 (3H, m), 7.30-7.43 (3H, m), 7.50-7.78 (6H, m), 8.54-8.60 (1H, m), 8.86-8.94 (1H, m).

This was converted to the bitartrate salt by a method analogous to that described for Example of Synthesis Approach (II).

Example Synthesis Approach (IV)-22

2-[4-({[2-[2-(2,3-Difluorophenyl)ethyl]-4-oxopyrido[2,3-d]pyrimidin-1(4H)-yl]acetyl}-{[4'-(trifluoromethyl)-4-biphenylyl]methyl}amino)-1-piperidinyl]-2-methylpropanoic acid trifluoroacetate

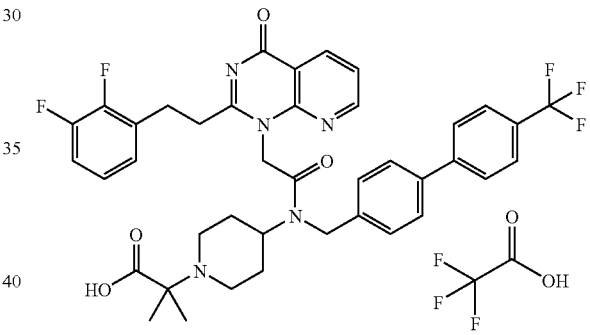

A mixture of 1,1-dimethylethyl 2-methyl-2-[4-({[4'-(trifluoromethyl)-4-biphenylyl]methyl}amino)-1-piperidinyl]propanoate (Int. B7) (150 mg, 1 equiv), [2-[2-(2,3-difluorophenyl)ethyl]-4-oxopyrido[2,3-d]pyrimidin-1(4H)-yl]acetic acid (Int. D1) (130 mg, 1.2 equiv), DIPEA (0.164 ml, 3 equiv) and DMF (1.0 ml) was stirred at room temperature for 5 min. HATU (180 mg, 1.5 equiv) was added in 1 portion and stirred an additional 5 min. The crude reaction mixture was concentrated, filtered through a plug of silica eluted with acetone and evaporated to obtain crude 1,1-dimethylethyl 2-[4-({[2-[2-(2,3-difluorophenyl)ethyl]-4-oxopyrido[2,3-d]pyrimidin-1(4H)-yl]acetyl}{[4'-(trifluoromethyl)-4-biphenylyl]methyl}amino)-1-piperidinyl]-2-methylpropanoate.

LCMS Rt=2.823 minutes; m/z [M+H]$^+$=804.4

This intermediate, without isolation, was dissolved in a 1:1 mixture of TFA and DCM and stirred at RT for 4 h. Evaporation and prepative HPLC (Method A) gave the desired 2-[4-({[2-[2-(2,3-difluorophenyl)ethyl]-4-oxopyrido[2,3-d]pyrimidin-1(4H)-yl]acetyl}{[4'-(trifluoromethyl)-4-biphenylyl]methyl}amino)-1-piperidinyl]-2-methylpropanoic acid trifluoroacetate (70 mg).

LCMS Rt=2.554 minutes; m/z [M+H]$^+$=748.2

$^1$H NMR (d$_6$-DMSO) d 1.44 (3H, s), 1.51 (3H, s), 1.70-2.30 (4H, m), 2.41-2.56 (2H, m), 2.94-3.54 (6H, m), 4.44-

4.95 (3H, m), 5.42/5.76 (2H, 2×br s), 7.07-7.38 (4H, m), 7.54-7.75 (3H, m), 7.76-7.99 (5H, m), 8.42-8.54 (1H, m), 8.85-8.98 (1H, m).

Other salts can be prepared by conventional means. The free base can also be prepared by conventional means.

In some embodiments, compounds useful as inhibitors of Lp-PLA2 useful in the methods as disclosed herein are:
1-(N-(2-(diethylamino)ethyl)-N-(4-(4-trifluoromethylphenyl)benzyl)-aminocarbonylmethyl)-2-(4-fluorobenzyl) thio-5,6-trimethylenepyrimidin-4-one, also referred to as "SB480848" or the USAN name "darapladib" which is a pyrimidinone-based compound and a reversible inhibitor of Lp-PLA$_2$ and is used in the Examples herein,
N-(2-diethylaminoethyl)-2-[2-(2-(2,3-difluorophenyl)ethyl)-4-oxo-4,5,6,7-tetrahydro-cyclopentapyrimidin-1-yl]-N-(4'-trifluoromethyl-biphenyl-4-ylmethyl)acetamide;
N-(1-(2-Methoxyethyl)piperidin-4-yl)-2-[2-(2,3-difluorobenzylthio)-4-oxo-4H-quinolin-1-yl]-N-(4'-trifluoromethylbiphenyl-4-ylmethyl)acetamide; and
methyl 2-[4-({[2-[2-(2,3-difluorophenyl)ethyl]-4-oxopyrido[2,3-d]pyrimidin-1(4H)-yl]-acetyl}{[4'-(trifluoromethyl)-4-biphenylyl]methyl}amino)-1-piperidinyl]-2-methylpropanoate.

Pharmaceutically acceptable salts of 1-(N-(2-(diethylamino)ethyl)-N-(4-(4-trifluoromethylphenyl)benzyl)-aminocarbonylmethyl)-2-(4-fluorobenzyl)thio-5,6-trimethylenepyrimidin-4-one, AKA SB480848, and used in the Examples herein; N-(2-diethylaminoethyl)-2-[2-(2-(2,3-difluorophenyl)ethyl)-4-oxo-4,5,6,7-tetrahydro-cyclopentapyrimidin-1-yl]-N-(4'-trifluoromethyl-biphenyl-4-ylmethyl)acetamide; N-(1-(2-Methoxyethyl)piperidin-4-yl)-2-[2-(2,3-difluorobenzylthio)-4-oxo-4H-quinolin-1-yl]-N-(4'-trifluoromethylbiphenyl-4-ylmethyl)acetamide; and methyl 2-[4-({[2-[2-(2,3-difluorophenyl)ethyl]-4-oxopyrido[2,3-d]pyrimidin-1(4H)-yl]acetyl}{[4'-(trifluoromethyl)-4-biphenylyl]methyl}amino)-1-piperidinyl]-2-methylpropanoate are also useful as inhibitors of Lp-PLA2 for use in the methods as disclosed herein.

Nucleic Acid Inhibitors of Lp-PLA2

In some embodiments, agents that inhibit Lp-PLA$_2$ are nucleic acids. Nucleic acid inhibitors of Lp-PLA$_2$ are, for example, but are not limited to, RNA interference-inducing molecules, for example but are not limited to siRNA, dsRNA, stRNA, shRNA and modified versions thereof, where the RNA interference molecule silences the gene expression of Lp-PLA$_2$. In some embodiments, the nucleic acid inhibitor of Lp-PLA$_2$ is an anti-sense oligonucleic acid, or a nucleic acid analogue, for example but are not limited to DNA, RNA, peptide-nucleic acid (PNA), pseudo-complementary PNA (pc-PNA), or locked nucleic acid (LNA) and the like. In alternative embodiments, the nucleic acid is DNA or RNA, and nucleic acid analogues, for example PNA, pcPNA and LNA. A nucleic acid can be single or double stranded, and can be selected from a group comprising nucleic acid encoding a protein of interest, oligonucleotides, PNA, etc. Such nucleic acid sequences include, for example, but are not limited to, nucleic acid sequence encoding proteins that act as transcriptional repressors, antisense molecules, ribozymes, small inhibitory nucleic acid sequences, for example but are not limited to RNAi, shRNAi, siRNA, micro RNAi (mRNAi), antisense oligonucleotides etc.

In some embodiments single-stranded RNA (ssRNA), a form of RNA endogenously found in eukaryotic cells can be used to form an RNAi molecule. Cellular ssRNA molecules include messenger RNAs (and the progenitor pre-messenger RNAs), small nuclear RNAs, small nucleolar RNAs, transfer RNAs and ribosomal RNAs. Double-stranded RNA (dsRNA) induces a size-dependent immune response such that dsRNA larger than 30 bp activates the interferon response, while shorter dsRNAs feed into the cell's endogenous RNA interference machinery downstream of the Dicer enzyme.

Lp-PLA$_2$ can be reduced by inhibition of the expression of Lp-PLA$_2$ polypeptide or by "gene silencing" methods commonly known by persons of ordinary skill in the art.

RNA interference (RNAi) provides a powerful approach for inhibiting the expression of selected target polypeptides. RNAi uses small interfering RNA (siRNA) duplexes that target the messenger RNA encoding the target polypeptide for selective degradation. siRNA-dependent post-transcriptional silencing of gene expression involves cutting the target messenger RNA molecule at a site guided by the siRNA.

RNA interference (RNAi) is an evolutionarily conserved process whereby the expression or introduction of RNA of a sequence that is identical or highly similar to a target gene results in the sequence specific degradation or specific post-transcriptional gene silencing (PTGS) of messenger RNA (mRNA) transcribed from that targeted gene (see Coburn, G. and Cullen, B. (2002) J. of Virology 76(18):9225), thereby inhibiting expression of the target gene. In one embodiment, the RNA is double stranded RNA (dsRNA). This process has been described in plants, invertebrates, and mammalian cells. In nature, RNAi is initiated by the dsRNA-specific endonuclease Dicer, which promotes processive cleavage of long dsRNA into double-stranded fragments termed siRNAs. siRNAs are incorporated into a protein complex (termed "RNA induced silencing complex," or "RISC") that recognizes and cleaves target mRNAs. RNAi can also be initiated by introducing nucleic acid molecules, e.g., synthetic siRNAs or RNA interfering agents, to inhibit or silence the expression of target genes. As used herein, "inhibition of target gene expression" includes any decrease in expression or protein activity or level of the target gene or protein encoded by the target gene as compared to a situation wherein no RNA interference has been induced. The decrease can be of at least 30%, 40%, 50%, 60%, 70%, 80%, 90%, 95% or 99% or more as compared to the expression of a target gene or the activity or level of the protein encoded by a target gene which has not been targeted by an RNA interfering agent.

"Short interfering RNA" (siRNA), also referred to herein as "small interfering RNA" is defined as an agent which functions to inhibit expression of a target gene, e.g., by RNAi. An siRNA can be chemically synthesized, can be produced by in vitro transcription, or can be produced within a host cell. In one embodiment, siRNA is a double stranded RNA (dsRNA) molecule of about 15 to about 40 nucleotides in length, preferably about 15 to about 28 nucleotides, more preferably about 19 to about 25 nucleotides in length, and more preferably about 19, 20, 21, 22, or 23 nucleotides in length, and can contain a 3' and/or 5' overhang on each strand having a length of about 0, 1, 2, 3, 4, or 5 nucleotides. The length of the overhang is independent between the two strands, i.e., the length of the overhang on one strand is not dependent on the length of the overhang on the second strand. Preferably the siRNA is capable of promoting RNA interference through degradation or specific post-transcriptional gene silencing (PTGS) of the target messenger RNA (mRNA).

siRNAs also include small hairpin (also called stem loop) RNAs (shRNAs). In one embodiment, these shRNAs are composed of a short (e.g., about 19 to about 25 nucleotide) antisense strand, followed by a nucleotide loop of about 5 to about 9 nucleotides, and the analogous sense strand. Alternatively, the sense strand can precede the nucleotide loop structure and the antisense strand can follow. These shRNAs can be contained in plasmids, retroviruses, and lentiviruses and expressed from, for example, the pol III U6 promoter, or another promoter (see, e.g., Stewart, et al. (2003) RNA April; 9(4):493-501, incorporated by reference herein in its entirety).

The target gene or sequence of the RNA interfering agent can be a cellular gene or genomic sequence, e.g. the Lp-PLA$_2$ sequence. An siRNA can be substantially homologous to the target gene or genomic sequence, or a fragment thereof. As used in this context, the term "homologous" is defined as being substantially identical, sufficiently complementary, or similar to the target mRNA, or a fragment thereof, to effect RNA interference of the target. In addition to native RNA molecules, RNA suitable for inhibiting or interfering with the expression of a target sequence include RNA derivatives and analogs. Preferably, the siRNA is identical to its target.

The siRNA preferably targets only one sequence. Each of the RNA interfering agents, such as siRNAs, can be screened for potential off-target effects by, for example, expression profiling. Such methods are known to one skilled in the art and are described, for example, in Jackson et al, Nature Biotechnology 6:635-637, 2003. In addition to expression profiling, one can also screen the potential target sequences for similar sequences in the sequence databases to identify potential sequences which can have off-target effects. For example, according to Jackson et al. (Id.) 15, or perhaps as few as 11 contiguous nucleotides of sequence identity are sufficient to direct silencing of non-targeted transcripts. Therefore, one can initially screen the proposed siRNAs to avoid potential off-target silencing using the sequence identity analysis by any known sequence comparison methods, such as BLAST.

siRNA molecules need not be limited to those molecules containing only RNA, but, for example, further encompasses chemically modified nucleotides and non-nucleotides, and also include molecules wherein a ribose sugar molecule is substituted for another sugar molecule or a molecule which performs a similar function. Moreover, a non-natural linkage between nucleotide residues can be used, such as a phosphorothioate linkage. For example, siRNA containing D-arabinofuranosyl structures in place of the naturally-occurring D-ribonucleosides found in RNA can be used in RNAi molecules according to the present invention (U.S. Pat. No. 5,177,196). Other examples include RNA molecules containing the o-linkage between the sugar and the heterocyclic base of the nucleoside, which confers nuclease resistance and tight complementary strand binding to the oligonucleotidesmolecules similar to the oligonucleotides containing 2'-O-methyl ribose, arabinose and particularly D-arabinose (U.S. Pat. No. 5,177,196).

The RNA strand can be derivatized with a reactive functional group of a reporter group, such as a fluorophore. Particularly useful derivatives are modified at a terminus or termini of an RNA strand, typically the 3' terminus of the sense strand. For example, the 2'-hydroxyl at the 3' terminus can be readily and selectively derivatized with a variety of groups.

Other useful RNA derivatives incorporate nucleotides having modified carbohydrate moieties, such as 2'O-alkylated residues or 2'-O-methyl ribosyl derivatives and 2'-O-fluoro ribosyl derivatives. The RNA bases can also be modified. Any modified base useful for inhibiting or interfering with the expression of a target sequence can be used. For example, halogenated bases, such as 5-bromouracil and 5-iodouracil can be incorporated. The bases can also be alkylated, for example, 7-methylguanosine can be incorporated in place of a guanosine residue. Non-natural bases that yield successful inhibition can also be incorporated.

The most preferred siRNA modifications include 2'-deoxy-2'-fluorouridine or locked nucleic acid (LNA) nucleotides and RNA duplexes containing either phosphodiester or varying numbers of phosphorothioate linkages. Such modifications are known to one skilled in the art and are described, for example, in Braasch et al., Biochemistry, 42: 7967-7975, 2003. Most of the useful modifications to the siRNA molecules can be introduced using chemistries established for antisense oligonucleotide technology. Preferably, the modifications involve minimal 2'-O-methyl modification, preferably excluding such modification. Modifications also preferably exclude modifications of the free 5'-hydroxyl groups of the siRNA.

siRNA and miRNA molecules having various "tails" covalently attached to either their 3'- or to their 5'-ends, or to both, are also known in the art and can be used to stabilize the siRNA and miRNA molecules delivered using the methods of the present invention. Generally speaking, intercalating groups, various kinds of reporter groups and lipophilic groups attached to the 3' or 5' ends of the RNA molecules are well known to one skilled in the art and are useful according to the methods of the present invention. Descriptions of syntheses of 3'-cholesterol or 3'-acridine modified oligonucleotides applicable to preparation of modified RNA molecules useful according to the present invention can be found, for example, in the articles: Gamper, H. B., Reed, M. W., Cox, T., Virosco, J. S., Adams, A. D., Gall, A., Scholler, J. K., and Meyer, R. B. (1993) Facile Preparation and Exonuclease Stability of 3'-Modified Oligodeoxynucleotides. Nucleic Acids Res. 21 145-150; and Reed, M. W., Adams, A. D., Nelson, J. S., and Meyer, R. B., Jr. (1991) Acridine and Cholesterol-Derivatized Solid Supports for Improved Synthesis of 3'-Modified Oligonucleotides. Bioconjugate Chem. 2 217-225 (1993).

Other siRNAs useful for targeting Lp-PLA$_2$ expression can be readily designed and tested. Accordingly, siRNAs useful for the methods described herein include siRNA molecules of about 15 to about 40 or about 15 to about 28 nucleotides in length, which are homologous to an Lp-PLA$_2$ gene. Preferably, the Lp-PLA$_2$ targeting siRNA molecules have a length of about 19 to about 25 nucleotides. More preferably, the Lp-PLA$_2$ targeting siRNA molecules have a length of about 19, 20, 21, or 22 nucleotides. The Lp-PLA$_2$ targeting siRNA molecules can also comprise a 3' hydroxyl group. The Lp-PLA$_2$ targeting siRNA molecules can be single-stranded or double stranded; such molecules can be blunt ended or comprise overhanging ends (e.g., 5', 3'). In specific embodiments, the RNA molecule is double stranded and either blunt ended or comprises overhanging ends.

In one embodiment, at least one strand of the Lp-PLA$_2$ targeting RNA molecule has a 3' overhang from about 0 to about 6 nucleotides (e.g., pyrimidine nucleotides, purine nucleotides) in length. In other embodiments, the 3' overhang is from about 1 to about 5 nucleotides, from about 1 to about 3 nucleotides and from about 2 to about 4 nucleotides in length. In one embodiment the Lp-PLA$_2$ targeting RNA molecule is double stranded—one strand has a 3' overhang and the other strand can be blunt-ended or have an overhang. In the embodiment in which the Lp-PLA$_2$ targeting RNA molecule is double stranded and both strands comprise an overhang, the length of the overhangs can be the same or different for each strand. In a particular embodiment, the RNA of the present invention comprises about 19, 20, 21, or 22 nucleotides which are paired and which have overhangs of from about 1 to about 3, particularly about 2, nucleotides on both 3' ends of the RNA. In one embodiment, the 3' overhangs can be stabilized against degradation. In a preferred embodiment, the RNA is stabilized by including purine nucleotides, such as adenosine or guanosine nucleotides. Alternatively, substitution of pyrimidine nucleotides by modified analogues, e.g., substitution of uridine 2 nucleotide 3' overhangs by 2'-deoxythymidine is tolerated and does not affect the efficiency of RNAi. The absence of a 2' hydroxyl significantly enhances the nuclease resistance of the overhang in tissue culture medium.

Lp-PLA$_2$ mRNA has been successfully targeted using siRNAs and such siRNA or vectors for preparing them are commercially available, for example from Invitrogen. In some embodiments, assessment of the expression and/or knock down of Lp-PLA$_2$ protein using such Lp-PLA$_2$ siRNAs can be determined using commercially available kits, for example but are not limited to PLAC assay from diaDexus. Others can be readily prepared by those of skill in the art based on the known sequence of the target mRNA. To avoid doubt, the sequence of a human Lp-PLA$_2$ cDNA is provided at, for example, GenBank Accession Nos.: U20157 (SEQ ID NO:1) or NM_005084 (SEQ ID NO:2). The sequence at U20157 is the following (SEQ ID NO:1):

siRNA sequences are chosen to maximize the uptake of the antisense (guide) strand of the siRNA into RISC and thereby maximize the ability of RISC to target human Lp-PLA$_2$ mRNA for degradation. This can be accomplished by scanning for sequences that have the lowest free energy of binding at the 5'-terminus of the antisense strand. The lower free energy leads to an enhancement of the unwinding of the 5'-end of the antisense strand of the siRNA duplex, thereby ensuring that the antisense strand will be taken up by RISC and direct the sequence-specific cleavage of the human Lp-PLA$_2$ mRNA.

In a preferred embodiment, the siRNA or modified siRNA is delivered in a pharmaceutically acceptable carrier. Additional carrier agents, such as liposomes, can be added to the pharmaceutically acceptable carrier.

In another embodiment, the siRNA is delivered by delivering a vector encoding small hairpin RNA (shRNA) in a pharmaceutically acceptable carrier to the cells in an organ of an individual. The shRNA is converted by the cells after transcription into siRNA capable of targeting, for example, Lp-PLA$_2$. In one embodiment, the vector can be a regulatable vector, such as tetracycline inducible vector.

```
   1 gctggtcgga ggctcgcagt gctgtcggcg agaagcagtc gggtttggag cgcttgggtc 61 gcgttggtgc gcggtggaac gcgcccaggg accccagttc ccgcgagcag ctccgcgccg 121 cgcctgagag actaagctga aactgctgct cagctcccaa gatggtgcca cccaaattgc 181 atgtgctttt ctgcctctgc ggctgcctgg ctgtggttta tccttttgac tggcaataca 241 taaatcctgt tgcccatatg aaatcatcag catgggtcaa caaatacaa gtactgatgg 301 ctgctgcaag cttttggccaa actaaaatcc cccggggaaa tgggccttat tccgttggtt 361 gtacagactt aatgtttgat cacactaata agggcacctt cttgcgttta tattatccat 421 cccaagataa tgatcgcctt gacacccttt ggatcccaaa taaagaatat ttttggggtc 481 ttagcaaatt tcttggaaca cactggctta tgggcaacat tttgaggtta ctctttggtt 541 caatgacaac tcctgcaaac tggaattccc ctctgaggcc tggtgaaaaa tatccacttg 601 ttgttttttc tcatggtctt ggggcattca ggacacttta ttctgctatt ggcattgacc 661 tggcatctca tgggtttata gttgctgctg tagaacacag agatagatct gcatctgcaa 721 cttactattt caaggaccaa tctgctgcag aaatagggga caagtcttgg ctctacctta 781 gaaccctgaa acaagaggag gagacacata tacgaaatga gcaggtacgg caaagagcaa 841 aagaatgttc ccaagctctc agtctgattc ttgacattga tcatgaaag ccagtgaaga 901 atgcattaga tttaaagttt gatatggaac aactgaagga ctctattgat agggaaaaaa 961 tagcagtaat tggacattct tttggtggag caacggttat tcagactctt agtgaagatc 1021 agagattcag atgtggtatt gccctggatg catggatgtt tccactgggt gatgaagtat 1081 attccagaat tcctcagccc ctcttttta tcaactctga atatttccaa tatcctgcta 1141 atatcataaa aatgaaaaaa tgctactcac ctgataaaga aagaaagatg attacaatca 1201 ggggttcagt ccaccagaat tttgctgact tcactttgc aactggcaaa ataattggac 1261 acatgctcaa attaaaggga gacatagatt caaatgtagc tattgatctt agcaacaaag 1321 cttcattagc attcttacaa aagcatttag gacttcataa agattttgat cagtgggact 1381 gcttgattga aggagatgat gagaatctta ttccagggac caacattaac acaaccaatc 1441 aacacatcat gttacagaac tcttcaggaa tagagaaata caattaggat taaaataggt 1501 ttttt
```

In one embodiment, the RNA interfering agents used in the methods described herein are taken up actively by cells in vivo following intravenous injection, e.g., hydrodynamic injection, without the use of a vector, illustrating efficient in vivo delivery of the RNA interfering agents, e.g., the siRNAs used in the methods of the invention.

Other strategies for delivery of the RNA interfering agents, e.g., the siRNAs or shRNAs used in the methods of the invention, can also be employed, such as, for example, delivery by a vector, e.g., a plasmid or viral vector, e.g., a lentiviral vector. Such vectors can be used as described, for example, in Xiao-Feng Qin et al. Proc. Natl. Acad. Sci. U.S.A., 100: 183-188. Other delivery methods include delivery of the RNA interfering agents, e.g., the siRNAs or shRNAs of the invention, using a basic peptide by conjugating or mixing the RNA interfering agent with a basic peptide, e.g., a fragment of a TAT peptide, mixing with cationic lipids or formulating into particles.

As noted, the dsRNA, such as siRNA or shRNA can be delivered using an inducible vector, such as a tetracycline inducible vector. Methods described, for example, in Wang et al. Proc. Natl. Acad. Sci. 100: 5103-5106, using pTet-On vectors (BD Biosciences Clontech, Palo Alto, Calif.) can be used. In some embodiments, a vector can be a plasmid vector, a viral vector, or any other suitable vehicle adapted for the insertion and foreign sequence and for the introduction into eukaryotic cells. The vector can be an expression vector capable of directing the transcription of the DNA sequence of the agonist or antagonist nucleic acid molecules into RNA. Viral expression vectors can be selected from a group comprising, for example, reteroviruses, lentiviruses, Epstein Barr virus-, bovine papilloma virus, adenovirus- and adeno-associated-based vectors or hybrid virus of any of the above. In one embodiment, the vector is episomal. The use of a suitable episomal vector provides a means of maintaining the antagonist nucleic acid molecule in the subject in high copy number extra chromosomal DNA thereby eliminating potential effects of chromosomal integration.

RNA interference molecules and nucleic acid inhibitors useful in the methods as disclosed herein can be produced using any known techniques such as direct chemical synthesis, through processing of longer double stranded RNAs by exposure to recombinant Dicer protein or Drosophila embryo lysates, through an in vitro system derived from S2 cells, using phage RNA polymerase, RNA-dependant RNA polymerase, and DNA based vectors. Use of cell lysates or in vitro processing can further involve the subsequent isolation of the short, for example, about 21-23 nucleotide, siRNAs from the lysate, etc. Chemical synthesis usually proceeds by making two single stranded RNA-oligomers followed by the annealing of the two single stranded oligomers into a double stranded RNA. Other examples include methods disclosed in WO 99/32619 and WO 01/68836 that teach chemical and enzymatic synthesis of siRNA. Moreover, numerous commercial services are available for designing and manufacturing specific siRNAs (see, e.g., QIAGEN Inc., Valencia, Calif. and AMBION Inc., Austin, Tex.)

In some embodiments, an agent is protein or polypeptide or RNAi agent that inhibits expression of Lp-PLA and/or activity of the Lp-PLA$_2$ protein. In such embodiments cells can be modified (e.g., by homologous recombination) to provide increased expression of such an agent, for example by replacing, in whole or in part, the naturally occurring promoter with all or part of a heterologous promoter so that the cells express the natural inhibitor agent of Lp-PLA$_2$, for example protein or miRNA inhibitor of Lp-PLA$_2$ at higher levels. The heterologous promoter is inserted in such a manner that it is operatively linked to the desired nucleic acid encoding the agent. See, for example, PCT International Publication No. WO 94/12650 by Transkaryotic Therapies, Inc., PCT International Publication No. WO 92/20808 by Cell Genesys, Inc., and PCT International Publication No. WO 91/09955 by Applied Research Systems. Cells also can be engineered to express an endogenous gene comprising the agent under the control of inducible regulatory elements, in which case the regulatory sequences of the endogenous gene can be replaced by homologous recombination. Gene activation techniques are described in U.S. Pat. No. 5,272,071 to Chappel; U.S. Pat. No. 5,578,461 to Sherwin et al.; PCT/US92/09627 (WO93/09222) by Selden et al.; and PCT/US90/06436 (WO91/06667) by Skoultchi et al. (which are incorporated herein by reference). The agent can be prepared by culturing transformed host cells under culture conditions suitable to express the miRNA. The resulting expressed agent can then be purified from such culture (i.e., from culture medium or cell extracts) using known purification processes, such as gel filtration and ion exchange chromatography. The purification of the peptide or nucleic acid agent inhibitor of Lp-PLA$_2$ can also include an affinity column containing agents which will bind to the protein; one or more column steps over such affinity resins as concanavalin A-agarose, Heparin-toyopearl™ or Cibacrom blue 3GA Sepharose; one or more steps involving hydrophobic interaction chromatography using such resins as phenyl ether, butyl ether, or propyl ether; immunoaffinity chromatography, or complementary cDNA affinity chromatography.

In one embodiment, the nucleic acid inhibitors of Lp-PLA$_2$ can be obtained synthetically, for example, by chemically synthesizing a nucleic acid by any method of synthesis known to the skilled artisan. The synthesized nucleic acid inhibitors of Lp-PLA$_2$ can then be purified by any method known in the art. Methods for chemical synthesis of nucleic acids include, but are not limited to, in vitro chemical synthesis using phosphotriester, phosphate or phosphoramidite chemistry and solid phase techniques, or via deoxynucleoside H-phosphonate intermediates (see U.S. Pat. No. 5,705,629 to Bhongle, which is incorporated herein by reference).

In some circumstances, for example, where increased nuclease stability is desired, nucleic acids having nucleic acid analogs and/or modified internucleoside linkages can be preferred. Nucleic acids containing modified internucleoside linkages can also be synthesized using reagents and methods that are well known in the art. For example, methods of synthesizing nucleic acids containing phosphonate phosphorothioate, phosphorodithioate, phosphoramidate methoxyethyl phosphoramidate, formacetal, thioformacetal, diisopropylsilyl, acetamidate, carbamate, dimethylene-sulfide ($-CH_2-S-CH_2-$), dimethylene-sulfoxide ($-CH_2-SO-CH_2$), dimethylene-sulfone ($-CH_2-SO_2-CH_2$), 2'-O-alkyl, and 2'-deoxy-2'-fluoro 'phosphorothioate internucleoside linkages are well known in the art (see Uhlmann et al., 1990, Chem. Rev. 90:543-584; Schneider et al., 1990, Tetrahedron Lett. 31:335 and references cited therein). U.S. Pat. Nos. 5,614,617 and 5,223,618 to Cook, et al., U.S. Pat. No. 5,714,606 to Acevedo, et al, U.S. Pat. No. 5,378,825 to Cook, et al., U.S. Pat. Nos. 5,672,697 and U.S. Pat. No. 5,466,786 to Buhr, et al., 5, 777,092 to Cook, et al., U.S. Pat. No. 5,602,240 to De Mesmacker, et al., U.S. Pat. No. 5,610,289 to Cook, et al. and U.S. Pat. No. 5,858,988 to Wang, which are incorporated herein by reference, also describe nucleic acid analogs for enhanced nuclease stability and cellular uptake.

Synthetic siRNA molecules, including shRNA molecules, can be obtained using a number of techniques known to those of skill in the art. For example, the siRNA molecule can be chemically synthesized or recombinantly produced using methods known in the art, such as using appropriately protected ribonucleoside phosphoramidites and a conventional DNA/RNA synthesizer (see, e.g., Elbashir, S. M. et al. (2001) *Nature* 411:494-498; Elbashir, S. M., W. Lendeckel and T. Tuschl (2001) *Genes & Development* 15:188-200; Harborth, J. et al. (2001) *J. Cell Science* 114:4557-4565; Masters, J. R. et al. (2001) *Proc. Natl. Acad. Sci., USA* 98:8012-8017; and Tuschl, T. et al. (1999) *Genes & Development* 13:3191-3197). Alternatively, several commercial RNA synthesis suppliers are available including, but are not limited to, Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA), and Cruachem (Glasgow, UK). As such, siRNA molecules are not overly difficult to synthesize and are readily provided in a quality suitable for RNAi. In addition, dsRNAs can be expressed as stem loop structures encoded by plasmid vectors, retroviruses and lentiviruses (Paddison, P. J. et al. (2002) *Genes Dev.* 16:948-958; McManus, M. T. et al. (2002) *RNA* 8:842-850; Paul, C. P. et al. (2002) *Nat. Biotechnol.* 20:505-508; Miyagishi, M. et al. (2002) *Nat. Biotechnol.* 20:497-500; Sui, G. et al. (2002) *Proc. Natl. Acad. Sci., USA* 99:5515-5520; Brummelkamp, T. et al. (2002) *Cancer Cell* 2:243; Lee, N. S., et al. (2002) *Nat. Biotechnol.* 20:500-505; Yu, J. Y., et al. (2002) *Proc. Natl. Acad. Sci., USA* 99:6047-6052; Zeng, Y., et al. (2002) *Mol. Cell.* 9:1327-1333; Rubinson, D. A., et al. (2003) *Nat. Genet.* 33:401-406; Stewart, S. A., et al. (2003) *RNA* 9:493-501). These vectors generally have a polIII promoter upstream of the dsRNA and can express sense and antisense RNA strands separately and/or as a hairpin structures. Within cells, Dicer processes the short hairpin RNA (shRNA) into effective siRNA.

The targeted region of the siRNA molecule of the present invention can be selected from a given target gene sequence, e.g., a Lp-PLA$_2$ coding sequence, beginning from about 25 to 50 nucleotides, from about 50 to 75 nucleotides, or from about 75 to 100 nucleotides downstream of the start codon. Nucleotide sequences can contain 5' or 3' UTRs and regions nearby the start codon. One method of designing a siRNA molecule of the present invention involves identifying the 23 nucleotide sequence motif AA(N19)TT (where N can be any nucleotide), and selecting hits with at least 25%, 30%, 35%, 40%, 45%, 50%, 55%, 60%, 65%, 70% or 75% G/C content. The "TT" portion of the sequence is optional. Alternatively, if no such sequence is found, the search can be extended using the motif NA(N21), where N can be any nucleotide. In this situation, the 3' end of the sense siRNA can be converted to TT to allow for the generation of a symmetric duplex with respect to the sequence composition of the sense and antisense 3' overhangs. The antisense siRNA molecule can then be synthesized as the complement to nucleotide positions 1 to 21 of the 23 nucleotide sequence motif. The use of symmetric 3' TT overhangs can be advantageous to ensure that the small interfering ribonucleoprotein particles (siRNPs) are formed with approximately equal ratios of sense and antisense target RNA-cleaving siRNPs (Elbashir et al. (2001) supra and Elbashir et al. 2001 supra). Analysis of sequence databases, including but are not limited to the NCBI, BLAST, Derwent and GenSeq as well as commercially available oligosynthesis software such as Oligoengine®, can also be used to select siRNA sequences against EST libraries to ensure that only one gene is targeted.

Delivery of RNA Interfering Agents: Methods of delivering RNA interfering agents, e.g., an siRNA, or vectors containing an RNA interfering agent, to the target cells (e.g., cells of the brain or other desired target cells, for cells in the central and peripheral nervous systems), can include, for example (i) injection of a composition containing the RNA interfering agent, e.g., an siRNA, or (ii) directly contacting the cell, e.g., a cell of the brain, with a composition comprising an RNA interfering agent, e.g., an siRNA. In another embodiment, RNA interfering agents, e.g., an siRNA can be injected directly into any blood vessel, such as vein, artery, venule or arteriole, via, e.g., hydrodynamic injection or catheterization. In some embodiments, the siRNA is delivered to the bone marrow, where Lp-PLA$_2$ is secreted from bone marrow-derived cells such as leukocytes.

Administration can be by a single injection or by two or more injections. The RNA interfering agent is delivered in a pharmaceutically acceptable carrier. One or more RNA interfering agents can be used simultaneously. The RNA interfering agents, e.g., the siRNAs targeting Lp-PLA$_2$ mRNA, can be delivered singly, or in combination with other RNA interfering agents, e.g., siRNAs, such as, for example siRNAs directed to other cellular genes. Lp-PLA$_2$ siRNAs can also be administered in combination with other pharmaceutical agents which are used to treat or prevent metabolic bone diseases or disorders.

In one embodiment, specific cells are targeted with RNA interference, limiting potential side effects of RNA interference caused by non-specific targeting of RNA interference. The method can use, for example, a complex or a fusion molecule comprising a cell targeting moiety and an RNA interference binding moiety that is used to deliver RNA interference effectively into cells. For example, an antibody-protamine fusion protein when mixed with an siRNA, binds siRNA and selectively delivers the siRNA into cells expressing an antigen recognized by the antibody, resulting in silencing of gene expression only in those cells that express the antigen. The siRNA or RNA interference-inducing molecule binding moiety is a protein or a nucleic acid binding domain or fragment of a protein, and the binding moiety is fused to a portion of the targeting moiety. The location of the targeting moiety can be either in the carboxyl-terminal or amino-terminal end of the construct or in the middle of the fusion protein.

A viral-mediated delivery mechanism can also be employed to deliver siRNAs to cells in vitro and in vivo as described in Xia, H. et al. (2002) *Nat Biotechnol* 20(10): 1006). Plasmid- or viral-mediated delivery mechanisms of shRNA can also be employed to deliver shRNAs to cells in vitro and in vivo as described in Rubinson, D. A., et al. ((2003) *Nat. Genet.* 33:401-406) and Stewart, S. A., et al. ((2003) *RNA* 9:493-501).

RNA interfering agents, for e.g., an siRNA, can also be introduced into cells via the vascular or extravascular circulation, the blood or lymph system, and the cerebrospinal fluid.

The dose of the particular RNA interfering agent will be in an amount necessary to effect RNA interference, e.g., post translational gene silencing (PTGS), of the particular target gene, thereby leading to inhibition of target gene expression or inhibition of activity or level of the protein encoded by the target gene.

It is also known that RNAi molecules do not have to match perfectly to their target sequence. Preferably, however, the 5' and middle part of the antisense (guide) strand of the siRNA is perfectly complementary to the target nucleic acid sequence.

Accordingly, the RNAi molecules functioning as nucleic acid inhibitors of Lp-PLA$_2$ in the present invention are for example, but are not limited to, unmodified and modified double stranded (ds) RNA molecules including short-temporal RNA (stRNA), small interfering RNA (siRNA), short-hairpin RNA (shRNA), microRNA (miRNA), double-stranded RNA (dsRNA), (see, e.g. Baulcombe, *Science* 297: 2002-2003, 2002). The dsRNA molecules, e.g. siRNA, also can contain 3' overhangs, preferably 3'UU or 3'TT overhangs. In one embodiment, the siRNA molecules of the present invention do not include RNA molecules that comprise ssRNA greater than about 30-40 bases, about 40-50 bases, about 50 bases or more. In one embodiment, the siRNA molecules of the present invention are double stranded for more than about 25%, more than about 50%, more than about 60%, more than about 70%, more than about 80%, more than about 90% of their length. In some embodiments, a nucleic acid inhibitor of $Lp-PLA_2$ is any agent which binds to and inhibits the expression of $Lp-PLA_2$ mRNA, where the expression of $Lp-PLA_2$ mRNA or a product of transcription of nucleic acid encoded by SEQ ID NO: 1 or 2 is inhibited.

In another embodiment of the invention, agents inhibiting $Lp-PLA_2$ are catalytic nucleic acid constructs, such as, for example ribosomes, which are capable of cleaving RNA transcripts and thereby preventing the production of wildtype protein. Ribosomes are targeted to and anneal with a particular sequence by virtue of two regions of sequence complementary to the target flanking the ribosome catalytic site. After binding, the ribozyme cleaves the target in a site specific manner. The design and testing of ribosomes which specifically recognize and cleave sequences of the gene products described herein, for example for cleavage of $Lp-PLA_2$ or homologues or variants thereof can be achieved by techniques well known to those skilled in the art (for example Lleber and Strauss, (1995) Mol Cell Biol 15:540.551, the disclosure of which is incorporated herein by reference).

Proteins and Peptide Inhibitors of $Lp-PLA_2$

In some embodiments, agent that inhibit $Lp-PLA_2$ are proteins and/or peptide inhibitors or fragments of inhibitors of $Lp-PLA_2$, for example, but are not limited to mutated proteins; therapeutic proteins and recombinant proteins. Proteins and peptides inhibitors can also include for example mutated proteins, genetically modified proteins, peptides, synthetic peptides, recombinant proteins, chimeric proteins, antibodies, humanized proteins, humanized antibodies, chimeric antibodies, modified proteins and fragments thereof.

In some embodiments, the agents that inhibit $Lp-PLA_2$ are dominant negative variants of $Lp-PLA_2$, for example a non-functional variant of $Lp-PLA_2$.

Antibodies

In some embodiments, inhibitors of genes and/or gene products useful in the methods of the present invention include, for example, antibodies, including monoclonal, chimeric humanized, and recombinant antibodies and antigen-binding fragments thereof. In some embodiments, neutralizing antibodies can be used as inhibitors of the $Lp-PLA_2$ enzyme. Antibodies are readily raised in animals such as rabbits or mice by immunization with the antigen. Immunized mice are particularly useful for providing sources of B cells for the manufacture of hybridomas, which in turn are cultured to produce large quantities of monoclonal antibodies.

In one embodiment of this invention, the inhibitor to the gene products identified herein can be an antibody molecule or the epitope-binding moiety of an antibody molecule and the like. Antibodies provide high binding avidity and unique specificity to a wide range of target antigens and haptens. Monoclonal antibodies useful in the practice of the present invention include whole antibody and fragments thereof and are generated in accordance with conventional techniques, such as hybridoma synthesis, recombinant DNA techniques and protein synthesis.

Useful monoclonal antibodies and fragments can be derived from any species (including humans) or can be formed as chimeric proteins which employ sequences from more than one species. Human monoclonal antibodies or "humanized" murine antibody are also used in accordance with the present invention. For example, murine monoclonal antibody can be "humanized" by genetically recombining the nucleotide sequence encoding the murine Fv region (i.e., containing the antigen binding sites) or the complementarily determining regions thereof with the nucleotide sequence encoding a human constant domain region and an Fc region. Humanized targeting moieties are recognized to decrease the immunoreactivity of the antibody or polypeptide in the host recipient, permitting an increase in the half-life and a reduction the possibly of adverse immune reactions in a manner similar to that disclosed in European Patent Application No. 0,411,893 A2. The murine monoclonal antibodies should preferably be employed in humanized form. Antigen binding activity is determined by the sequences and conformation of the amino acids of the six complementarily determining regions (CDRs) that are located (three each) on the light and heavy chains of the variable portion (Fv) of the antibody. The 25-kDa single-chain Fv (scFv) molecule, composed of a variable region (VL) of the light chain and a variable region (VH) of the heavy chain joined via a short peptide spacer sequence, is the smallest antibody fragment developed to date. Techniques have been developed to display scFv molecules on the surface of filamentous phage that contain the gene for the scFv. scFv molecules with a broad range of antigenic-specificities can be present in a single large pool of scFv-phage library. Some examples of high affinity monoclonal antibodies and chimeric derivatives thereof, useful in the methods of the present invention, are described in the European Patent Application EP 186,833; PCT Patent Application WO 92/16553; and U.S. Pat. No. 6,090,923.

Chimeric antibodies are immunoglobin molecules characterized by two or more segments or portions derived from different animal species. Generally, the variable region of the chimeric antibody is derived from a non-human mammalian antibody, such as murine monoclonal antibody, and the immunoglobin constant region is derived from a human immunoglobin molecule. Preferably, both regions and the combination have low immunogenicity as routinely determined.

One limitation of scFv molecules is their monovalent interaction with target antigen. One of the easiest methods of improving the binding of a scFv to its target antigen is to increase its functional affinity through the creation of a multimer. Association of identical scFv molecules to form diabodies, triabodies and tetrabodies can comprise a number of identical Fv modules. These reagents are therefore multivalent, but monospecific. The association of two different scFv molecules, each comprising a VH and VL domain derived from different parent Ig will form a fully functional bispecific diabody. A unique application of bispecific scFvs is to bind two sites simultaneously on the same target molecule via two (adjacent) surface epitopes. These reagents gain a significant avidity advantage over a single scFv or Fab fragments. A number of multivalent scFv-based structures has been engineered, including for example, miniantibodies, dimeric miniantibodies, minibodies, $(scFv)_2$, diabodies and triabodies. These molecules span a range of valence (two to four binding sites), size (50 to 120 kDa), flexibility and ease of production. Single chain Fv antibody fragments (scFvs) are predominantly monomeric when the VH and VL domains are joined by, polypeptide linkers of at least 12 residues. The monomer scFv is thermodynamically stable with linkers of 12 and 25 amino acids length under all conditions. The noncovalent diabody and triabody molecules are easy to engineer and are produced by shortening the peptide linker that connects the variable heavy and variable light chains of a single scFv molecule. The scFv dimers are joined by amphipathic helices that offer a high degree of flexibility and the miniantibody structure can be modified to create a dimeric bispecific (DiBi) miniantibody that contains two miniantibodies (four scFv molecules) connected via a double helix. Gene-fused or disulfide bonded scFv dimers provide an intermediate degree of flexibility and are generated by straightforward cloning techniques adding a C-terminal Gly4Cys sequence. scFv-CH3 minibodies are comprised of two scFv molecules joined to an IgG CH3 domain either directly (LD minibody) or via a very flexible hinge region (Flex minibody). With a molecular weight of approximately 80 kDa, these divalent constructs are capable of significant binding to antigens. The Flex minibody exhibits impressive tumor localization in mice. Bi- and tri-specific multimers can be formed by association of different scFv molecules. Increase in functional affinity can be reached when Fab or single chain Fv antibody fragments (scFv) fragments are complexed into dimers, trimers or larger aggregates. The most important advantage of multivalent scFvs over monovalent scFv and Fab fragments is the gain in functional binding affinity (avidity) to target antigens. High avidity requires that scFv multimers are capable of binding simultaneously to separate target antigens. The gain in functional affinity for scFv diabodies compared to scFv monomers is significant and is seen primarily in reduced off-rates, which result from multiple binding to two or more target antigens and to rebinding when one Fv dissociates. When such scFv molecules associate into multimers, they can be designed with either high avidity to a single target antigen or with multiple specificities to different target antigens. Multiple binding to antigens is dependent on correct alignment and orientation in the Fv modules. For full avidity in multivalent scFvs target, the antigen binding sites must point towards the same direction. If multiple binding is not sterically possible then apparent gains in functional affinity are likely to be due the effect of increased rebinding, which is dependent on diffusion rates and antigen concentration. Antibodies conjugated with moieties that improve their properties are also contemplated for the instant invention. For example, antibody conjugates with PEG that increases their half-life in vivo can be used for the present invention. Immune libraries are prepared by subjecting the genes encoding variable antibody fragments from the B lymphocytes of naive or immunized animals or patients to PCR amplification. Combinations of oligonucleotides which are specific for immunoglobulin genes or for the immunoglobulin gene families are used. Immunoglobulin germ line genes can be used to prepare semisynthetic antibody repertoires, with the complementarity-determining region of the variable fragments being amplified by PCR using degenerate primers. These single-pot libraries have the advantage that antibody fragments against a large number of antigens can be isolated from one single library. The phage-display technique can be used to increase the affinity of antibody fragments, with new libraries being prepared from already existing antibody fragments by random, codon-based or site-directed mutagenesis, by shuffling the chains of individual domains with those of fragments from naive repertoires or by using bacterial mutator strains.

Alternatively, a SCID-hu mouse, for example the model developed by Genpharm, can be used to produce antibodies, or fragments thereof. In one embodiment, a new type of high avidity binding molecule, termed peptabody, created by harnessing the effect of multivalent interaction is contemplated. A short peptide ligand was fused via a semirigid hinge region with the coiled-coil assembly domain of the cartilage oligomeric matrix protein, resulting in a pentameric multivalent binding molecule. In preferred embodiment of this invention, ligands and/or chimeric inhibitors can be targeted to tissue- or tumor-specific targets by using bispecific antibodies, for example produced by chemical linkage of an anti-ligand antibody (Ab) and an Ab directed toward a specific target. To avoid the limitations of chemical conjugates, molecular conjugates of antibodies can be used for production of recombinant bispecific single-chain Abs directing ligands and/or chimeric inhibitors at cell surface molecules. Alternatively, two or more active agents and or inhibitors attached to targeting moieties can be administered, wherein each conjugate includes a targeting moiety, for example, a different antibody. Each antibody is reactive with a different target site epitope (associated with the same or a different target site antigen). The different antibodies with the agents attached accumulate additively at the desired target site. Antibody-based or non-antibody-based targeting moieties can be employed to deliver a ligand or the inhibitor to a target site. Preferably, a natural binding agent for an unregulated or disease associated antigen is used for this purpose.

Bioassay for Identifying Lp-PLA$_2$ Inhibitors:

Screen for Inhibition of Lp-PLA$_2$ Protein

In some embodiments, the methods of the present invention relate to use of inhibitors of Lp-PLA$_2$ for the prevention and/or treatment of metabolic bone diseases or disorders, for example osteoporosis and osteopenic related diseases. Where necessary, agents that inhibit Lp-PLA$_2$ protein are assessed using a bioassay, as disclosed in U.S. Pat. No. 5,981,252 which is incorporated herein in its entirety by reference. One such assay is testing the effect of the agent on the recombinant Lp-PLA$_2$ protein. In one assay, for example, recombinant Lp-PLA$_2$ is purified to homogeneity from baculovirus infected Sf9 cells, using a zinc chelating column, blue sepharose affinity chromatography and an anion exchange column. Following purification and ultrafiltration, the enzyme can be stored at 6 mg/ml at 4° C. Assay buffer comprises Tris-HCl (50 mM), NaCl (150 mM) and 1 mM CHAPS, pH 7.4 at room temperature. Activity is measured by an increase in emission at 535 nm on hydrolysis of N-((6-(2,4-dinitrophenyl)amino)hexanoyl)-2-(4,4-difluoro-5,7-dimethyl-4-bora-3a,4a-diaza-s-indacene-3-pentanoyl)-1-hexadecanoyl-sn-glycero-3-phosphoethanolamine, triethylammonium salt (PED6, Molecular Probes catalogue reference D-23739) as substrate, using a fluorometric plate reader with 384 well microtitre plates. Reaction is initiated by the addition of enzyme (approx 400 pM final by weight) and substrate (5 μM final) to inhibitor in a total volume of 10 microliters.

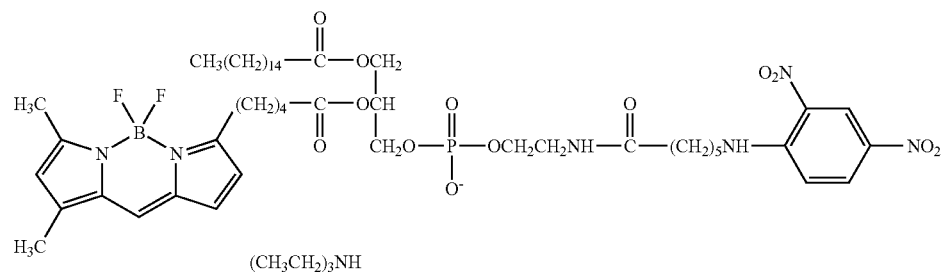

(PED6)

The compounds as disclosed herein, for example as disclosed in the sections entitled of Examples of synethesis were tested and were found to have $IC_{50}$ values in the range 0.1 to 10 nM.

Uses of Agents that Inhibit Lp-PLA$_2$ for the Prevention and/or Treatment of Metabolic Bone Diseases or Disorders.

One aspect of the present invention relates to methods for the treatment and/or prevention of metabolic bone diseases or disorders. These include metabolic bone diseases and/or disorders are characterized by abnormalities in the bone marrow. The method uses agents that inhibit the expression and/or function of Lp-PLA$_2$. In some embodiments, the metabolic bone disease or disorder is osteoporosis and osteopenia, and in other embodiments the metabolic bone disease or disorders can be caused by metabolic diseases such as dyslipidemia, type II diabetes, metabolic syndrome or insulin resistance and the like.

Bone marrow homeostasis is critical for tissue repair and regeneration. Disturbed bone marrow homeostasis may lead to aging and tissue degeneration. As disclosed herein, inhibition of Lp-PLA$_2$ can also be used for the prevention and/or treatment of metabolic bone marrow diseases or disorders and bone marrow abnormalities.

In other embodiments, agents inhibiting Lp-PLA$_2$ as disclosed herein are useful in the treatment and/or prophylaxis of diseases where metabolic bone disease occurs or disorders where loss of bone mass, or bone density has been determined to play a role, such as osteoporosis and related osteopenic diseases, Paget's disease, hyperparathyroidism and related diseases, such as for example dyslipidemia, type II diabetes, metabolic syndrome or insulin resistance and the like.

In some embodiments, the osteopenic related disease or osteoporosis is associated with the peri and post menopausal conditions. Also encompassed are the treatment and prophylaxis of Paget's disease, hypercalcemia associated with bone neoplasms and all the types of osteoporotic diseases as classified below according to their etiology: Primary osteoporosis, hypercalcemia, involutional osteoporosis, Type I or postmenopausal osteoporosis, Type II or senile osteoporosis, Juvenile osteoporosis, Idiopathic in young adults osteoporosis, Secondary osteoporosis, Endocrine abnormality, Hyperthyroidism, Hypogonadism, Ovarian agenesis, or Turner's syndrome, Hyperadrenocorticism or Cushing's syndrome, Hyperparathyroidism, Bone marrow abnormalities, Multiple myeloma and related disorders, and Systemic mastocytosis, disseminated carcinoma osteoporosis, Gaucher's disease, Connective tissue abnormalities, Osteogenesis imperfecta, Homocystinuria, Ehlers-Danlos syndrome, Marfan's syndrome, Menke's syndrome, Miscellaneous causes Immobilisation or weightlessness, Sudeck's atrophy, chronic obstructive pulmonary disease, chronic alcoholism, chronic heparin administration and chronic ingestion of anticonvulsant drugs Patients amenable to treatment by agents inhibiting Lp-PLA$_2$ as disclosed herein include patients at risk of disease but not showing symptoms (for example asymptomatic patients), as well as patients presently showing symptoms. In the case of osteoporosis, virtually anyone, particularity women are at risk of suffering from osteoporosis if he or she lives long enough.

The methods as disclosed herein are especially useful for patients who do have a known genetic risk of metabolic bone diseases and/or disorders, for example osteoporosis. Such patients include those as identified to have risk of having a metabolic bone disease or disorder, as disclosed herein in the section entitled "osteoporosis risk factors" below, which include analysis of risk factors and analysis of genetic or biochemical markers. In some embodiments, patients are women, for example post menopausal, or women at least 65 years of age, or patients who have had previous fractures or have relatives who have had a metabolic bone disease, for example osteoporosis. Patients can be identified as having increased risk of developing metabolic bone disease using methods commonly known by person of ordinary skill in the art, and are disclosed herein in the section entitled "methods to identify patients at risk of, or having a metabolic bone disease or osteoporosis" below, which include analysis of genetic and/or biochemical markers for metabolic bone diseases as disclosed herein.

Osteoporosis

Osteoporosis (gr: osteon bone; poros hole) is described in general terms as a reduction in bone density with retention of a normal chemical composition. More specifically, osteoporosis is a generalized, progressive diminution of bone density, i.e. bone mass per unit volume, causing skeletal weakness, although the ratio of mineral to organic elements is unchanged. 30 to 40% of the skeletal mass must be lost in order to reliably diagnose osteoporosis by radiology. Contemporary medicine distinguishes between primary and secondary osteoporosis (The Merck Manual of Diagnosis and Therapy, 17th ed., 1999). Primary osteoporosis includes idiopathic osteoporosis, rare but occurring in children and young adults; postmenopausal osteoporosis, occurring between the ages of 50 and 75; and involutional or senile osteoporosis associated with the normal process of aging. In some embodiments, osteoporosis is characterized by increased osteoclast activity and a disruption of the feedback mechanism between the serum calcium level and the parathyroid hormone (PTH) secretion. It occurs mainly uniformly throughout the whole skeleton. Secondary osteoporosis, accounting for less than 5% of all osteoporosis cases, includes endocrine dysfunctions. It starts mostly at the main skeleton and progresses centrifugally. Osteoporosis is characterized by pain in the respective bones, diffuse back pain, vertebral body collapse, pathological fractures, in particular, fracture of the neck of the femur. The goal of the management of all types of osteoporosis is therefore to decrease pain, to prevent fractures and to maintain the body functions.

The cause of osteoporosis has not been fully clarified. According to one theory, osteoporosis is a calcium dysfunction and the use of calcium supplements has been widely suggested. However, so far, no reossification of the osteoporotic bone after calcium therapy could be demonstrated.

Other Metabolic Bone Disorders and Osteopenic Related Diseases.

In some embodiments, agents inhibiting Lp-PLA$_2$ using the agents as disclosed herein are useful in preventing and treating metabolic bone diseases and disorders. Additional examples of metabolic bone diseases include osteoporosis. Osteoporosis is a common clinical feature and common complication in patients affected with chronic inflammatory diseases with joint manifestations. These include rheumatoid arthritis (RA), Juvenile Rheumatoid Arthritis (JRA), psoriatic arthritis, Reiter's syndrome (reactive arthritis), Crohn's disease, ulcerative colitis and sarcoidosis (Orcel, et al., Bone demineralization and cytokines; Rev Rhum Mal Osteoartic. 1992; 59:16 S-22S; Brown, et al., The radiology of rheumatoid arthritis. Am Fam Physician. 1995. 52:1372-80; De Vos, et al., Bone and joint diseases in inflammatory bowel disease. Aliment Pharmacol Ther. 1998; 12(5):397-404; Falcini, et al., The primary role of steroids on the osteoporosis in juvenile rheumatoid patients evaluated by dual energy X-ray absorptiometry. J Endocrinol Invest. 1996; 19(3):165-9; Scutellari, et al., Rheumatoid arthritis: sequences. Eur J Radiol. 1998: Suppl 1:S31-8).

Rheumatoid arthritis is associated with a decrease in bone mass (Cortet, et al., Evaluation of bone mineral density in patients with rheumatoid arthritis. Influence of disease activity and glucocorticoid therapy. Rev Rhum Engl Ed. 1997 July-Sep. 30, 1997; 64(7-9):451-8). Typical changes of an inflammatory arthritis include juxta-articular osteoporosis, cartilage loss, and cortical or marginal bone erosions (Lawson, et al., Lyme arthritis: radiologic findings. Radiology. 1985; 154(1):37-43; Grassi, et al., The clinical features of rheumatoid arthritis. Eur J Radiol. 1998; 1:S18-24).

Three forms of bone disease (bone loss) have been described in rheumatoid arthritis, namely: focal bone loss affecting the immediate subchondral bone and bone at the joint margins; periarticular osteopenia adjacent to inflamed joints; and generalized osteoporosis involving the axial and appendicular skeleton (Goldring, et al., Mechanisms of bone loss in inflammatory arthritis: diagnosis and therapeutic implications. Arthritis Res. 2000; 2(1):33-7).

During chronic inflammatory joint diseases, such as rheumatoid arthritis, synovial cells produce large amounts of cytokines leading to increased local bone resorption and juxta-articular bone destructions (Orcel, P et al., Bone demineralization and cytokines. Rev Rhum Mal Osteoartic. 1992; 59(6 Pt 2):16S-22S).

Homocysteinemia (the accumulation of homocysteine in plasma and tissue) is the result of deficiencies of certain enzymes and/or substrates involved in the transmethylation pathways. It is caused by the accumulation of homocysteine and its two disulfides in plasma and tissue (Mudd et al., The Metabolic Basis of Inherited Disease, New York, McGraw-Hill, 1978, p. 458). Homocysteinemia is associated with juvenile arteriosclerosis, recurrent arterial and venous thromboembolic manifestations and osteoporosis. The latter may be due to the fact that homocysteine also interferes with collagen synthesis, and it is this interaction that may be significant in the development of defective bone matrix and osteoporosis (Am J Med Sci, 273, 1977, p. 120). Folic acid has been described as a successful tool for the treatment of hyperhomocysteinemia (Brattstrom et al., Metabolism, Vol. 34, No. 11, 1985, p. 1073). The metabolite transforming homocysteine to methionine is the active form of folic acid: 5-methyl-tetrahydrafolic acid (5-MTHF). Depending on the degree of methylene tetrahydrofolate reductase (MTHFR) dysfunction, the body can less or more easily transform the various forms of folates into 5-MTHF.

In some embodiments, agents that inhibit Lp-PLA$_2$ as disclosed herein are also useful in the treatment of other metabolic bone disorders, for example but not limited to patients with metabolic bone diseases due to chronic inflammatory diseases with joint manifestations, for example but not limited to rheumatoid arthritis (RA), Juvenile Rheumatoid Arthritis (JRA), psoriatic arthritis, Reiter's syndrome (reactive arthritis), Crohn's disease, ulcerative colitis, sarcoidosis. Other patients with metabolic bone diseases include, for example but are not limited to, related osteopenic diseases, Paget's disease, hyperparathyroidism and related diseases, such as for example dyslipidemia, type II diabetes, metabolic syndrome or insulin resistance and the like, primary osteoporosis, involutional osteoporosis, Type I or postmenopausal osteoporosis, Type II or senile osteoporosis, oral bone loss, metabolic peridontilis, Juvenile Idiopathic osteoporosis in young adults, Secondary osteoporosis, Endocrine abnormality, Hyperthyroidism, Hypogonadism, Ovarian agenesis or Turner's syndrome, Hyperadrenocorticism or Cushing's syndrome, Hyperparathyroidism, Bone marrow abnormalities, Multiple myeloma and related disorders, Systemic mastocytosis, Disseminated carcinoma, Gaucher's disease, Connective tissue abnormalities, Osteogenesis imperfecta, Homocystinuria, Ehlers-Danlos syndrome, Marfan's syndrome, Menke's syndrome, Miscellaneous causes, Immobilisation or weightlessness, Sudeck's atrophy, Chronic obstructive pulmonary disease, Chronic alcoholism, Chronic heparin administration and Chronic ingestion of anticonvulsant drugs.

In some embodiments, agents that inhibit Lp-PLA$_2$ as disclosed herein are also useful in the treatment of other metabolic bone disorders, for example but not limited to patients with metabolic bone diseases where the metabolic bone disease or disorder involves bone reabsorbtion, for example Paget's Disease, primary and secondary hyperparathyroidism, humoral hypercalcameia of malignancy and various cancers, where bone resorbtion is increased.

Metabolic Bone Disorders with Abnormal Bone Marrow.

The bone marrow is an organ responsible for part of haematopoiesis, and since it is in contact with the medullary cavity and cancellus bone it is possible that, as a result of bone marrow abnormalities, abnormalities in the bone and other surrounding tissues can occur and result in serious illness in the patient. Bone marrow abnormalities referred to here are defined as those where general abnormality of the biological balance in the bone marrow is indicated, such as viral and bacterial infections in the bone marrow, cellular infiltration of the bone marrow, abnormalities of the bone marrow haematopoiesis, proliferation of malignant neoplasms in the bone marrow and concentration changes in cell growth-differentiation factors.

Bone marrow abnormalites include, but are not limited to, anemia, immunodeficiency, bone marrow, depression, bone marrow fibrosis, bone marrow necrosis and degeneration.

Metabolic bone diseases or disorders and abnormal bone marrow can be brought about by many pathogenic factors such as pyogenic bacteria, tuberculosis, syphilis, fungi and specified viruses or exogenous matter is termed osteomyelitis and, when there is osteomyelitis, as a result of the impeded blood circulation and infiltration of neutrophils into the bone marrow region, there occur surrounding bone decalcification and tissue breakdown, with resulting pain. While the occurrence of acute osteomyelitis is declining due to the widespread use of antibiotics, as a result of the appearance of resistant microorganisms, osteomyelitis which from the outset follows a subacute or chronic course remains a problem [Green, et al., J. Bone Joint Serg., 63-A, p 107-114 (1981)].

In rheumatoid arthritis, it has been reported that there is an increase in the concentration of components which induce a proliferation of synoviocytes in the bone marrow and, moreover, that abnormal myelocytes are found within the bone marrow and changes in cell ratios such as an increase in the T cell ratio are shown [Ochi, T., Igaku no Ayumi, 161, p 609-613 (1992)]. Since myelocytes differentiate into neutrophils, it can be expected that the number of neutrophils showing abnormal activity will increase in the bone marrow and contribute to an aggravation of the condition. Moreover, since the progress of a condition where marked changes in the bone marrow are exhibited is rapid and the outlook for the patient is severe [Ochi, T. et al., Arthritis Rheum., 31, p 37 (1988)], there is the possibility that early stage improvement in the pathological changes in the bone marrow could be linked to the cure of the disease. In addition, in the treatment of rheumatoid arthritis there is also the problem that there is a considerable likelihood of multiple agents which show serious side effects being used concomitantly, such as steroids which display a variety of adverse-side effects and gold preparations compounds which exhibit hematopoiesis decrease.

In leukaemia, irrespective of cell type and whether it is acute or chronic, or whether it is myelogenicor lymphocytic leukaemia, the bone marrow is the location of a markedly increased production of leukaemia cells, and normal blood components decline. Again, in multiple myeloma, a principal feature is the proliferation of tumours of plasma cells, which are cells at the end of the B cell lineage, and a multiplicity of these is produced in the bone marrow at sites of active haematopoiesis. In leukaemia, multiple myeloma and the like, an increase in cell growth-differentiation factor activity in the bone marrow and an abnormal proliferation of cells are found, and the abnormalities in the biological balance in the bone marrow are believed to be closely connected with the presentation and continuance of the diseased state.

Thus, inflammatory cell infiltration into the bone marrow, abnormal cell proliferation or an abnormal increase in cell growth-differentiation factor activity in the bone marrow are closely related with many bone marrow abnormalities, and the agents that inhibit Lp-PLA$_2$ as disclosed herein can prevent and/or correct the biological balance in the bone marrow and used for the prevention and/or treatment of bone marrow abnormalities. The aforementioned disorders as disclosed herein to which bone marrow abnormalities are disclosed are given as examples, and there are no restrictions thereto.

In yet another aspect, as disclosed herein methods for the treatment and/or prophylaxis of a metabolic bone disease or disorder, including secondary conditions of a metabolic bone disease are provided. A metabolic bone disease or disorder also encompasses disease and disorders with overactivity of osteocasts. In some embodiments, disease or disorders associated with osteocast activity includes for example but are not limited to osteoporosis, Paget's disease, hypercalcemeia, rheumatoid arthritis, cancer, metastatic bone destruction, oral bone loss, metabolic peridontitis and immune disorders.

Thus, treatment can be directed to a patient who is affected with asymptomatic metabolic bone diseases; it can prevent bone density loss and/or improve bone matrix density. The efficacy of treatment can be determined by monitoring bone mineral density (BMD) or biochemical markers in biological samples. Biochemical markers include, for example but not limited to, measuring the presence of estrogen in the blood of women, and calcium in the urine, hypercalciuria, or increased excretion of calcium. Other markers also include for example, but are not limited to serum markers of bone turnover, for example bone-specific alkaline phosphatase (BSAP), osteocalcin (BGP), tartrate-resistant acid phosphatase (TRAP) and urinary collagen C-terminal extension peptides (CrossLaps) (Hotchkiss et al, 2001; 29; 7-15). In some embodiments, diagnostic test for metabolic bone diseases and/or osteoporosis can be used, for example, as disclosed in European Patents EP1666883, EP1680513 and EP1639946, which are incorporated herein in their entirety by reference.

Some methods entail determining a baseline value of the bone density of a patient before administering a dosage of agent, and comparing this with a value for bone density of the patient after treatment. The same level of bone density or an increase in bone density indicates a positive treatment outcome (i.e., that administration of the agent has achieved or prevented a decrease in bone density loss). Alternatively, a decreased in the rate of bone density loss or of the rate of bone density loss also indicates a positive outcome, for example that administration has prevented or reduced the rate of the bone density loss. If the value for level of bone density decreases, a negative treatment outcome is indicated. In general, patients undergoing an initial course of treatment with an agent are expected to show the same level or an increase in bone density with successive dosages of an agent as described herein.

In other methods to determine efficacy of treatment, a control value (i.e., a mean and standard deviation) of bone density is determined for a control population. Typically the individuals in the control population have not received prior treatment and do not suffer from a metabolic bone disease or disorder, for example osteoporosis. Measured values of bone density in a patient after administering an inhibitor agent of Lp-PLA$_2$ as disclosed herein are then compared with the control value. An increase in the bone density in the patient relative to the control value (e.g. an increase of at least 10% of bone density and/or bone mass in a patient approaching control values signals a positive treatment outcome. A decrease in bone density decrease signals a negative treatment outcome.

In other methods, a control value of bone density is determined from a control population of patients who have undergone treatment with a therapeutic agent that is effective at halting the loss of bone density or increasing bone density. Measured values of bone density in the patient are compared with the control value.

In other methods, a patient who is not presently receiving treatment by agents that inhibit Lp-PLA$_2$ as disclosed herein, but has undergone a previous course of treatment is monitored for bone density to determine whether a resumption of treatment is required. The measured value of bone density in the test patient can be compared with a level of bone density previously achieved in the patient after a previous course of treatment. An increase in the rate of bone density loss and/or bone mass loss, or a decrease in bone density and/or bone mass relative to the previous measurement (e.g., a 10% increase of the rate of bone density loss and/or a decrease in bone density of about 10%) is an indication that treatment with an agent inhibitor of Lp-PLA$_2$ can be resumed. Alternatively, the level of bone density or bone mass in the patient can be compared with a control bone density level of determined in a population of patients after undergoing a course of treatment. Alternatively, the bone density in a patient can be compared with a control value in populations of prophylatically treated patients who remain free of symptoms of disease, in particular free of symptoms of metabolic bone diseases, for example osteoporosis or osteopenic related diseases, or populations of therapeutically treated patients who show amelioration of a disease symptom.

Methods to Identify Patients for Risk of, or having a Metabolic Bone Disease or Osteoporosis.

Patients amenable to treatment using the methods as disclosed herein include patients at risk of developing a metabolic bone disease or disorder such as osteoporosis but not showing symptoms, as well as patients showing symptoms of the metabolic bone disease patients with symptoms of osteoporosis.

Patients can be screened for their likelihood of having or developing osteoporosis based on a number of bone density tests, imaging tests, biochemical and genetic markers.

A number of diagnostic tests are available for identifying patients who have osteoporosis or osteopenic related diseases, or patients at risk of developing ostepoperosis or osteopenic diseases. These include, but are not limited to a bone density test, for example a dual energy x-ray absorption scan (also known as DEXA or DXA scan by persons of ordinary skill in the art). A DEXA scan can identify a patient with a normal bone density, low bone mass or osteoporosis. In some embodiments, bone density testing involves a low level of radiation exposure. For example, in some embodiments an non-isotopic detection method for osteoblastic activity can be used, as disclosed in U.S. Pat. No. 6,869,593 which is incorporated herein in its entirety by reference.

Other diagnostic tests to identify patients at risk of developing osteoporosis or osteopenic diseases include for example without limitation, X ray test to identify the presence of fractures or a history of fractures, bone mineral density (BMD) tests, for example BMD which can be used to determine bone health, bone scans, which identify a patient with metabolic bone disorders, for example cancer, bone lesions, abnormal bone marrow and new fractures. BMD tests provide a measurement known by persons in the art called a T-score, a number value that results from comparing the bone density to optimal bone density. When a T-score appears as a negative number such as −1, −2 or −2.5, the patient is identified as having low bone mass. The more negative the T-score, the greater risk the patient has of developing or having osteoporosis.

In some embodiments, diagnostic tests to identify patients at risk of developing osteoporosis or osteopenic diseases include for example without limitation, a three componet X-ray bone densitometry scan, as disclosed in U.S. Pat. No. 6,909,771 which is incorporated herein in its entirety by reference. One can also identify a patient at risk or having a metabolic bone disorder, for example osteoporosis, for example using a quantitative ultrasound (QUS) measurements, for example ultrasound bone analysis measurement as disclosed in U.S. Pat. No. 6,899,680 which is incorporated herein by reference.

Other diagnostic methods can be used to identify a patient at increased risk of developing osteoporosis or with osteoporosis, for example diagnositic methods as disclosed in European patents 1666883, 1680513 and 1639946, which are incorporated herein in their entirety by reference. Other methods to diagnose a patient at risk of or having a metabolic bone disease such as osteoporosis and/or abnormal bone marrow includes measurement of Lp-PLA$_2$ activity and/or expression using the methods as disclosed herein, for example using the PLAC test commercially available from diaDexus.

A number of biomarkers can identify a patient at risk of osteoporosis. For example, laboratory test are also useful in the methods of the present invention to identify a patient at risk of developing and/or having osteoporosis, for example measuring the levels of a number of biochemical markers in a biological sample including blood and/or urine. Such biochemical markers that can be measured include blood calcium levels, blood vitamin D levels, thyroid function, parathyroid hormone levels, estradiol levels to measure estrogen (useful in assessing the risk in women), follicle stimulating hormone (FSH) to establish menopause status, testosterone levels (in men) and osteocalcin levels to measure bone formation. One can perform clinical tests such as levels of calcium and phosphorus in blood for diagnosis of metabolic bone diseases or disorders, as about 20% of postmenopausal women with osteoporosis exhibit hypercalciuria, or increased excretion of calcium in urine. Other biochemical markers include for example, but are not limited to serum markers of bone turnover such as bone-specific alkaline phosphatase (BSAP), osteocalcin (BGP), tartrate-resistant acid phosphatase (TRAP) and urinary collagen C-terminal extension peptides (CrossLaps) (Hotchkiss et al, 2001; 29;7-15).

Such diagnostic tests are also useful to monitor response of the patient to administration of the Lp-PLA$_2$ inhibitor agents as disclosed herein. Accordingly, the dose and therapeutic regime of administration of the Lp-PLA$_2$ can be altered according for maximal benefit on improvement of a symptom of osteoporosis.

In some embodiments, a patient at risk of osteoporosis include women over 65 years of age, post-menopausal women under age 65 who have multiple risk factors, women at menopause, patients with abnormal spine x-rays, patients with long term oral steroid use and patients with hyperparathyroidism (an over active parathyroid gland).

Osteoporosis Risk Factors

One can also diagnose a patient with increased risk of developing a metabolic bone disease or disorder such as osteoporosis on the basis of risk factors. In some embodiments, patients identified to be at risk of metabolic bone diseases or disorders are administered agents that inhibit Lp-PLA$_2$ as disclosed herein. Risk factors for osteoporosis are known by persons of ordinary skill in the art, and include advanced age: (i) patients over the age of 65 years; and (ii) gender. Women are at greater risk than men as women lose bone more rapidly than men due to menopause—however, men are also at risk and constitute 20% of the patient population with osteoporosis; (iii) family and personal history, including a family history of osteoporosis, history of fracture on the mother's side of the family, and a personal history of any kind of bone fracture as an adult (after age 50); (iv) Race, with Caucasian and Asian women at increased risk; (v) body type, with patients who are small-boned, for example small boned women who weigh less than 127 pounds are at increased risk; (vi) menstrual history and menopause, with a normal menopause alone increasing a woman's risk of osteoporosis, and patients having an early menopause or cessation of menstruation before menopause increasing the risk of developing ostoporosis significantly; (vii) Hypogonadism (small gonads, e.g., testosterone deficiency) in males; (viii) lifestyle behaviors that increase osteoporosis risk include for example but are not limited to: calcium and/or vitamin D deficiency; little or no exercise, especially weight-bearing exercise; alcohol abuse; cigarette smoking; (ix) patients with chronic diseases and medications, for example certain types of medications can damage bone and lead to what is termed "secondary osteoporosis." This type of osteoporosis is estimated to occur in almost 50% of pre-menopausal women with osteoporosis and from 30% to 60% of men with osteoporosis. Also, secondary osteoporosis can cause further bone loss in postmenopausal women and older men with primary osteoporosis. Included in this category are certain medications to treat endocrine disorders such as hyperthyroidism, marrow disorders, collagen disorders, gastrointestinal problems and seizure disorders. Use of glucocorticoids (steroids) to treat diseases such as asthma, rheumatoid arthritis and inflammatory bowel disease, especially the oral form of these medications (at higher doses and over longer periods of time e.g., more than 2 months), can be particularly damaging to bone.

Other risk factors for osteopenic diseases and osteoporosis include, for example, patients with: a history of fractures as an adult, history of fractures in the first degree relative, advanced age, female patients, dementia, patients with poor health, fragility or both, current cigarette smoking, low body weight, anorexia nervosa, estrogen deficiency (past menopause, menopause before the age of 45, having both ovaries removed, or absence of menstrual periods for a year or more prior to menopause, low testosterone levels in men, use of certain medications such as cortiosteriods and anticonvulsants, lifelong low calcium intake, excessive alcohol intake, impaired eyesight despite adequate correction, recurrent falls and inadequate physical activity.

The cause of osteoporosis are include the hormone deficiency (estrogen or androgen), hormone excess (Cushing's syndrome or glucocorticoid administration, thyrotoxicosis, hyperparathyroidism, excessive vitamin D administration), immobilization, tobacco, malignancy, idiopathic or geriatric, and genetic disorders (Type I collagen mutations, Ehlers-danlos syndrome, Marfan's syndrome, Homocystinuria).

In some embodiments, inhibitors of Lp-PLA$_2$ can be administered to patients considered at especially high risk for developing osteoporosis, such patients include for example but without limitation: all women over age 65, women less than age 65 who are postmenopausal and have one or more of the above described risk factors for osteoporosis, postmenopausal women who experience any type of bone fracture, and men who have a testosterone deficiency.

In addition, one can also diagnose a patient with increased risk of developing a metabolic bone disease using genetic markers for the disease. Genetic markers to identify a patient at risk of developing the likes of osteoporosis are known to person of ordinary skill in the art. For example, polymorphisms or single nucleotide polymorphisms (SNPs) present in patients at risk for osteoporosis are disclosed in U.S. Pat. No. 6,825,336 which is specifically incorporated herein in its entirety by reference. Patients at risk of developing a metabolic bone disease or disorder such as osteoporosis have variances in the PPAR gamma gene, as disclosed in European Patent 1612279 which is incorporated herein in its entirety by reference.

Among the genetic disorders, osteogenesis imperfecta is caused by a major mutation in the gene encoding for type I collagen, the major collagen constituent of bone. This causes severe osteoporosis. Marfan's syndrome is caused by mutations in fibrillin gene on chromosome 15. Homocytinuria is caused by cystathionine beta-synthase deficiency and exhibits an autosomal recessive pattern of inheritance.

Researchers believe that genetic factors play a dominant role in the etiology of this disease among the ethnic or gender difference. Several genes have been shown to be associated with low bone density and research has focused on identifying those genes that may act as markers of disease. Common allelic variations of the vitamin D receptor gene have been found to be associated with decreased bone density in certain populations, including premenopausal women and young girls (Wood, R. J. and Fleet, J. C. Ann. Rev. Nutrit. 1998 18:233-258). Bone mineral density has also been associated with genetic variation in the estrogen receptor gene, both by itself and in conjunction with variations in the vitamin D receptor gene (Willing et al. J. Bone Min. Res. 1998 13:695-705). In Japanese women, the HLA-A*24-B*07-DRB*01 halotype has been linked to low peak bone mass (Tsuji et al. Hum. Immunol. 1998 59:243-249). A variant of the gene encoding transforming growth factor-beta 1 has also been associated with low bone mass in osteoporotic women and with low bone mass and increased bone turnover in normal women (Langdahl et al. Bone 1997 20:289-294). A polymorphism of the COLIAI gene has been identified as a potential marker for low bone mass and vertebral fracture in women (Grant et al. Nat. Genet. 1996 14:203-205). Devoto et al. (Eur. J. Hum. Genet. 1998 6:151-157) determined that there was a gene or genes on chromosome 1 of humans that was linked to low bone density. Polymorphisms linked to osteoporosis have been described in the TGF-91 gene, whose protein product is abundant in bone and an important regulator of bone resorption and formation (Langdahl et al., 1997; Yamada et al., 1998; WO97/28280 which is incorporated herein by reference). A polymorphism in the gene on chromosome 1 for tumor necrosis factor alpha receptor 2 has now been shown to be associated with low bone density. (Spotila et al. WO 0032826 which is incorporated herein by reference).

Genes associated with osteoporosis include, but not limit to: alcitonin receptor, collagen subunit (alpha-1 (X))3, Kuestner et al Mol. Pharmacol. 46 (2), 246-255 (1994); insulin-like growth factor binding protein 1, Brewer et al., Biochem. Biophys. Res. Commun. 152 (3), 1289-1297 (1988), Brinkman et al., EMBO J. 7 (8), 2417-2423 (1988), Cubbage et al., Mol. Endocrinol. 3 (5), 846-851 (1989), Alitalo et al., Hum. Genet. 83 (4), 335-338 (1989), Ekstand et al., Genomics 6 (3), 413-418 (1990), Suwanichkul et al., J. Biol. Chem. 265 (34), 21185-21193 (1990), Ehrenborg et al., Genomics 12 (3), 497-502 (1992); insulin-like growth factor 1 receptor beta chain, Francke et al., Cold Spring Harb. Symp. Quant. Biol. 51, 855-866 (1986), Ullrich et al., EMBO J. 5 (10), 2503-2512 (1986), Flier et al., Proc. Natl. Acad. Sci. U.S.A. 83 (3), 664-668 (1986), Abbott et al., J. Biol. Chem. 267 (15), 10759-10763 (1992), Werner et al., Proc. Natl. Acad. Sci. U.S.A. 93 (16), 8318-8323 (1996), Grant et al., J. Clin. Endocrinol. Metab. 83 (9), 3252-3257 (1998); interleukin 4 receptor, Idzerda et al., J. Exp. Med. 171 (3), 861-873 (1990), Pritchard et al., Genomics 10 (3), 801-806 (1991); Werner syndrome, Goto et al., Nature 355 (6362), 735-738 (1992).

Diagnosis of osteoporosis is most often done in conjunction with a study of bone density by radiography.

In asymptomatic patients, treatment can begin at any age (e.g., 10, 20, 30). Usually, however, it is not necessary to begin treatment until a patient reaches 40, 50, 60 or 70. Treatment typically entails multiple dosages over a period of time. In some embodiments, treatment with an inhibitor agent of Lp-PLA$_2$ can be monitored by assaying presence of biomarkers or density of bones as disclosed herein over time. If the bone density indicates low bone mass, additional treatment with agents inhibiting Lp-PLA$_2$ as disclosed herein are recommended, and/or treatment of additional therapies for metabolic bone disease, for example osteoporosis. In the case of potential patients with an inherited risk of developing osteoporosis, treatment can begin antenatally by administering therapeutic agent to the mother or shortly after birth.

Assessment of Inhibitors of Lp-PLA$_2$ in Models of Metabolic Bone Diseases and Osteoporosis and/or Osteopenia In some embodiments, agents inhibiting Lp-PLA$_2$ can be assessed in animal models for effect reducing a symptom of a metabolic bone disease. For example, one can use the porcine model of hyperglycemia and hypercholesterolemia (DM/HC) as disclosed herein, where the animal exhibits symptoms of a metabolic bone disease, for example reduced bone matrix and abnormal bone marrow, in which bone matrix and/or abnormal bone marrow can be assessed in the presence and absence of inhibitors for Lp-PLA$_2$ by methods commonly known by persons in the art. In some embodiments, bone density can be assessed using methods commonly known by persons of ordinary skill in the art, for example BMD tests or CT-micro assessment as disclosed in Example 1.

In some embodiments, agents inhibiting Lp-PLA$_2$ can be assessed in animal models for osteoporosis, permitting analysis of the effects of Lp-PLA$_2$ inhibitory agents on bone formation, bone repair and development and treatment, as well as assessment of drug dosages on the development, prognosis and recovery from metabolic bone diseases, for example osteoporosis. Animal models of osteoporosis are well known by person of ordinary skill in the art. One commonly well established model of postmenopausal bone loss are ovariectomized (OVX) rodents.

An effective dosage causes at least a measurable, statistically or clinically significant attenuation of at least one marker, symptom, or histological evidence characteristic of metabolic bone disorder and/or abnormal bone marrow. Markers, symptoms and histological evidence characteristic of osteoporosis include bone mass loss, decrease in bone density, and increase in blood calcium levels, and/or vitamin D levels, thyroid function, parathyroid hormone levels, estradiol levels to measure estrogen (useful in assessing the risk in women), follicle stimulating hormone (FSH) to establish menopause status, testosterone levels (in men) and osteocalcin levels to measure bone formation. Other biochemical markers also include calcium and phosphorus in blood, hypercalciuria, or increased excretion of calcium in urine, and presence of serum markers of bone turnover, for example bone-specific alkaline phosphatase (BSAP), osteocalcin (BGP), tartrate-resistant acid phosphatase (TRAP) and urinary collagen C-terminal extension peptides (CrossLaps) (Hotchkiss et al, 2001; 29;7-15).

Assessment of Inhibitors of Lp-$PLA_2$ on Models of Metabolic Bone Diseases or Disorders.

The suitability of an inhibitor of Lp-$PLA_2$ for the treatment of a metabolic bone disease can be assessed in any of a number of animal models for metabolic bone diseases. Animal models of osteoporosis are well known by person of ordinary skill in the art. For example, one commonly well established model of postmenopausal bone loss are ovariectomized (OVX) rodents, for example rat and mouse models and non-rodent animals, as disclosed in Thompson et al, 1995; 17:125 S-133S, Iwaniec et al, J. Bone Miner Res, 2006, 21;1086-74; Wimalawansa et al, Calcif Tissue Int, 2000; 66: 56-60 which demonstrate postmenopausal cancellous bone loss. Examples of OVX non-rodent anomals, include for example but are not limited to monkeys (Hotchkiss et al, Bone, 2001; 29:7-15) and sheep (Sigrist et al, J Bone Miner Metab, 2007; 28: 28-35. Other models of osteoporosis are known in the art, for example OVX non-primate animals, such as for example mice, rats, dogs, rabbits, pigs and sheep, as disclosed in Bellino, Menopause, 2000: 7; 14-24 and Thorndike and Turner, 1998, in search of an animal model for osteoporosis.

One can also use the porcine model of hyperglycemia and hypercholesterolemia (DM/HC) as disclosed herein, where the animal exhibits symptoms of reduced bone matrix and abnormal bone marrow in which bone matrix and/or abnormal bone marrow can be assessed in the presence and absence of inhibitors for Lp-$PLA_2$ by methods commonly known by persons in the art.

One can also use animal models for oral bone loss, for example animal models for metabolic peritonitis.

Animals administered the compounds are evaluated for symptoms relative to animals not administered the compounds. A measurable change in the severity of a symptom, (for example a decrease in at least one symptom) or a delay in the onset of a symptom in animals treated with an Lp-$PLA_2$ inhibitor versus untreated animals is indicative of therapeutic efficacy.

Formulations of Compositions

Compounds, for example agents inhibiting Lp-$PLA_2$ as disclosed herein, can be used as a medicament or used to formulate a pharmaceutical composition with one or more of the utilities disclosed herein. They can be administered in vitro to cells in culture, in vivo to cells in the body, or ex vivo to cells outside of an individual that can later be returned to the body of the same individual or another. Such cells can be disaggregated or provided as solid tissue.

Compounds, for example agents inhibiting Lp-$PLA_2$ as disclosed herein can be used to produce a medicament or other pharmaceutical compositions. Use of agents inhibiting Lp-$PLA_2$ which further comprise a pharmaceutically acceptable carrier and compositions which further comprise components useful for delivering the composition to an individual are known in the art. Addition of such carriers and other components to the agents as disclosed herein is well within the level of skill in this art.

Pharmaceutical compositions can be administered as a formulation adapted for delivery to the bone or direct contact with the bone marrow. In some embodiments, the compositions may be administered as a formulation adapted for systemic delivery. In some embodiments, the compositions may be administered as a formulation adapted for delivery to specific organs, for example but not limited to the liver, bone marrow or systemic delivery.

Alternatively, pharmaceutical compositions can be added to the culture medium of cells ex vivo. In addition to the active compound, such compositions can contain pharmaceutically-acceptable carriers and other ingredients known to facilitate administration and/or enhance uptake (e.g., saline, dimethyl sulfoxide, lipid, polymer, affinity-based cell specific-targeting systems). The composition can be incorporated in a gel, sponge, or other permeable matrix (e.g., formed as pellets or a disk) and placed in proximity to the endothelium for sustained, local release. The composition can be administered in a single dose or in multiple doses which are administered at different times.

Pharmaceutical compositions can be administered by any known route. By way of example, the composition can be administered by a mucosal, pulmonary, topical, or other localized or systemic route (e.g., enteral and parenteral). The phrases "parenteral administration" and "administered parenterally" as used herein means modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection, infusion and other injection or infusion techniques, without limitation. The phrases "systemic administration," "administered systemically", "peripheral administration" and "administered peripherally" as used herein mean the administration of the agents as disclosed herein such that it enters the animal's system and, thus, is patient to metabolism and other like processes, for example, subcutaneous administration.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject agents from one organ, or portion of the body, to another organ, or portion of the body. Each carrier must be "acceptable" in the sense of being compatible with the other ingredients of the formulation, for example the carrier does not decrease the impact of the agent on the treatment. In other words, a carrier is pharmaceutically inert.

Suitable choices in amounts and timing of doses, formulation, and routes of administration can be made with the goals of achieving a favorable response in the subject with a metabolic bone disease or disorder, such as osteoporosis or osteopenia or a risk thereof (i.e., efficacy), and avoiding undue toxicity or other harm thereto (i.e., safety). Therefore, "effective" refers to such choices that involve routine manipulation of conditions to achieve a desired effect.

A bolus of the formulation administered to an individual over a short time once a day is a convenient dosing schedule. Alternatively, the effective daily dose can be divided into multiple doses for purposes of administration, for example, two to twelve doses per day. Dosage levels of active ingredients in a pharmaceutical composition can also be varied so as to achieve a transient or sustained concentration of the compound or derivative thereof in an individual, especially in and around the bone or bone marrow, and to result in the desired therapeutic response or protection. But it is also within the skill of the art to start doses at levels lower than required to achieve the desired therapeutic effect and to gradually increase the dosage until the desired effect is achieved.

The amount of agents inhibiting Lp-PLA$_2$ administered is dependent upon factors known to a person skilled in the art such as bioactivity and bioavailability of the compound (e.g., half-life in the body, stability, and metabolism); chemical properties of the compound (e.g., molecular weight, hydrophobicity, and solubility); route and scheduling of administration, and the like. It will also be understood that the specific dose level to be achieved for any particular individual can depend on a variety of factors, including age, gender, health, medical history, weight, combination with one or more other drugs, and severity of disease.

In some embodiments, treatment can also involve combination with other existing modes of treatment, for example existing agents for treatment for osteoporosis, for example but not limited to, estrogens, bisphosphonates, calcitonin, flavonoids, and selective estrogen receptor modulators. Other approaches include peptides from the parathyroid hormone family, strontium ranelate, and growth hormone and insulin-like growth response.

U.S. Pat. No. 5,478,579, which is incorporated herein by reference, describes a method for inducing and enhancing the absorption of calcium into mammalian bone tissue in order to treat metabolic calcium deficiencies in bone tissue, in particular osteoporosis. In that reference, it was found that ossification of mammalian bone tissue could be enhanced by orally administering to a patient an effective dose of calcium in combination with a flavonol aglycone glycoside. It is believed that the flavonol aglycone glycoside affords an advantageous function through a chelation delivery system. Flavonols possess a benzene ring structure having available bonds to function as a chelate. Therefore, flavonols, due to their particular molecular structure, are capable of holding and delivering certain minerals, including calcium, to mammalian bone tissue. Also bone tissue would naturally absorb flavonol glycosides from the blood stream. It is further disclosed that the combination of the flavonol aglycone glycoside and calcium leads to an increased bone mineral density which would not have been obtainable through the use of simple calcium supplements.

Furthermore, quercetin, which is a related bioflavonoid and differs from the aforementioned flavonol compounds in that it does not contain the glycoside residue, has been shown to inhibit TNF-α induced expression of interleukin 8 (IL-8) and monocyte chemoattractant protein-1 (MCP-1) in cultured human synovial cells. It was therefore suggested that quercetin can be used in the treatment of rheumatoid arthritis which is an autoimmune disorder and involved synovial tissues of joints (Sato et al., The Journal of Rheumatology, 1997; 24:9, p. 1680). In addition, the relation between interleukins and cytokines and metabolic bone diseases was studied (Pumarino et al., Rev Med Chile 1996; 124: p. 48). It could be shown that interleukin 1, 6 and 11, transforming growth factor and tumor necrosis factor stimulate osteoclast mediated bone resorption. Interleukin 1 is the most potent bone resorption agent. Although the role of interleukin 1, 6, 11 and the tumor necrosis factors is not quite clear, they appear to have a depressing effect on bone formation.

Cohen et al. (Israel Journal of Medical Sciences, 17, 1981, p. 1123) investigated the cause of an increased crystallinity index in bone tissue found in iliac crest bone samples from postmenopausal osteoporotic women by chemical analysis. The percentage of crystallinity should be regarded as an index that assumes that mature bone is only apatitic and this provides a measure of crystal size and perfection. It could be demonstrated by Cohen et al. that osteoporotic women have low total body magnesium stores. It could also be shown that magnesium exerts its action as a crystal poison in the nucleation and growth of apatite and its precrystalline intermediate. Therefore, osteoporotic bone, i.e. bone mineral with a lower magnesium content, has larger and more perfect crystals and bone mineral with a higher magnesium content has smaller and less perfect crystals than normal bone mineral. It was consequently suggested that the administering of magnesium supplements may be used in osteoporosis therapy.

In some embodiments, agents that inhibit Lp-PLA$_2$ as disclosed herein can be combined with other therapeutic agent to prevent and/or treat metabolic bone disease or disorders. Such agents can be any agent currently in use or being developed for the treatment and/or prevention of osteoporosis, where the agent can have a prophylactic and/or a curative effect and/or reduce a symptom of a metabolic bone disorder or disease.

In embodiments where inhibitor agents of Lp-PLA$_2$ as disclosed herein are used for the prevention and/or treatment of osteoporosis, the inhibitor agents of Lp-PLA$_2$ as disclosed herein can be used in combination with medicaments commonly known by person of ordinary skill in the art that are claimed to be useful as symptomatic treatments of osteoporosis. Examples of such medicaments include, but are not limited to, agents known to modify or inhibit osteoclast activity, promote osteoblast activity and/or regulate cellular events necessary for healthy bone marrow and healthy bone metabolism.

In some embodiments, where the inhibitor agents of Lp-PLA$_2$ as disclosed herein are used for the treatment of osteoporosis, the inhibitor agents of Lp-PLA$_2$ as disclosed herein can be used in combination with those medicaments mentioned above that are claimed to be useful as symptomatic treatments of osteoporosis and/or disease-modifying agents. Disease modifying agents include, for example but are not limited to, estrogens, bisphosphonates, calcitonin, flavonoids, and selective estrogen receptor modulators. Other approaches include peptides from the parathyroid hormone family, strontium ranelate, and growth hormone and insulin-like growth response.

Bisphosphates, for example bisphosphate acid compounds includes for example, Alendronate, for example Fosmax, Ibandronate, for example Boniva and Risendronate, for example Actonel. Bisphosphphate acid compounds suppress excessive bone resorption in tumor-induced osteolysis, Paget's disease and osteoporosis, as disclosed in U.S. Pat. No. 6,555,529, and patents EP177433, EP337706, AU8551534, EP27982 and EP94714 which are incorporated herein in their entirety by reference. Bisphosphate acid compounds are alone disclosed in EP100718, U.S. Pat. Nos. 4,234,645 and 4,067,971 EP84822, WO/9203451, WO/935052, WO97/49711, WO97/04785 which are incorporated herein in their entirety by reference. In some embodiments, a bisphosphate acid compounds for use with the methods as disclosed herein includes bisphosphoric acid compounds for the treatment of bone marrow abnormalities, as disclose in U.S. Pat. No. 6,555,529 which is incorporated herein in its entirety by reference. In some embodiments, a pyridopyrimidine is useful with the methods as disclosed herein, for example as disclosed in International Application WO/03000011 which is incorporated herein in its entirety by reference.

Calcitonin includes Miacalcin, Calcimar and Fortical. Selective estrogen receptor modulators (SERM) can also be used for the treatment of osteoporosis, i.e. Roloxifene, sold as Evista®. Parathyroid hormone can also be used in combination with the agents that inhibit Lp-PLA$_2$ as disclosed herein. Teriparatide is one such agents. It is sold as Fortéo®. In some embodiments, estrogen replacement and/or hormone replacement therapy can be used in combination with agents that inhibit Lp-PLA$_2$ formation as disclosed herein. In some embodiments, an increase in calcium and/or vitamin D, and/or an increase in physical activity and/or increase in healthy lifestyle (for example stopping smoking, avoidance of excessive alcohol) can be combined with the methods as disclosed herein. One can also use indole derivatives with the agents as disclosed herein for the treatment and/or prevention of metabolic bone disorders as disclosed in U.S. Pat. No. 6,903,117 which is incorporated in its entirety herein by reference. One can further also use proton pump inhibitors with the agents as disclosed herein for the treatment and/or prevention of metabolic bone disorders, for example osteoporosis, for example as disclosed in International Patent Application WO01/44257 which is incorporated in its entirety herein by reference. One can further also use quinolones with the agents as disclosed herein for the treatment and/or prevention of metabolic bone disorders as disclosed in U.S. Patent Application 2003/0114486 which is incorporated in its entirety herein by reference.

In some embodiments, where the metabolic bone disorder or disease is a bone marrow neoplasm, agent useful for administration to the patient in combination with the agents that inhibit Lp-PLA$_2$ as disclosed herein are cancer agents admininstered for surgery, chemotherapy, radiotherapy, hormone therapy and immunotherapy and the like. Such agents include chemotherapeutic agents covering three main categories of therapeutic agent: (1) other antiangiogenic agents that work by different mechanisms from those defined hereinbefore (linomide, angiostatin, razoxin, thalidomide), (ii) cytostatic agents such as antioestrogens (tamoxifen, toremifene, raloxifene, droloxifene, iodoxyfene), progestogens (megestrol acetate), aromatase inhibitors (nastrozole, letrazole, vorazole, exemestane), antiprogestogens, antiandrogens (flutamide, nilutamide, bicalutamide, cyproterone acetate), LHRH agonists and antagonists (goserelin acetate, luprolide), inhibitors of testosterone 5.alpha.-dihydroreductase (finasteride), anti-invasion agents (metalloproteinase inhibitors like marimastat and inhibitors of urokinase plasminogen activator receptor function) and inhibitors of growth factor function, (such growth factors include for example EGF, FGFs, platelet derived growth factor and hepatocyte growth factor such inhibitors include growth factor antibodies, growth factor receptor antibodies, tyrosine kinase inhibitors and serine/threonine kinase inhibitors); and (iii) antiproliferative/antineoplastic drugs and combinations thereof, as used in medical oncology, such as antimetabolites (for example antifolates like methotrexate, fluoropyrimidines like 5-fluorouracil, purine and adenosine analogues, cytosine arabinoside); antitumour antibiotics (for example anthracyclines like doxorubicin, daunomycin, epirubicin and idarubicin, mitomycin-C, dactinomycin, mithramycin); platinum derivatives (cisplatin, carboplatin); alkylating agents (nitrogen mustard, melphalan, chlorambucil, busulphan, cyclophosphamide, ifosfamide, nitrosoureas, thiotepa); antimitotic agents (vinca alkaloids like vincristine and taxoids like taxol, taxotere); topoisomerase inhibitors (for example epipodophyllotoxins like etoposide and teniposide, amsacrine, topotecan), which are useful in the methods as disclosed herein.

Thus, combination treatment with one or more agents that inhibit Lp-PLA$_2$ with one or more other medical procedures can be practiced.

In addition to administering an␣p-PLA2 inhibitor, one can also administer one or more other therapeutic agent which prevents or reduces bone demineralization, or effects re-mineralization. Examples are bisphosphonates, parathyroid hormone (PTH), hormone replacement therapy (HRT), selective estrogen receptor modulators (SERM), calcitonin, RANKL antibody, constitutively active androstane receptor (CaR) antagonist and cathepsin K inhibitors.

Examples of bisphosphonates include, for example but are not limited to Alendronate (Fosamax®—Merck), Risedronate (Actonel®—Proctor & Gamble), Ibandronate (Boniva®/Bonviva®—Roche/GSK/), Zoledronate (Reclast®/Aclasts®—Novartis). Examples of PTH drugs include teriparatide (Forteo®/Forsteo®—Eli Lilly) parathyroid hormone. Hormone replacement therapy and/or selective estrogen receptor modulators include estrogen, Premarin® being one example, raloxifene sold under the name Evista® by Eli Lilly, and bazedoxifene under development by Wyeth. An example of a calcitonin therapy is Miacaclin® sold by Novartis.

One or more of these drugs, and drugs of these types, can be administered at the same time as the Lp-PLA2 inhibitor, or they may be administered at another time if the affects of the combination therapy is optimized by the latter regime. While it is believed that the dosage of these second therapeutics will most likely be those approved for use as a stand-alone therapy, it is possible that a particular combination may warrant adjusting the dosage up or down depending on factors such as drug/drug effects and/or the need or response of a particular patient.

In addition, treatment can also comprise multiple agents to inhibit Lp-PLA$_2$ expression or activity. Other agents include the use of statins with Niacin (see world-wide web site; genengnews-dot-com/news/bnitem.aspx?name=6724568) and fenofibrate (see world-wide web site; genengnews-dot-com/news/bnitem.aspx?name=14817756&taxid=19).

Similarly, diagnosis according to the invention can be practiced with other diagnostic procedures. The bone marrow or blood or urine can be assayed for a change in gene expression profiles using disease-specific molecular diagnostics kits (e.g., custom made arrays, multiplex QPCR, multiplex proteomic arrays). In addition, a non-invasive diagnostic procedure (e.g., CAT, MRI, SPECT, or PET) can be used in combination to improve the accuracy and/or sensitivity of diagnosis. Early and reliable diagnosis is especially useful to for prevention and/or treatment for metabolic bone disorders as disclosed herein.

The amount which is administered to a patient is preferably an amount that does not induce toxic effects which outweigh the advantages which result from its administration. Further objectives are to reduce in number, diminish in severity, and/or otherwise relieve suffering from the symptoms of the disease in the individual in comparison to recognized standards of care.

Dosages, formulations, dosage volumes, regimens, and methods for analyzing results aimed at inhibiting Lp-PLA$_2$ expression and/or activity can vary. Thus, minimum and maximum effective dosages vary depending on the method of administration. Suppression of the clinical and histological changes associated with a metabolic bone disease and/or disorder can occur within a specific dosage range, which, however, varies depending on the organism receiving the dosage, the route of administration, whether agents that inhibit Lp-PLA$_2$ are administered in conjunction with other co-stimulatory molecules, and the specific regimen of inhibitor of Lp-PLA$_2$ administration.

For oral or enteral formulations for use with the present invention, tablets can be formulated in accordance with conventional procedures employing solid carriers well-known in the art. Capsules employed for oral formulations to be used with the methods of the present invention can be made from any pharmaceutically acceptable material, such as gelatin or cellulose derivatives. Sustained release oral delivery systems and/or enteric coatings for orally administered dosage forms are also contemplated, such as those described in U.S. Pat. No. 4,704,295, "Enteric Film-Coating Compositions," issued Nov. 3, 1987; U.S. Pat. No. 4,556,552, "Enteric Film-Coating Compositions," issued Dec. 3, 1985; U.S. Pat. No. 4,309,404, "Sustained Release Pharmaceutical Compositions," issued Jan. 5, 1982; and U.S. Pat. No. 4,309,406, "Sustained Release Pharmaceutical Compositions," issued Jan. 5, 1982 which are incorporated herein in their entirety by reference.

Examples of solid carriers include starch, sugar, bentonite, silica, and other commonly used carriers. Further non-limiting examples of carriers and diluents which can be used in the formulations of the present invention include saline, syrup, dextrose, and water.

Enteric Coated Formulation

As regards formulations for administering the small chemical entities for inhibitors of Lp-PLA$_2$ of the likes of formulas (I)-(IV) as disclosed herein, one particularly useful embodiment is a tablet formulation comprising the Lp-PLA inhibitor with an enteric polymer casing. An example of such a preparation can be found in WO2005/021002 which is incorporated herein in its entirety by reference. The active material in the core can be present in a micronised or solubilised form. In addition to active materials the core can contain additives conventional to the art of compressed tablets. Appropriate additives in such a tablet can comprise diluents such as anhydrous lactose, lactose monohydrate, calcium carbonate, magnesium carbonate, dicalcium phosphate or mixtures thereof; binders such as microcrystalline cellulose, hydroxypropylmethylcellulose, hydroxypropyl-cellulose, polyvinylpyrrolidone, pre-gelatinised starch or gum acacia or mixtures thereof; disintegrants such as microcrystalline cellulose (fulfilling both binder and disintegrant functions) cross-linked polyvinylpyrrolidone, sodium starch glycollate, croscarmellose sodium or mixtures thereof; lubricants, such as magnesium stearate or stearic acid, glidants or flow aids, such as colloidal silica, talc or starch, and stabilisers such as desiccating amorphous silica, colouring agents, flavours etc. Preferably the tablet comprises lactose as diluent. When a binder is present, it is preferably hydroxypropylmethyl cellulose. Preferably, the tablet comprises magnesium stearate as lubricant. Preferably the tablet comprises croscarmellose sodium as disintegrant. Preferably, the tablet comprises microcrystalline cellulose.

The diluent can be present in a range of 10-80% by weight of the core. The lubricant can be present in a range of 0.25-2% by weight of the core. The disintegrant can be present in a range of 1-10% by weight of the core. Microcrystalline cellulose, if present, can be present in a range of 10-80% by weight of the core.

The active ingredient preferably comprises between 10 and 50% of the weight of the core, more preferably between 15 and 35% of the weight of the core. (calculated as free base equivalent). The core can contain any therapeutically suitable dosage level of the active ingredient, but preferably contains up to 150 mg as free base of the active ingredient. Particularly preferably, the core contains 20, 30, 40, 50, 60, 80 or 100 mg as free base of the active ingredient. The active ingredient can be present as the free base, or as any pharmaceutically acceptable salt. If the active ingredient is present as a salt, the weight is adjusted such that the tablet contains the desired amount of active ingredient, calculated as free base of the salt. Preferably, the active ingredient is present as a hydrochloride salt.

The core can be made from a compacted mixture of its components. The components can be directly compressed, or can be granulated before compression. Such granules can be formed by a conventional granulating process as known in the art. In an alternative embodiment, the granules can be individually coated with an enteric casing, and then enclosed in a standard capsule casing.

The core is surrounded by a casing which comprises an enteric polymer. Examples of enteric polymers are cellulose acetate phthalate, cellulose acetate succinate, methylcellulose phthalate, ethylhydroxycellulose phthalate, polyvinylacetate pthalate, polyvinylbutyrate acetate, vinyl acetate-maleic anhydride copolymer, styrene-maleic mono-ester copolymer, methyl acrylate-methacrylic acid copolymer or methacrylate-methacrylic acid-octyl acrylate copolymer. These can be used either alone or in combination, or together with other polymers than those mentioned above. The casing can also include insoluble substances which are neither decomposed nor solubilised in living bodies, such as alkyl cellulose derivatives such as ethyl cellulose, crosslinked polymers such as styrene-divinylbenzene copolymer, polysaccharides having hydroxyl groups such as dextran, cellulose derivatives which are treated with bifunctional crosslinking agents such as epichlorohydrin, dichlorohydrin or 1,2-, 3,4-diepoxybutane. The casing can also include starch and/or dextrin.

Preferred enteric coating materials are the commercially available Eudragit® enteric polymers such as Eudragit® L, Eudragit® S and Eudragit® NE used alone or with a plasticiser. Such coatings are normally applied using a liquid medium, and the nature of the plasticiser depends upon whether the medium is aqueous or non-aqueous. Plasticisers for use with aqueous medium include propylene glycol, triethyl citrate, acetyl triethyl citrate or Citroflex® or Citroflex® A2. Non-aqueous plasticisers include these, and also diethyl and dibutyl phthalate and dibutyl sebacate. A preferred plasticiser is Triethyl citrate. The quantity of plasticiser included will be apparent to those skilled in the art.

The casing can also include an anti-tack agent such as talc, silica or glyceryl monostearate. Preferably the anti-tack agent is glyceryl monostearate. Typically, the casing can include around 5-25 wt % Plasticiser and up to around 50 wt % of anti tack agent, preferably 1-10 wt. % of anti-tack agent.

If desired, a surfactant can be included to aid with forming an aqueous suspension of the polymer. Many examples of possible surfactants are known to the person skilled in the art. Preferred examples of surfactants are polysorbate 80, polysorbate 20, or sodium lauryl sulphate. If present, a surfactant can form 0.1-10% of the casing, preferably 0.2-5% and particularly preferably 0.5-2%

In one embodiment, there is a seal coat included between the core and the enteric coating. A seal coat is a coating material which can be used to protect the enteric casing from possible chemical attack by any alkaline ingredients in the core. The seal coat can also provide a smoother surface, thereby allowing easier attachment of the enteric casing. A person skilled in the art would be aware of suitable coatings.

Preferably the seal coat is made of an Opadry coating, and particularly preferably it is Opadry White OY-S-28876.

In one embodiment, the pharmaceutically active ingredient is 1-(N-(2-(diethylamino)ethyl)-N-(4-(4-trifluoromethylphenyl)benzyl)aminocarbonylmethyl)-2-(4-fluorobenzyl) thio-5,6-trimethylenepyrimidin-4-one, or a salt thereof.

One example of such an enteric-coated formulation, as described in WO2005/021002, comprises varying amounts of 1-(N-(2-(diethylamino)ethyl)-N-(4-(4-trifluoromethylphenyl)benzyl)aminocarbonylmethyl)-2-(4-fluorobenzyl)thio-5,6-trimethylenepyrimidin-4-one (called "active" in this example) as hydrochloride salt.

In that example, lactose monohydrate, microcrystalline cellulose, the active ingredient, the hydroxypropyl methyl cellulose and half of the croscarmellose sodium were screened into a 10 Litre Fielder high-shear blender (any suitable high shear blender could be used) and blended for 5 minutes at 300 rpm with the chopper off. The mixture was then granulated by the addition of about 750 ml water whilst continuing to blend. The granules were dried in a Glatt 3/5 fluid bed drier, screened by Comil into a Pharmatec 5 Litre bin blender and then blended with any lactose anhydrous given in the formula plus the remainder of the croscarmellose sodium over 5 minutes at 20 rpm. Magnesium stearate was screened into the blender and the mixing process continued for a further 1 minute at 10 rpm. The lubricated mix was compressed using a Riva Piccolla rotary tablet press fitted with 9.5 mm round normal convex punches (any suitable tablet press could be used). The sealcoat, and subsequently the enteric coat, are applied by spraying of an aqueous suspension of the coat ingredients in a Manesty 10 coater using parameters for the coating process as recommended by the manufacturers of the coating polymers (again, any suitable coater could be used).

Other enteric-coated preparations of this sort can be prepared by one skilled in the art, using these materials or their equivalents.

EXAMPLES

The examples presented herein relate to the methods and compostions for the prevention and/or treatment of metabolic diseases or disorders including but not limited to osteoporosis or osteopenia. Throughout this application, various publications are referenced. The disclosures of all of the publications and those references cited within those publications in their entireties are hereby incorporated by reference into this application in order to more fully describe the state of the art to which this invention pertains. The following examples are not intended to limit the scope of the claims to the invention, but are rather intended to be exemplary of certain embodiments. Any variations in the exemplified methods which occur to the skilled artisan are intended to fall within the scope of the present invention.

Methods

Animal model: A diabetic/diabetic hypercholestrolemic pig model (DM/HC) was developed that mimics human-like atherosclerosis. Domestic Yorkshire boars weighing 25-30 kg and aged ~4 months were castrated and made diabetic with a single intravenous injection of 125 mg/kg of streptozotocin (Sicor Pharmaceuticals, Irvine, Calif.). After stabilized for 1-2 weeks, the animals with elevated levels of plasma glucose (>150 mg/dl) were fed with atherogenic (high-fat) diet as shown in Table 1 (Animal Specialties, Quakertown, Pa.) to achieve a cholesterol level of approximately 250-800 mg/dl. Maintainance of the cholesterol level was determined by method as shown in Table 2.

TABLE 1

Diet for 2.0% cholesterol diet the components are:

| Component | Weight/Weight % |
|---|---|
| Purina* porcine grower meal | 47.5% |
| Lard | 25.0% |
| Casein | 11.1% |
| Dried whole milk | 7.9% |
| Peanut oil | 2.37% |
| Cholesterol | 2.0% |
| Wesson salt mix | 2.37% |
| Purina* vitamin mix | 1.58% |
| Sodium cholate | 1.58% |
| Calcium carbonate | 0.4% |
| Choline chloride | 0.2% |

*Purina Mills, LLC, Checkerboard Square, St. Louis, Missouri, 63164, USA. These feeds were prepared by Animal Specialties and Provisions, LLC, Quakertown, PA USA.

For the 0.5% cholesterol diet the components are similar with the exception of 0.5% cholesterol and 20% lard. The animals were Yorkshire pigs that were castrated males at the age of 3-5 and were obtained from Archer Farms, Darlington, Md. These feeds were prepared by Animal Specialties and Provisions, LLC, Quakertown, Pa. USA.

On days 1-2, animals were fed normal chow, followed by on days 3-14 animals were fed a diet of 0.5% cholesterol, 2% lard and on day 14, cholesterol levels were measured and the diet adjusted accordingly to increase to 2% cholesterol, 10% lard if cholesterol is <300 mg/dl. Following induction of DM/HC, cholesterol was measured until cholesterol levels are stable between 300 and 800 mg/dl, and following cholesterol stabilization, cholesterol was measured monthly. If cholesterol levels were unstable following initial stabilization phase, the diet of the animal was returned to the initial two-week measurement schedule. Monthly cholesterol levels were determined, including levels of total cholesterol, LDL, HDL, VLDL and triglycerides. Adjustment of the diet of the animal for a stable cholersteol level was determined according to the outlines shown in Table 2.

TABLE 2

Cholesterol and Dietry adjustment.

| Cholesterol level | Dietary adjustment | Next measurement | Cholesterol level | Dietary adjustment | Next cholesterol measurement |
|---|---|---|---|---|---|
| <250 mg/dl | Change to 25% lard diet. | 2 weeks | <300 mg/dl | Continue 25% lard diet | 2 weeks |
|  |  |  | 300-800 mg/dl | Change to 75% lard (25% lard): 25% normal diet | 2 weeks |
|  |  |  | >800 mg/dl | Change to 100% 10% lard diet | 2 weeks |
|  |  |  | >1000 mg/dl | Change to 50:50 mix of 10% lard diet | 2 weeks |
|  |  |  | >1500 mg/dl | Change to normal diet | 2 weeks* |

TABLE 2-continued

Cholesterol and Dietry adjustment.

| Cholesterol level | Dietary adjustment | Next measurement | Cholesterol level | Dietary adjustment | Next cholesterol measurement |
|---|---|---|---|---|---|
| 300-800 mg/dl | No change. 10% lard diet | 2 weeks | <300 mg/dl | Change to 25% lard diet | 2 weeks |
| | | | 300-800 mg/dl | No change | Regular schedule |
| | | | >800 mg/dl | Change to 50:50 mixture with 10% lard | 2 weeks |
| | | | >1000 mg/dl | Change to 25:75 mixture with 10% lard | 2 weeks |
| | | | >1500 mg/dl | Normal chow | 2 weeks |
| 800-1000 mg/dl | Change to 50:50 mix of 10% lard and normal chow diet. | 2 weeks | <300 mg/dl | Change to 25:75 mixture with 10% lard diet | 2 weeks |
| | | | 300-800 mg/dl | No change in diet (50:50) 10% lard | 2 weeks |
| | | | >800 mg/dl | Change to 25:75 mixture (10% lard) | 2 weeks |
| | | | >1000 mg/dl | Change to 25:75 mixture (10% lard) | 2 weeks |
| | | | >1500 mg/dl | Normal chow | 2 weeks* |
| >1000 mg/dl | 25:75 mix of 10% lard and normal chow diet. | 2 weeks | <300 mg/dl | Change to 50:50 mix of 10% lard and normal chow diet. | 2 weeks |
| | | | 300-800 mg/dl | No change in diet 25:75 mix of 10% lard and normal chow diet | 2 weeks |
| | | | >800 mg/dl | No change in diet | 2 weeks |
| | | | >1000 mg/dl | Normal chow | 2 weeks* |
| | | | >1500 mg/dl | Normal chow | 2 weeks* |
| >1500 mg/dl | Normal chow diet. | 2 weeks | <300 mg/dl | Change to 100% of 10% lard diet. | 2 weeks |
| | | | 300-800 mg/dl | Change diet to 50:50 mix of 10% lard and normal chow diet | 2 weeks |
| | | | >800 mg/dl | Normal chow | 2 weeks* |
| | | | >1000 mg/dl | Normal chow | 2 weeks* |
| | | | >1500 mg/dl | Normal chow | 2 weeks* |

At one month after stabilization of choleresterol at 250-800 mg/dl, the animals were randomized into two experimental groups, DM/HC (hyperglycemia and hypercholesterolemia) group with no treatment and treatment group (10 mg/kg/day of SB-480848, also referred to as 1-(N-(2-(diethylamino)ethyl)-N-(4-(4-trifluoromethylphenyl)benzyl)-aminocarbonylmethyl)-2-(4-fluorobenzyl)thio-5,6-trimethylenepyrimidin-4-one). The animals were sacrificed at 6-month after the randomization. The animal protocol has been approved by the Institutional Animal Care and Use Committee of University of Pennsylvania.

Two diabetic/hypercholesterolemic groups were evaluated: 1. DM/HC group and 2. DM/HC animals receiving Lp-PLA$_2$ inhibitors. The experiments included: the control group (DM/HC group—17 pigs) and the experimental group (DM/HC animals receiving Lp-PLA$_2$ inhibitors—20 pigs). In addition blood cholesterol levels were maintained between 300 and 800 mg/dl in experimental animals, this range having been determined to provide a better test model. Blood cholesterol levels were monitored in all animals on a bimonthly basis, as shown in Table 4 and adjustments were made to the fat content of the feed accordingly, as shown in Table 2. The cholesterol and lard percent were in the range of 0.5-2% and 10-25%, respectively, and all animals received feed that contained cholesterol and lard concentration within that range. Blood samples were obtained at baseline, 1 month, 3 months, and 6 months. Less than 1 ml/kg of blood were obtained each time. At the bimonthly blood cholesterol levels tests, levels of total cholesterol, LDL, HDL, VLDL and triglycerides, blood glucose, Lp-PLA$_2$ and primary bone marrow cells (PBMCs) were tested (see Table 4).

The animal number, selected to justify the minimum requirement for statistical validity were 2 groups of animals per experiment as follows: 1. Control group (n=17); Diabetic and hyperlipidemic; 2. Experimental group (n=20) Diabetic, hyperlipidemic receiving 10 mg/kg Lp-PLA$_2$ inhibitor, as shown in Table 3.

Domestic farm pigs, Yorkshire boars, ranging in weight between 25-35 kg were purchased from a local farm and placed in indoor housing under the care of a veterinarian. They were castrated 3-5 days in advance of the study start date. Test pigs were made diabetic by infusing one dose of streptozocin (125 mg/kg) IV in a period of 30 min. If animals do not become diabetic a second dose of (50 mg/kg) was administered. To avoid the possible onset of initial hypoglycemia, 20 g of glucose powder was added to the feed for the first 2. The blood glucose was measured using a glucometer every day before feeding for the first 14 days and then once a week.

Test animals were housed separately from control animals to avoid inter-animal transfer of drug due to colcophagia. All animals were fed an atherogenic diet twice daily with free access to water. The custom-made diet contained 0.5 and 2% cholesterol and 10 and 25% lard, the components of which are shown in Table 1.

TABLE 3

Schedule of animals and procedures (divided into 2 groups):

| | Animal number | Timeline |
|---|---|---|
| Group 1: DM/HC | N = 17 | 7 months |
| Group 2: DM/HC receiving Lp-PLA$_2$ inhibitors | N = 20 | 7 months |
| Total | N = 37 | 7 months |

TABLE 4

| Summary of Proceedures | | | | | | | | |
|---|---|---|---|---|---|---|---|---|
| | Start | 28 d | 57 d | 85 d | 113 d | 141 d | 168 d | 196 d |
| Serum Glucose, LDL, HDL, Triglycerides | X | X | X | X | X | X | X | X |
| Lp-PLA$_2$ (frozen serum-EDTA) | X | X | X | X | X | X | X | X |
| PBMCs | X | | X | | X | | | X |
| Tissue harvest | | | | | | | | X |

Daily dosing began on Day 29, at which time each test animal was given a daily dose of 10 mg/kg SB-480848 (given as bolus equivalent in dog food). Animals were NPO from midnight the night before. Animals were euthanized on Day 196 and tissues harvested immediately.

Histochemical Stains. Tissues were fixed in 4% Paraformaldehyde, decalcified in 12.5% EDTA, dehydrated in a graded series of ethanol, followed by xylene, embedded in paraffin and sectioned (6 mm). Paraffin sections were dewaxed, rehydrated and stained with Harris Hematoxylin (Fisher Scientific, Kalamazoo, Mich.; 245-678) alcian blue (Alcian Blue 8GX, Sigma, St. Louis, Mo.; A3157) (pH 1) and Eosin Y (Fisher Scientific Kalamazoo, Mich.; 245-827) (H&E-AB) to determine cellularity, vascularization, tissue morphology and proteoglycan content. Inflammatory cells were identified via staining with Protocol Wrights-Giemsa Stain (Fisher Scientific, Kalamazoo, Mich.; 264-985).

TUNEL Assay. Apoptosis was measured by the TUNEL assay. The TUNEL assay takes advantage of the fact that during apoptosis nuclear endonucleases digest genomic DNA into fragments of multiples of approximately 200 bp. To measure the fragmented DNA, the nucleotide ends were labeled using the FragEL DNA Fragmentation Kit Colorimetric—Klenow Enzyme (Calbiochem, EMD Biosciences, La Jolla, Calif., Q1A21-1EA) according to manufacturer's instructions and positive DAB signal was visualized by microscopy as described below. DNase I recombinant, grade I (Roche Diagnostics, Indianapolis, Ind.; 04 536 282 001) was used to generate TUNEL positive control sections according to manufacturer's instructions. Counterstained with Methyl Green. Analysis was performed on 4 animals from each group, and representative images taken.

Image Acquisition, Capture, and Analysis. Images were acquired with a Retiga EXi digital-cooled CCD camera with RGB electronic filter (QImaging, Canada) or with an with an RT Color Spot 1× HRD 100-NIK Model 2.2.1 camera (Diagnostic Instruments, Sterling Heights, Mich.) on either a Nikon Optiphot or on a Nikon E800 (Nikon, Melville, N.Y.) both equipped with z-axis motors (Prior Scientific, Rockland, Mass.).

Alkaline Phosphatase and Alizarin Red Staining. Alizarin Red and Alkaline Phosphatase Staining are bone marker proteins indicating the degree of mineralization and intensity of osteoblast differentiation, respectively. MLO-A5 osteoblastic cells (isolated from 14-day-old osteocalcin promoter-driven T-antigen transgenic mice, J Bone Miner Res 12:2014-2023, 1997) were cultured on Collagen1 coated plates at density 15000 cells/well in 12-well TC plates. After 24 hours, the cells were treated w/10 mM β-GP and LysoPC at 5 µM concentration for 3 and 7 days. Treatment was repeated every other day. At each time point alizarin red and alkaline phosphatase staining was performed. Alkaline phosphatase Detection Kit (Chemicon, Intl., Temecula, Calif., SCR004) was used for detection and performed as per manufactures instructions. To visualize mineralization the cells were washed once with a 2% Alizarin Red S solution for 5-10 min. at room temperature followed by one wash with water, two washes with PBS and fixation with paraformaldehyde. The results were then imaged with a digital cooled CCD camera.

Cell Proliferation. MLO-A5 cells were plated in 48-well TC dishes at a density of 5,000 cells/well and allowed to attach (5-6 hrs.). The cells were treated with 5 uM of Lyso PC for 18 hrs followed by analysis with the CyQUANT Cell Proliferation Assay Kit (Molecular Probes) following manufacturers instructions to measure MLO-A5 proliferation.

EXAMPLE 1

Bone Density and Micro-Architecture is Increased by Inhibitors of Lp-PLA$_2$

Tissue sampling: The right knee joint was removed and dissected. The femoral bone was split in half in parallel to the long axis of the bone. A piece of bone including both the articular surface and growth plate region (~15-20 mm) was sliced off from the front and parallel to the femoral shaft (FIG. 1). The tissues were fixed in 4% paraformaldehyde and scanned within one week in a µCT scanner (µCT-40, Scanco Corp.) with a voxel resolution of 20 µm.

MicroCT Analysis—Micro CT analysis generates 3 dimensional data including bone density and indices of micro-architecture. From the central region, i.e., between the articular surface (top) and the growth plate (bottom), 250 slices (~5 mm$^2$) were analyzed. To avoid artifact, the measurements were contoured away from the regions directly below the articular surface and the cutting edges. Paraformaldehyde fixed tissues (2×2 cm) were analyzed using microCT 40 (Scanco Medical, Bassersdorf, Switzerland) and a 3D reconstruction of the images slices was generated. The tissues were scanned at a medium resolution with slice thickness and slice increments of 20 µm. A Sigma filter setting of 0.8, a support value of 1, and a threshold setting of 195. Scanning was performed at an energy setting of 70000 (V) and an intensity of 114 (µA) with an integration time of 200 ms. All values for tissue volume (mm3), bone volume (mm3), bone volume/tissue volume, and mean/density (mg HA/ccm) were also calculated and recorded. The raw data were automatically segmented and analyzed with the µCT Evaluation Program; the segmented data were imported and displayed in µCT Ray V3.0. The image density was measured with the Distance3D tool of the µCT Evaluation Program V5.0.

The results of the MicroCT are summarized in Table 5 and examples of DM/HC-induced oestoporic changes are shown in FIG. 2.

TABLE 5

| Results from MicroCT analysis. | | | | |
|---|---|---|---|---|
| Measurements | Control | DM/HC | SB480848 | P value |
| SMI | 0.68 ± 0.10 | 0.997 ± 0.11 | 0.65 ± 0.10 | 0.028 |
| BV/TV | 0.25 ± 0.01 | 0.21 ± 0.01 | 0.25 ± 0.01 | 0.016 |
| BS/BV | 23.18 ± 1.55 | 27.16 ± 0.81 | 24.40 ± 0.51 | 0.012 |
| Tb · Th | 0.10 ± 0.007 | 0.09 ± 0.003 | 0.10 ± 0.002 | 0.051 |

TABLE 5-continued

Results from MicroCT analysis.

| Measurements | Control | DM/HC | SB480848 | P value |
|---|---|---|---|---|
| Tb · Sp | 0.36 ± 0.018 | 0.36 ± 0.02 | 0.33 ± 0.007 | 0.184 |
| Tb · N | 2.56 ± 0.12 | 2.66 ± 0.12 | 2.78 ± 0.06 | 0.396 |
| Conn-Dens | 31.38 ± 3.46 | 34.97 ± 2.74 | 35.69 ± 1.22 | 0.828 |

(P-value is t-test DM/HC vs. SB480848)

Figure 2C:
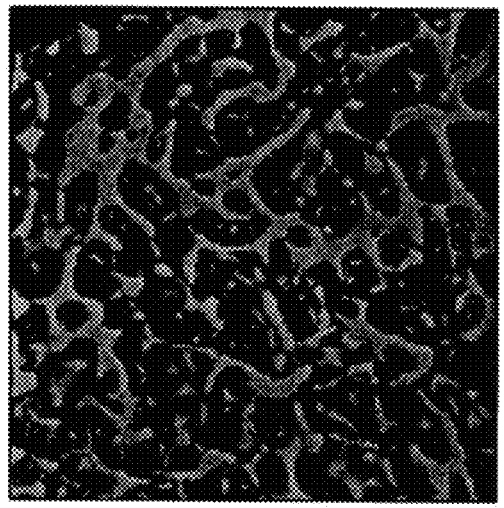
FIG. 2 shows examples of diabetes mellitus/hypercholesteremia (DM/HC)-induced osteoporotic changes and the effects of the treatment in trabecular bone. Panel 2A shown bone matrix density on non-treated non-DM/HC control animals, and panel
FIG. 2B shows an example from a DM/HC non-treated animals as compared to panel FIG. 2C showing DM/HC animals treated with an inhibitor of Lp-PLA$_2$.
Figure 2B:
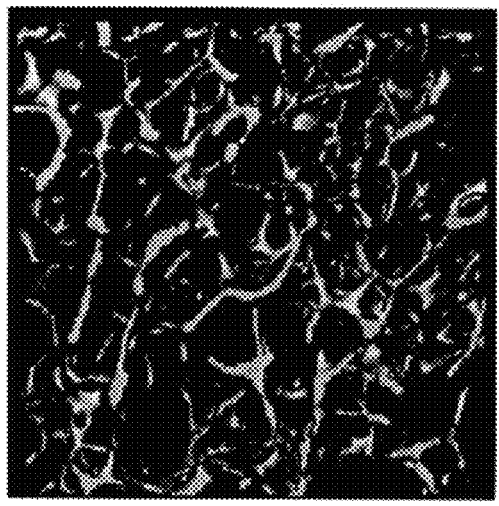
Figure 2A:
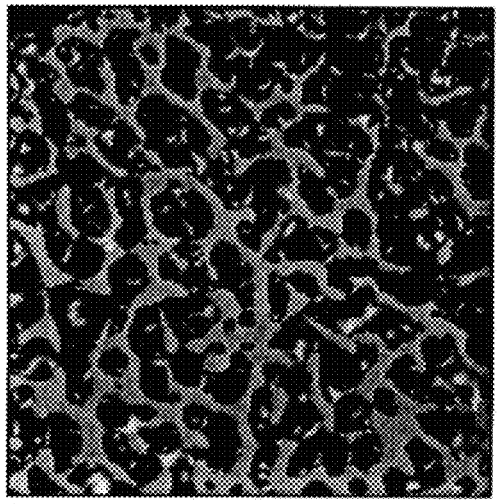

The structural model index (SMI) is an indicator of trabecular micro-architecture with 0 indicating parallel plate-like formation (a stronger, more structurally mature form) and 3 indicating cylindrical rod-like trabecular (more fragile, degenerating structure). The higher SMI in DM/HC animals shows degeneration of the bone micro-architecture, as shown in FIG. 2B as compared with normal controls (FIG. 2A). In Lp-PLA2 inhibitor treated animals, the DM/HC-induced degenerative changes were minimized, as shown in FIG. 2C.

The BV/TV (bone volume over total volume) is a volumetric indicator of the bone and the BS/BV (bone surface over bone volume) indicates bone structure. Strong bones have higher BV/TV and thin bones have higher BS/BV. DM/HC animals exhibited reduced BV/TV and increased BS/BV, demononstrating DM/HC animals have osteoporotic pathogenesis. On the contrary, DM/HC animals treated with the Lp-PLA$_2$ inhibitor SB480848 showed no osteoporotic changes.

Tb.Th is a measurement of trabecular thickness. DM/HC animals showed reduced Tb.Th, whereas the reduced Tb.Th thickness was prevented in DM/HC animals treated with the Lp-PLA$_2$ inhibitor.

Other indicators used include: Trabecular separation (Tb.Sp), trabecular number (TbN), and connectivity density (ConnD), which showed no significant changes between control and DM/HC animals, or DM/HC animals treated with the Lp-PLA$_2$ inhibitor SB480848.

During the study period, it was observed that animals administered the Lp-PLA$_2$ inhibitor were more responsive to external stimuli, demonstrated increased activity in the cage, and tended to respond more alertly to feeding and handing as compared to the control animals. Also, despite similar serum glucose and cholesterol levels, animals treated with the Lp-PLA$_2$ inhibitor demonstrated an increase in weight as compared to control animals (62.5 kg vs 50.9 kg for control animals) from a baseline of 26.9 kg and 30.3 kg weight respectively. Weight in animals administered the Lp-PLA$_2$ inhibitor is a direct reflection of their overall well-being, insofar as that more sickly animals (i.e. the control animals) do not eat. It was observed that inhibition of inflammation by a LP-PLA$_2$ inhibitor results in greater well-being and health in the setting of systemic inflammation.

EXAMPLE 2

Lp-PLA$_2$ Inhibitor Restored Bone Marrow Homeostasis

Figure 3B:
FIG. 3 shows examples of DM/HC-induced changes in the trabecular bone environment, as shown in FIG. 3B as compared to control non-DM/HC animals, shown in FIG. 3A.
Figure 3A:
Figure 4A:
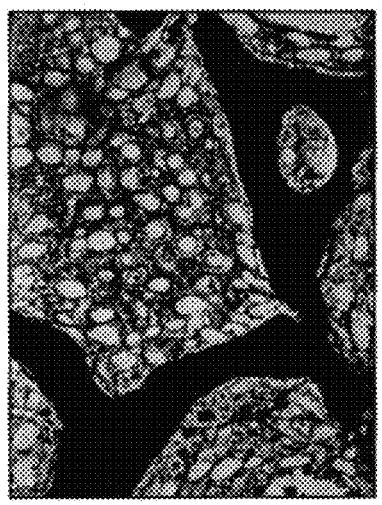
FIG. 4 shows the Lp-PLA$_2$ inhibitor restored normal bone marrow and abnormalities in bone marrow such abnormal bone marrow homeostasis. Examples of DM/HC-induced changes in the trabecular bone environment are shown in panels FIG. 4A-D as compared to DM/HC animals administered an Lp-PLA$_2$ inhibitor, which are shown in panels FIG. 4E-4H.
Figure 4B:
Figure 4C:
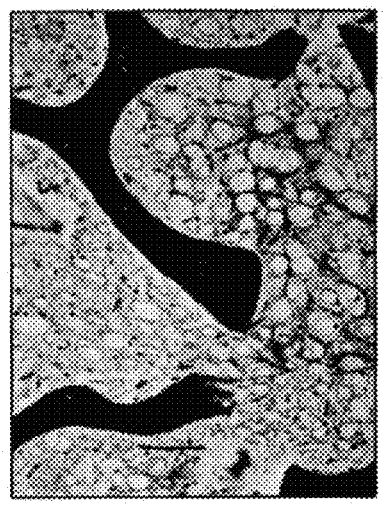
Figure 4D:
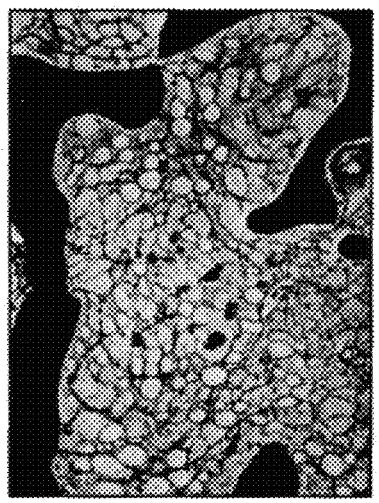
Figure 4F:
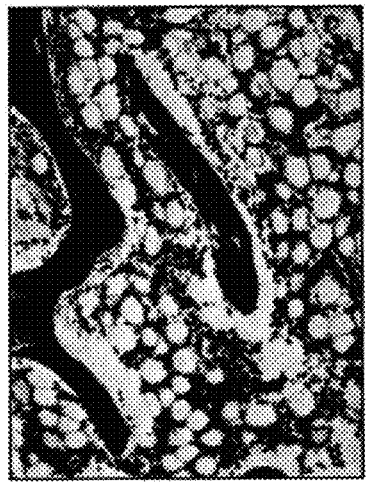
Figure 4H:
Figure 4E:
Figure 4G:
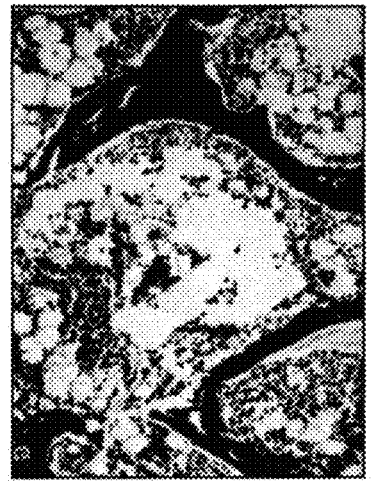

Histochemical staining with H&E-AB of trabecular bone areas showed distinct morphological changes between DM/HC animals and animals treated with the Lp-PLA$_2$ inhibitor SB480848. DM/HC animals showed marrow hypoplasia, fat atrophy, and deposition of extracellular "gelatinous" material (gelatinous transformation) as shown in FIG. 3B. Excess glycosaminoglycan, significantly alters the bone marrow microenvironment, is detrimental to erythropoiesis, as well as osteogenesis. In trabecular bone marrow, striking abnormalities were observed in DM/HC animals, as shown in FIG. 3B and FIG. 4A-D, with increased extracellular material, reduced cellularility and shrinkage of adipocyte as compared to control non-DM/HC animals as shown in FIG. 3A. In contrast, the bone marrow of DM/HC animals treated with a Lp-PLA$_2$ inhibitor are shown in FIG. 4E-G, which was similar to normal control animals (for example non-treated non-DM/HC animals as shown in FIG. 3A) and did not show abnormalities in bone marrow that occurred in non-treated DM/HC animals, demonstrating the Lp-PLA$_2$ inhibitor preserved bone marrow homeostasis.

Figure 5B:
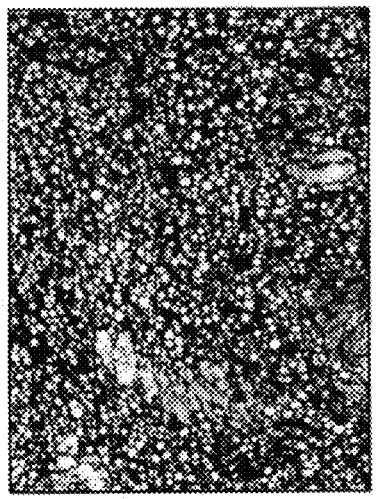
FIG. 5 shows the Lp-PLA$_2$ inhibitor preserved normal bone marrow and prevented abnormal bone marrow, such as abnormal bone marrow homeostasis in remote trabacular bone. Examples of low magnification images of DM/HC-induced changes in the trabecular bone environment are shown in panels FIGS. 5A and B as compared to DM/HC animals administered a Lp-PLA$_2$ inhibitor, which are shown in panels FIGS. 5C and D.
Figure 5D:
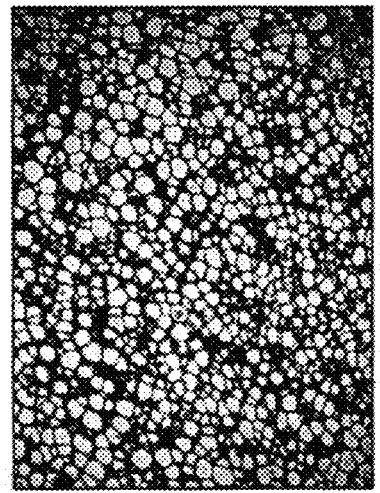
Figure 5A:
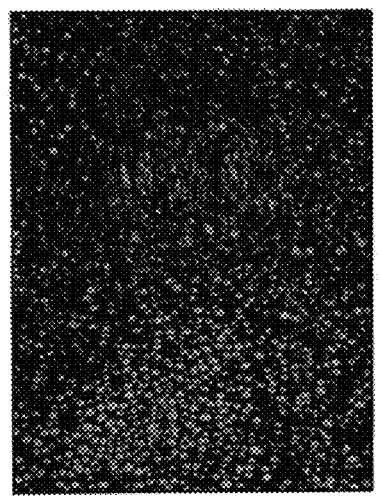
Figure 5C:
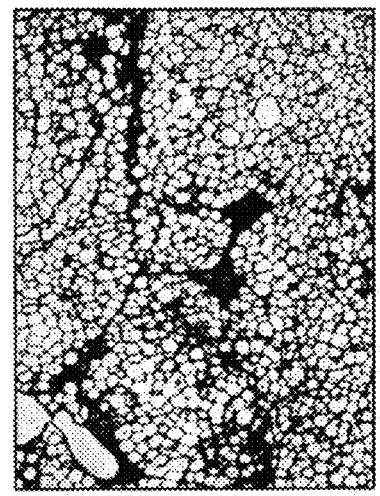
Figure 6C:
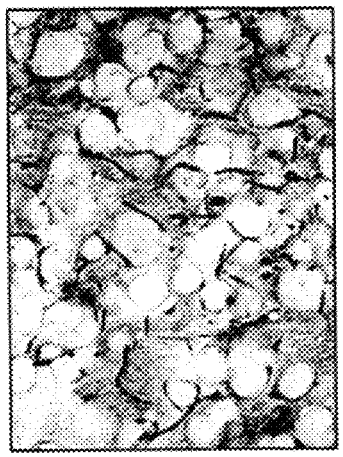
FIG. 6 shows the Lp-PLA$_2$ inhibitor preserved normal bone marrow and prevented abnormal bone marrow, such as abnormal bone marrow homeostasis in remote trabacular bone. Examples of high magnification images of DM/HC-induced changes in the trabecular bone environment are shown in panels FIG. 6A-C as compared to DM/HC animals administered a Lp-PLA$_2$ inhibitor, which are shown in panels FIG. 6D-6F.
Figure 6F:
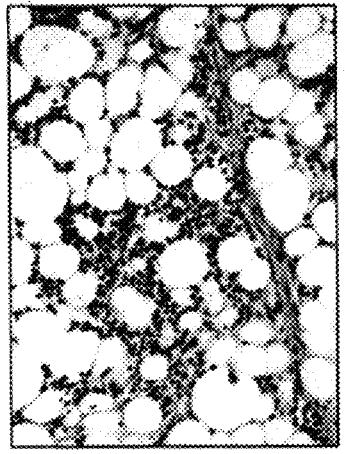
Figure 6B:
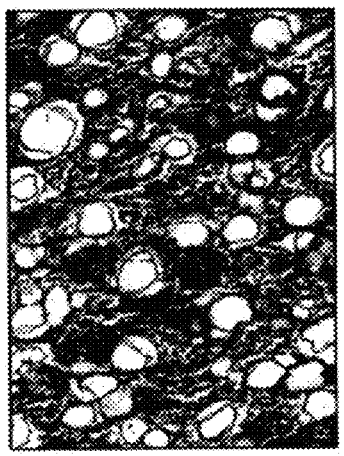
Figure 6E:
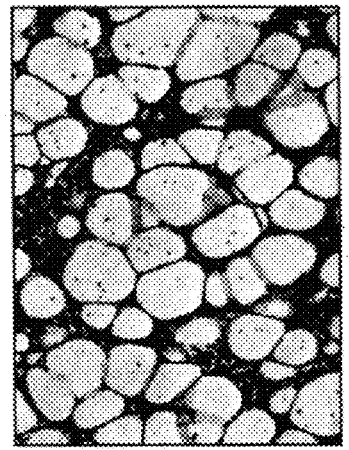
Figure 6A:
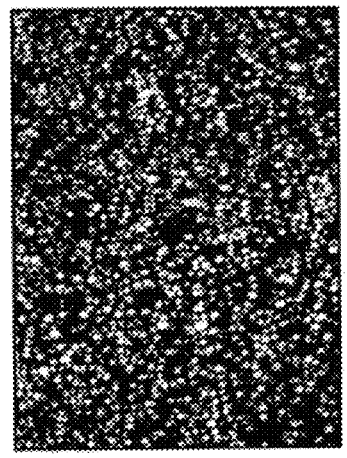
Figure 6D:
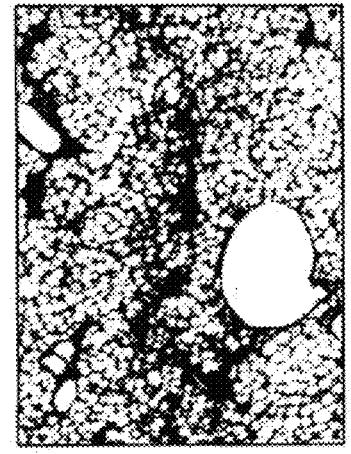

Bone marrow homeostasis was also preserved in bone marrow located remotely from traebucular bone, as shown in a low magnification image of the bone marrow remote from the trabecular bone in FIG. 5, animals treated with the Lp-PLA$_2$ inhibitor have normal bone marrow as shown in FIGS. 5C and D, whereas abnormal homeostasis occurred in non-treated DM/HC animals, as shown in FIGS. 5A and B. Higher magnification images of bone marrow remote from the trabecular bone are shown in FIG. 6D-F, where the Lp-PLA$_2$ inhibitor prevented DM/HC-induced bone marrow abnormalities that occurred in non-treated DM/HC animals (as shown in FIG. 6A-C).

EXAMPLE 3

Inhibition of Loss of Osteocytes and Osteblasts by Inhibitors of Lp-PLA$_2$

Figure 7A:
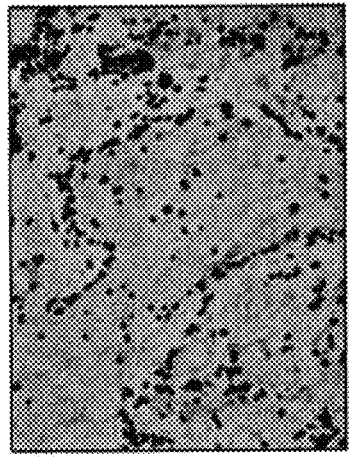
FIG. 7 shows examples of DM/HC-induced TUNEL positive cells within the trabecular bone environment as shown in panels FIG. 7A-D, as compared to the effects of animals treated with the Lp-PLA$_2$ inhibitor SB480848, as shown in FIGS. 7E-H.
Figure 7B:
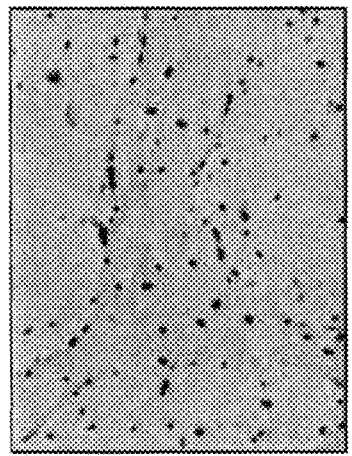
Figure 7C:
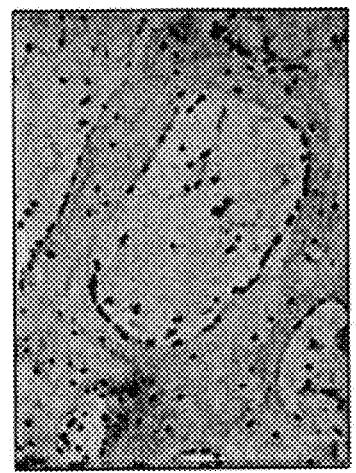
Figure 7D:
Figure 7F:
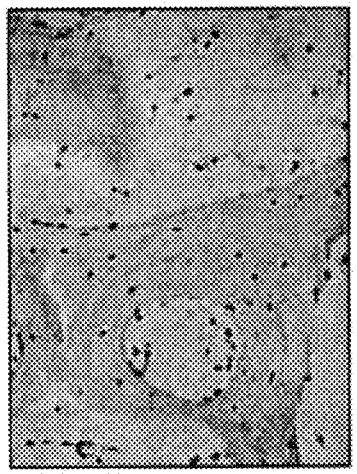
Figure 7H:
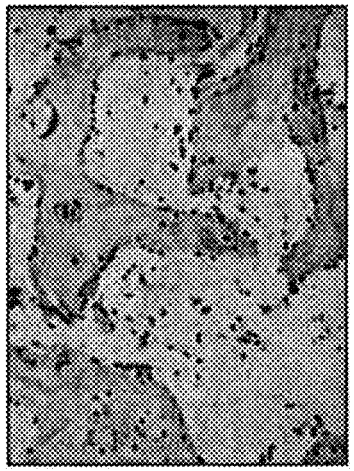
Figure 7E:
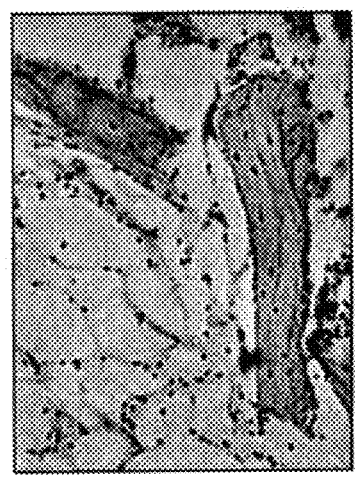
Figure 7G:

TUNEL staining of regions of trabecular bone were assessed in both DM/HC animals not treated and DM/HC animals treated with an Lp-PLA$_2$ inhibitor. The animals not treated with the Lp-PLA$_2$ inhibitor show dramatic increases in TUNEL positive cells within the trabecular bone, for example increased TUNEL positive osteocytes, and increased TUNEL positive osteoblasts on the surface the trabecular bone, as shown in FIG. 7A, as compared to animals treated with the Lp-PLA$_2$ inhibitor, as shown in FIG. 4B. Increased apoptosis in DM/HC animals demonstrates increase bone loss, fast bone turn over and reduced bone formation as compared to DM/HC animals treated with a Lp-PLA$_2$ inhibitor, which demonstrate less bone loss as demonstrated by micro CT analysis as shown in Example 1.

EXAMPLE 4

Figure 8B:
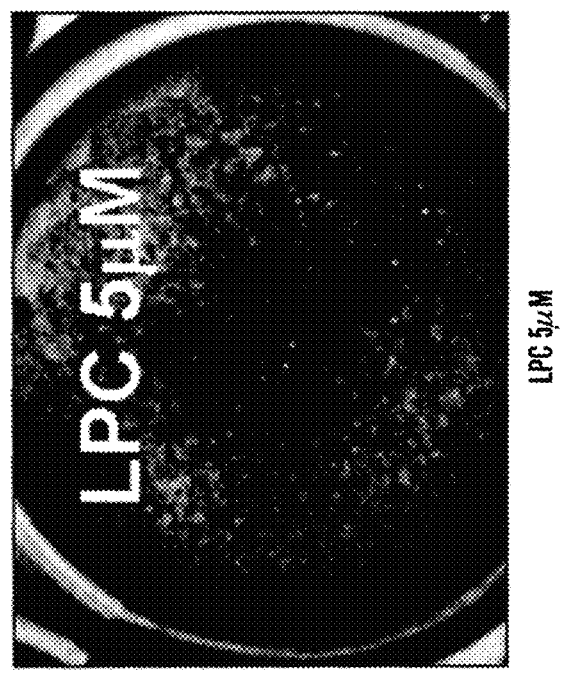
FIG. 8 shows the results of MLO-A5 cells treated with 5 µM LysoPC after 7 days, showing in panel 8B reduced mineralization in LysoPC treated cells as compared to control treatment in Panel 8A which has increased intensity of Alizarin red staining.
Figure 8A:
Figure 9A:
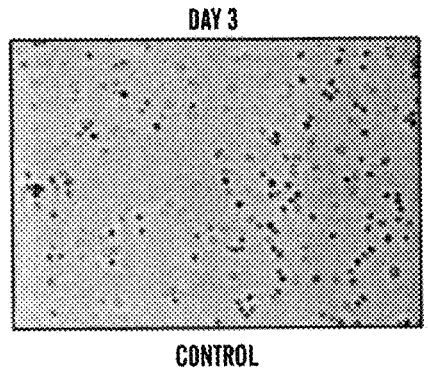
FIGS. 9A and 9B show examples of alkaline phosphatase staining in control treated cells.
Figure 9B:
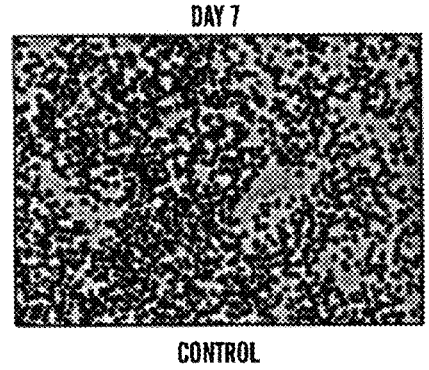
Figure 9C:
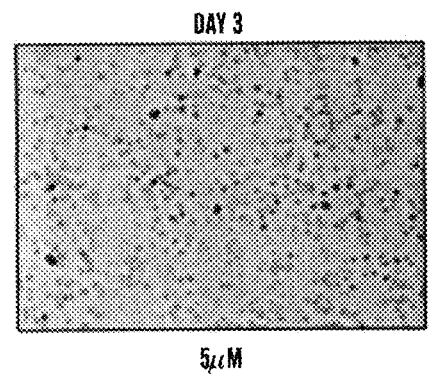
FIGS. 9C and 9D show examples of alkaline phosphatase staining in cells treated with 5 µM LysoPC.
Figure 9D:
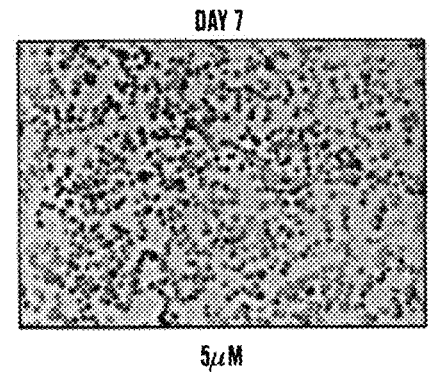
Figure 9E:
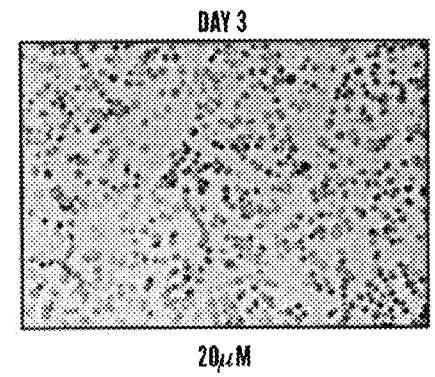
FIGS. 9E and 9F show examples of alkaline phosphatase staining in cells treated with 20 µM LysoPC, showing reduced alkaline phosphatase staining of MLO-A5 cells treated with at least 5 µM LysoPC at 7 days as compared to control cells at 7 days.
Figure 9F:
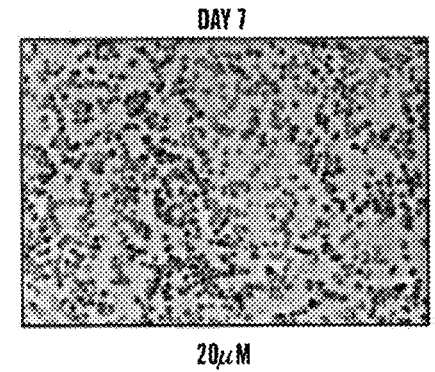

Activation of the Lp-PLA$_2$ Pathway by LypoPC Prevents Osteoblast Mineralization, Osteoblast Differentiation and Proliferation Alizarin Red and Alkaline Phosphatase Staining are bone marker proteins indicating the degree of mineralization and intensity of osteblast differentiation, respectively. MLO-A5 osteoblastic cells stained with alizarin Red following treatment with 5 μM LysoPC caused decreased mineralization of MLO-A5 cells, compared to non-treated control cells, after 7 days as shown by Alizarin Red Staining in FIG. 8.

Treatment with 5 μM LysoPC caused decreased alkaline phosphatase staining of MLO-A5 cells after 7 day treatment as compared to control, as shown in FIG. 9.

Figure 10:
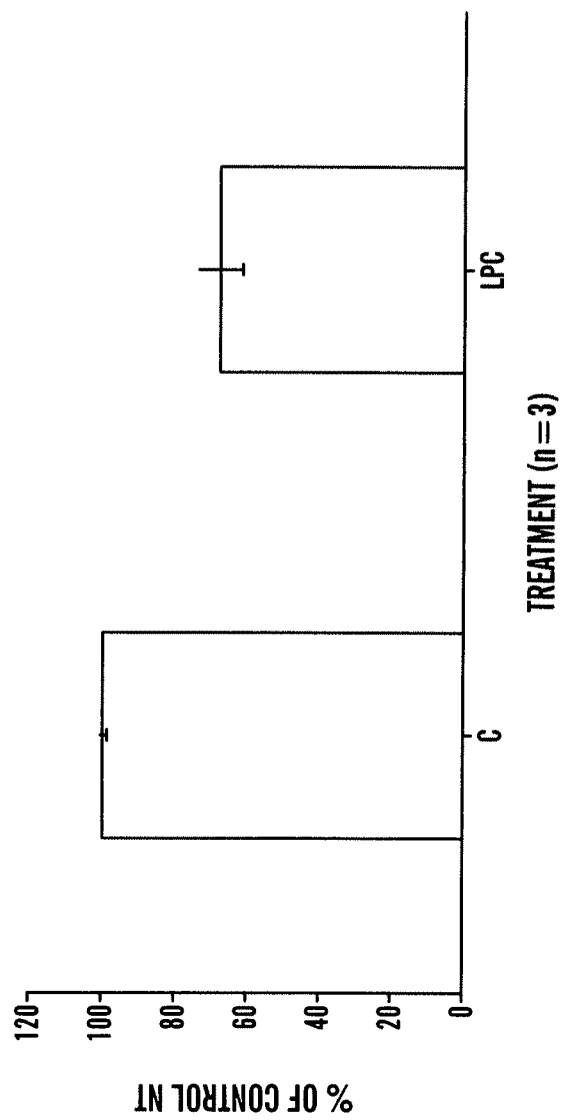
FIG. 10 shows the results from the proliferation assay, showing MLO-A5 cells treated with 5 µM LysoPC for 18 hours show reduced proliferation.

As shown, FIG. 10, MLO-A5 cells treated with 5 μM LysoPC for 18 hours show reduced proliferation, as compared to non-treated cells, demonstrating that activation of the Lp-PLA$_2$ pathway by LysoPC prevents proliferation of osteoblasts.

REFERENCES

The references cited herein and throughout the application are incorporated herein by reference.

The invention claimed is:

1. A method of treating and/or preventing a metabolic bone disease in a patient, wherein the patient is identified as having, or having an increased likelihood of risk of developing a metabolic bone disease, the method comprising administering to the patient in need thereof an effective amount of a pharmaceutical composition comprising 1-(N-(2-(diethylamino)ethyl)-N-(4-(4-trifluoromethylphenyl)benzyl)-aminocarbonylmethyl)-2-(4-fluorobenzyl)thio-5,6-trimethylenepyrimidin-4-one.

2. The method of claim 1, wherein the metabolic bone disease is selected from a group consisting of: osteoporosis, osteopenia, and abnormal bone marrow.

3. The method of claim 1 comprising a first step of screening the patient for likelihood of having, or developing a metabolic bone disease, wherein if the patient is identified to have an increased risk or likelihood of developing a metabolic bone disorder, administering a pharmaceutical composition comprising an effective amount of 1-(N-(2-(diethylamino)ethyl)-N-(4-(4-trifluoromethylphenyObenzyl)-aminocarbonylmethyl)-2-(4-fluorobenzyl)thio-5,6-trimethylenepyrimidin-4-one.

4. A method for preventing or reducing the risk of developing osteoporosis or osteopenia in a patient, the method comprising assessing the risk of a patient developing osteoporosis or osteopenia, wherein a clinician directs the patient to be treated with a pharmaceutical composition comprising an effective amount of 1-(N-(2-(diethylamino)ethyl)-N-(4-(4-trifluoromethylphenyl)benzyl)-aminocarbonylmethyl)-2-(4-fluorobenzyl)thio-5,6-trimethylenepyrimidin-4-one if the patient is at risk of developing osteoporosis or osteopenia.

5. A method of treating and/or preventing abnormalities in the bone marrow comprising administering to a patient with or at risk of developing such bone marrow abnormalities a pharmaceutical composition comprising an effective amount of 1-(N-(2-diethylamino)ethyl)-N-(4-(4-trifluoromethylphenyl)benzyl)-aminocarbonylmethyl)-2-(4-fluorobenzyl)thio-5,6-trimethylenepyrimidin-4-one.

6. The method of claim 5, wherein the abnormal bone marrow comprises at least one of excess glycosaminoglycan, or hypoplasia, fat atrophy and deposition of gelatinous material.

7. The method of claim 1, wherein the metabolic disease is osteoporosis.

8. A method of preventing and/or treating loss of bone matrix density in a patient in need thereof, wherein the method comprises administering to the patient a pharmaceutical composition comprising an effective amount of 1-(N-(2-(diethylamino)ethyl)-N-(4-(4-trifluoromethylphenyl)benzyl)-aminocarbonylmethyl)-2-(4-fluorobenzyl)thio-5,6-trimethylenepyrimidin-4-one.

9. The method of claim 1, or 8, further comprising monitoring treatment by assessing bone density and/or bone mass.

10. The method of claim 1, 4, 5, or 8, further comprising administering to the patient additional therapeutic agents.

11. The method of claim 10, wherein additional therapeutic agents are estrogens, bisphosphonates, calcitonin, flavonoids, and selective estrogen receptor modulators, parathyroid hormones, strontium ranelate, growth hormone and insulin-like growth factor and variants thereof.

* * * * *